United States Patent
Steinke et al.

(10) Patent No.: US 9,125,666 B2
(45) Date of Patent: *Sep. 8, 2015

(54) SELECTABLE ECCENTRIC REMODELING AND/OR ABLATION OF ATHEROSCLEROTIC MATERIAL

(75) Inventors: Tom A. Steinke, San Diego, CA (US);
Corbett W. Stone, San Diego, CA (US);
Stephen O. Ross, Fallbrook, CA (US);
Brian S. Kelleher, Ramona, CA (US);
Raphael M. Michel, San Diego, CA (US); Donald H. Koenig, San Diego, CA (US)

(73) Assignee: VESSIX VASCULAR, INC., Laguna Hills, CA (US)

( * ) Notice: Subject to any disclaimer, the term of this patent is extended or adjusted under 35 U.S.C. 154(b) by 1437 days.

This patent is subject to a terminal disclaimer.

(21) Appl. No.: 11/864,779

(22) Filed: Sep. 28, 2007

(65) Prior Publication Data

US 2008/0161801 A1    Jul. 3, 2008

Related U.S. Application Data

(62) Division of application No. 10/938,138, filed on Sep. 10, 2004, now Pat. No. 7,291,146.

(60) Provisional application No. 60/502,515, filed on Sep. 12, 2003.

(51) Int. Cl.
*A61B 18/14* (2006.01)
*A61B 18/18* (2006.01)
(Continued)

(52) U.S. Cl.
CPC ............. *A61B 18/1492* (2013.01); *A61B 18/18* (2013.01); *A61B 18/1815* (2013.01);
(Continued)

(58) Field of Classification Search
USPC ................ 606/41, 47–50; 607/101, 102, 122; 600/439

See application file for complete search history.

(56) References Cited

U.S. PATENT DOCUMENTS

| 164,184 A | 6/1875 | Kiddee |
|---|---|---|
| 1,167,014 A | 1/1916 | O'Brien |

(Continued)

FOREIGN PATENT DOCUMENTS

| CA | 2384866 A1 | 5/2001 |
|---|---|---|
| CN | 101583323 A | 11/2009 |

(Continued)

OTHER PUBLICATIONS

Supplementary Partial European Search Report of Application No. 04816863.7, mailed May 5, 2009, 7 pages total.

(Continued)

*Primary Examiner* — Michael Peffley
(74) *Attorney, Agent, or Firm* — Seager, Tufte & Wickhem, LLC

(57) ABSTRACT

A catheter and catheter system for eccentric remodeling and/or removal of atherosclerotic material of a blood vessel of a patient include an elongate flexible catheter body with a radially expandable structure. A plurality of electrodes or other electrosurgical energy delivery surfaces can radially engage atherosclerotic material when the structure expands. An atherosclerotic material detector near the distal end of the catheter body may measure circumferential atherosclerotic material distribution, and a power source selectively energizes the electrodes to eccentrically remodel the measured atherosclerotic material.

13 Claims, 39 Drawing Sheets

(51) Int. Cl.
*A61B 18/00* (2006.01)
*A61B 19/00* (2006.01)

(52) U.S. Cl.
CPC . *A61B2018/0016* (2013.01); *A61B 2018/0022* (2013.01); *A61B 2018/0041* (2013.01); *A61B 2018/00214* (2013.01); *A61B 2018/00267* (2013.01); *A61B 2018/1861* (2013.01); *A61B 2019/528* (2013.01); *A61B 2019/5231* (2013.01); *A61B 2019/5236* (2013.01); *A61B 2019/5238* (2013.01); *A61B 2218/002* (2013.01); *A61B 2218/007* (2013.01)

(56) References Cited

U.S. PATENT DOCUMENTS

| | | | |
|---|---|---|---|
| 2,505,358 | A | 4/1950 | Gusberg et al. |
| 2,701,559 | A | 2/1955 | Cooper |
| 3,108,593 | A | 10/1963 | Glassman |
| 3,108,594 | A | 10/1963 | Glassman |
| 3,540,431 | A | 11/1970 | Mobin |
| 3,952,747 | A | 4/1976 | Kimmell |
| 3,996,938 | A | 12/1976 | Clark, III |
| 4,046,150 | A | 9/1977 | Schwartz et al. |
| 4,290,427 | A | 9/1981 | Chin |
| 4,402,686 | A | 9/1983 | Medel |
| 4,483,341 | A | 11/1984 | Witteles et al. |
| 4,574,804 | A | 3/1986 | Kurwa |
| 4,587,975 | A | 5/1986 | Salo et al. |
| 4,649,936 | A | 3/1987 | Ungar et al. |
| 4,682,596 | A | 7/1987 | Bales et al. |
| 4,699,147 | A * | 10/1987 | Chilson et al. ............... 600/374 |
| 4,709,698 | A | 12/1987 | Johnston et al. |
| 4,765,331 | A | 8/1988 | Petruzzi et al. |
| 4,770,653 | A | 9/1988 | Shturman |
| 4,784,132 | A | 11/1988 | Fox et al. |
| 4,784,162 | A | 11/1988 | Ricks et al. |
| 4,785,806 | A | 11/1988 | Deckelbaum et al. |
| 4,788,975 | A | 12/1988 | Shturman et al. |
| 4,790,310 | A | 12/1988 | Ginsburg et al. |
| 4,799,479 | A | 1/1989 | Spears |
| 4,823,791 | A | 4/1989 | D'Amelio et al. |
| 4,830,003 | A | 5/1989 | Wolff et al. |
| 4,849,484 | A | 7/1989 | Heard |
| 4,862,886 | A | 9/1989 | Clarke et al. |
| 4,887,605 | A | 12/1989 | Angelsen et al. |
| 4,920,979 | A | 5/1990 | Bullara et al. |
| 4,938,766 | A | 7/1990 | Jarvik |
| 4,955,377 | A | 9/1990 | Lennox et al. |
| 4,976,711 | A * | 12/1990 | Parins et al. ............... 606/48 |
| 5,034,010 | A | 7/1991 | Kittrell et al. |
| 5,052,402 | A | 10/1991 | Bencini et al. |
| 5,053,033 | A | 10/1991 | Clarke et al. |
| 5,071,424 | A | 12/1991 | Reger et al. |
| 5,074,871 | A | 12/1991 | Groshong et al. |
| 5,098,429 | A | 3/1992 | Sterzer et al. |
| 5,098,431 | A | 3/1992 | Rydell |
| 5,102,402 | A | 4/1992 | Dror et al. |
| RE33,925 | E | 5/1992 | Bales et al. |
| 5,109,859 | A | 5/1992 | Jenkins |
| 5,125,928 | A | 6/1992 | Parins et al. |
| 5,129,396 | A | 7/1992 | Rosen et al. |
| 5,139,496 | A | 8/1992 | Hed |
| 5,143,836 | A | 9/1992 | Hartman et al. |
| 5,156,151 | A | 10/1992 | Imran |
| 5,156,610 | A | 10/1992 | Reger et al. |
| 5,158,564 | A | 10/1992 | Schnepp-Pesch |
| 5,170,802 | A | 12/1992 | Mehra |
| 5,178,620 | A | 1/1993 | Eggers et al. |
| 5,178,625 | A | 1/1993 | Groshong et al. |
| 5,190,540 | A | 3/1993 | Lee |
| 5,191,883 | A | 3/1993 | Lennox et al. |
| 5,211,651 | A | 5/1993 | Reger et al. |
| 5,234,407 | A | 8/1993 | Teirstein et al. |
| 5,242,441 | A | 9/1993 | Avitall |
| 5,251,634 | A | 10/1993 | Weinberg et al. |
| 5,254,098 | A | 10/1993 | Ulrich et al. |
| 5,255,679 | A | 10/1993 | Imran |
| 5,263,493 | A | 11/1993 | Avitall |
| 5,267,954 | A | 12/1993 | Nita et al. |
| 5,277,201 | A | 1/1994 | Stern et al. |
| 5,282,484 | A | 2/1994 | Reger |
| 5,286,254 | A | 2/1994 | Shapland et al. |
| 5,295,484 | A | 3/1994 | Marcus |
| 5,297,564 | A | 3/1994 | Love et al. |
| 5,300,068 | A | 4/1994 | Rosar et al. |
| 5,301,683 | A | 4/1994 | Durkan |
| 5,304,115 | A | 4/1994 | Pflueger et al. |
| 5,304,121 | A | 4/1994 | Sahatjian |
| 5,304,171 | A | 4/1994 | Gregory et al. |
| 5,304,173 | A | 4/1994 | Kittrell et al. |
| 5,306,250 | A | 4/1994 | March et al. |
| 5,312,328 | A | 5/1994 | Nita et al. |
| 5,314,466 | A | 5/1994 | Stern et al. |
| 5,322,064 | A | 6/1994 | Lundquist |
| 5,324,255 | A | 6/1994 | Passafaro et al. |
| 5,326,341 | A | 7/1994 | Lew et al. |
| 5,326,342 | A | 7/1994 | Pflueger et al. |
| 5,330,518 | A | 7/1994 | Neilson et al. |
| 5,333,614 | A | 8/1994 | Feiring |
| 5,342,292 | A | 8/1994 | Nita et al. |
| 5,344,395 | A | 9/1994 | Whalen et al. |
| 5,345,936 | A | 9/1994 | Pomeranz et al. |
| 5,364,392 | A | 11/1994 | Warner et al. |
| 5,365,172 | A | 11/1994 | Hrovat et al. |
| 5,368,557 | A | 11/1994 | Nita et al. |
| 5,368,558 | A | 11/1994 | Nita et al. |
| 5,372,138 | A | 12/1994 | Crowley et al. |
| 5,380,274 | A | 1/1995 | Nita et al. |
| 5,380,319 | A | 1/1995 | Saito et al. |
| 5,382,228 | A | 1/1995 | Nita et al. |
| 5,383,874 | A | 1/1995 | Jackson et al. |
| 5,383,917 | A | 1/1995 | Desai et al. |
| 5,397,301 | A | 3/1995 | Pflueger et al. |
| 5,397,339 | A | 3/1995 | Desai |
| 5,401,272 | A | 3/1995 | Perkins et al. |
| 5,403,311 | A | 4/1995 | Abele et al. |
| 5,405,318 | A | 4/1995 | Nita et al. |
| 5,405,346 | A | 4/1995 | Grundy et al. |
| 5,409,000 | A * | 4/1995 | Imran ............... 600/374 |
| 5,417,672 | A | 5/1995 | Nita et al. |
| 5,419,767 | A | 5/1995 | Eggers et al. |
| 5,427,118 | A | 6/1995 | Nita et al. |
| 5,432,876 | A | 7/1995 | Appeldorn et al. |
| 5,441,498 | A | 8/1995 | Perkins et al. |
| 5,447,509 | A | 9/1995 | Mills et al. |
| 5,451,207 | A | 9/1995 | Yock et al. |
| 5,453,091 | A | 9/1995 | Taylor et al. |
| 5,454,788 | A | 10/1995 | Walker et al. |
| 5,454,809 | A | 10/1995 | Janssen |
| 5,455,029 | A | 10/1995 | Hartman et al. |
| 5,456,682 | A | 10/1995 | Edwards et al. |
| 5,457,042 | A | 10/1995 | Hartman et al. |
| 5,471,982 | A * | 12/1995 | Edwards et al. ............... 600/374 |
| 5,474,530 | A | 12/1995 | Passafaro et al. |
| 5,478,351 | A | 12/1995 | Meade et al. |
| 5,496,311 | A | 3/1996 | Abele et al. |
| 5,496,312 | A | 3/1996 | Klicek et al. |
| 5,498,261 | A | 3/1996 | Strul |
| 5,505,201 | A | 4/1996 | Grill et al. |
| 5,505,730 | A | 4/1996 | Edwards |
| 5,507,744 | A | 4/1996 | Tay et al. |
| 5,522,873 | A | 6/1996 | Jackman et al. |
| 5,531,520 | A | 7/1996 | Grimson et al. |
| 5,540,656 | A | 7/1996 | Pflueger et al. |
| 5,540,679 | A | 7/1996 | Fram et al. |
| 5,540,681 | A | 7/1996 | Strul et al. |
| 5,542,917 | A | 8/1996 | Nita et al. |
| 5,545,161 | A | 8/1996 | Imran |
| 5,562,100 | A | 10/1996 | Kittrell et al. |
| 5,571,122 | A | 11/1996 | Kelly et al. |
| 5,571,151 | A | 11/1996 | Gregory |
| 5,573,531 | A | 11/1996 | Gregory |
| 5,573,533 | A | 11/1996 | Strul |

(56) References Cited

U.S. PATENT DOCUMENTS

| | | |
|---|---|---|
| 5,584,831 A | 12/1996 | McKay |
| 5,584,872 A | 12/1996 | Lafontaine et al. |
| 5,588,962 A | 12/1996 | Nicholas et al. |
| 5,599,346 A | 2/1997 | Edwards et al. |
| 5,601,526 A | 2/1997 | Chapelon et al. |
| 5,609,606 A | 3/1997 | O'Boyle et al. |
| 5,626,576 A * | 5/1997 | Janssen .................... 606/41 |
| 5,630,837 A | 5/1997 | Crowley |
| 5,637,090 A | 6/1997 | McGee et al. |
| 5,643,255 A | 7/1997 | Organ |
| 5,643,297 A | 7/1997 | Nordgren et al. |
| 5,647,847 A | 7/1997 | Lafontaine et al. |
| 5,649,923 A | 7/1997 | Gregory et al. |
| 5,651,780 A | 7/1997 | Jackson et al. |
| 5,653,684 A | 8/1997 | Laptewicz et al. |
| 5,662,671 A | 9/1997 | Barbut et al. |
| 5,665,062 A | 9/1997 | Houser |
| 5,665,098 A | 9/1997 | Kelly et al. |
| 5,666,964 A | 9/1997 | Meilus |
| 5,667,490 A | 9/1997 | Keith et al. |
| 5,672,174 A | 9/1997 | Gough et al. |
| 5,676,693 A | 10/1997 | Lafontaine |
| 5,678,296 A | 10/1997 | Fleischhacker et al. |
| 5,681,282 A | 10/1997 | Eggers et al. |
| RE35,656 E | 11/1997 | Feinberg |
| 5,688,266 A | 11/1997 | Edwards et al. |
| 5,693,015 A | 12/1997 | Walker et al. |
| 5,693,029 A | 12/1997 | Leonhardt et al. |
| 5,693,043 A | 12/1997 | Kittrell et al. |
| 5,693,082 A | 12/1997 | Warner et al. |
| 5,695,504 A | 12/1997 | Gifford et al. |
| 5,697,369 A | 12/1997 | Long, Jr. et al. |
| 5,697,909 A | 12/1997 | Eggers et al. |
| 5,702,386 A | 12/1997 | Stern et al. |
| 5,702,433 A | 12/1997 | Taylor et al. |
| 5,706,809 A | 1/1998 | Littmann et al. |
| 5,713,942 A | 2/1998 | Stern et al. |
| 5,715,819 A | 2/1998 | Svenson et al. |
| 5,722,401 A | 3/1998 | Pietroski et al. |
| 5,735,846 A | 4/1998 | Panescu et al. |
| 5,741,214 A | 4/1998 | Ouchi et al. |
| 5,741,248 A | 4/1998 | Stern et al. |
| 5,741,249 A | 4/1998 | Moss et al. |
| 5,743,903 A | 4/1998 | Stern et al. |
| 5,748,347 A | 5/1998 | Erickson |
| 5,749,914 A | 5/1998 | Janssen |
| 5,755,682 A | 5/1998 | Knudson et al. |
| 5,755,715 A | 5/1998 | Stern et al. |
| 5,755,753 A | 5/1998 | Knowlton et al. |
| 5,769,847 A | 6/1998 | Panescu et al. |
| 5,769,880 A | 6/1998 | Truckai et al. |
| 5,775,338 A | 7/1998 | Hastings |
| 5,776,174 A | 7/1998 | Van Tassel |
| 5,779,698 A | 7/1998 | Clayman et al. |
| 5,782,760 A | 7/1998 | Schaer |
| 5,785,702 A | 7/1998 | Murphy et al. |
| 5,792,105 A | 8/1998 | Lin et al. |
| 5,797,849 A | 8/1998 | Vesely et al. |
| 5,797,903 A | 8/1998 | Swanson et al. |
| 5,800,484 A | 9/1998 | Gough et al. |
| 5,800,494 A | 9/1998 | Campbell et al. |
| 5,807,306 A | 9/1998 | Shapland et al. |
| 5,810,802 A | 9/1998 | Panescu et al. |
| 5,810,803 A | 9/1998 | Moss et al. |
| 5,810,810 A | 9/1998 | Tay et al. |
| 5,817,092 A | 10/1998 | Behl |
| 5,817,113 A | 10/1998 | Gifford et al. |
| 5,817,144 A | 10/1998 | Gregory et al. |
| 5,823,956 A | 10/1998 | Roth et al. |
| 5,827,203 A | 10/1998 | Nita et al. |
| 5,827,268 A | 10/1998 | Laufer |
| 5,829,447 A | 11/1998 | Stevens et al. |
| 5,830,213 A | 11/1998 | Panescu et al. |
| 5,830,222 A | 11/1998 | Makower |
| 5,832,228 A | 11/1998 | Holden et al. |
| 5,833,593 A | 11/1998 | Liprie |
| 5,836,874 A | 11/1998 | Swanson et al. |
| 5,840,076 A | 11/1998 | Swanson et al. |
| 5,843,016 A | 12/1998 | Lugnani et al. |
| 5,846,238 A | 12/1998 | Jackson et al. |
| 5,846,239 A | 12/1998 | Swanson et al. |
| 5,846,245 A | 12/1998 | McCarthy et al. |
| 5,848,969 A | 12/1998 | Panescu et al. |
| 5,853,411 A | 12/1998 | Whayne et al. |
| 5,855,614 A | 1/1999 | Stevens et al. |
| 5,860,974 A | 1/1999 | Abele |
| 5,865,801 A | 2/1999 | Houser |
| 5,868,735 A | 2/1999 | Lafontaine et al. |
| 5,868,736 A | 2/1999 | Swanson et al. |
| 5,869,127 A | 2/1999 | Zhong |
| 5,871,483 A | 2/1999 | Jackson et al. |
| 5,871,524 A | 2/1999 | Knowlton et al. |
| 5,875,782 A | 3/1999 | Ferrari et al. |
| 5,876,369 A | 3/1999 | Houser |
| 5,876,374 A | 3/1999 | Alba et al. |
| 5,876,397 A | 3/1999 | Edelman et al. |
| 5,879,348 A | 3/1999 | Owens et al. |
| 5,891,114 A | 4/1999 | Chien et al. |
| 5,891,135 A | 4/1999 | Jackson et al. |
| 5,891,136 A | 4/1999 | McGee et al. |
| 5,891,138 A | 4/1999 | Tu et al. |
| 5,895,378 A | 4/1999 | Nita |
| 5,897,552 A | 4/1999 | Edwards et al. |
| 5,902,328 A | 5/1999 | Lafontaine et al. |
| 5,904,651 A | 5/1999 | Swanson et al. |
| 5,904,667 A | 5/1999 | Falwell et al. |
| 5,904,697 A | 5/1999 | Gifford et al. |
| 5,904,709 A | 5/1999 | Arndt et al. |
| 5,906,614 A | 5/1999 | Stern et al. |
| 5,906,623 A | 5/1999 | Peterson |
| 5,906,636 A | 5/1999 | Casscells et al. |
| 5,916,192 A | 6/1999 | Nita et al. |
| 5,916,227 A | 6/1999 | Keith et al. |
| 5,916,239 A | 6/1999 | Geddes et al. |
| 5,919,219 A | 7/1999 | Knowlton et al. |
| 5,924,424 A | 7/1999 | Stevens et al. |
| 5,925,038 A | 7/1999 | Panescu et al. |
| 5,934,284 A | 8/1999 | Plaia et al. |
| 5,935,063 A | 8/1999 | Nguyen |
| 5,938,670 A | 8/1999 | Keith et al. |
| 5,947,977 A | 9/1999 | Slepian et al. |
| 5,948,011 A | 9/1999 | Knowlton et al. |
| 5,951,494 A | 9/1999 | Wang et al. |
| 5,951,539 A | 9/1999 | Nita et al. |
| 5,954,717 A | 9/1999 | Behl et al. |
| 5,957,882 A | 9/1999 | Nita et al. |
| 5,957,941 A | 9/1999 | Ream et al. |
| 5,957,969 A | 9/1999 | Warner et al. |
| 5,961,513 A | 10/1999 | Swanson et al. |
| 5,964,757 A | 10/1999 | Ponzi et al. |
| 5,967,976 A | 10/1999 | Larsen et al. |
| 5,967,978 A | 10/1999 | Littmann et al. |
| 5,967,984 A | 10/1999 | Chu et al. |
| 5,971,975 A | 10/1999 | Mills et al. |
| 5,972,026 A | 10/1999 | Laufer et al. |
| 5,980,563 A | 11/1999 | Tu et al. |
| 5,989,208 A | 11/1999 | Nita et al. |
| 5,989,284 A | 11/1999 | Laufer |
| 5,993,462 A | 11/1999 | Pomeranz et al. |
| 5,997,497 A | 12/1999 | Nita et al. |
| 5,999,678 A | 12/1999 | Murphy et al. |
| 6,004,269 A | 12/1999 | Crowley et al. |
| 6,004,316 A | 12/1999 | Laufer |
| 6,007,514 A | 12/1999 | Nita et al. |
| 6,010,522 A | 1/2000 | Barbut et al. |
| 6,013,033 A | 1/2000 | Berger et al. |
| 6,014,590 A | 1/2000 | Whayne et al. |
| 6,019,757 A | 2/2000 | Scheldrup |
| 6,022,309 A | 2/2000 | Celliers et al. |
| 6,024,740 A | 2/2000 | Lesh et al. |
| 6,030,611 A | 2/2000 | Gorecki et al. |
| 6,032,675 A | 3/2000 | Rubinsky et al. |
| 6,033,357 A | 3/2000 | Ciezki et al. |
| 6,033,397 A | 3/2000 | Laufer et al. |

(56) References Cited

U.S. PATENT DOCUMENTS

| | | | |
|---|---|---|---|
| 6,033,398 A | 3/2000 | Farley et al. | |
| 6,036,687 A | 3/2000 | Laufer et al. | |
| 6,036,689 A * | 3/2000 | Tu et al. | 606/41 |
| 6,041,260 A | 3/2000 | Stern et al. | |
| 6,050,994 A | 4/2000 | Sherman et al. | |
| 6,053,873 A | 4/2000 | Govari et al. | |
| 6,056,744 A | 5/2000 | Edwards | |
| 6,056,746 A | 5/2000 | Goble et al. | |
| 6,063,085 A | 5/2000 | Tay et al. | |
| 6,066,096 A | 5/2000 | Smith et al. | |
| 6,066,139 A | 5/2000 | Ryan et al. | |
| 6,068,638 A | 5/2000 | Makower | |
| 6,068,653 A | 5/2000 | Lafontaine | |
| 6,071,277 A | 6/2000 | Farley et al. | |
| 6,071,278 A | 6/2000 | Panescu et al. | |
| 6,078,839 A | 6/2000 | Carson | |
| 6,079,414 A | 6/2000 | Roth | |
| 6,080,171 A | 6/2000 | Keith et al. | |
| 6,081,749 A | 6/2000 | Ingle et al. | |
| 6,083,159 A | 7/2000 | Driscoll et al. | |
| 6,086,581 A | 7/2000 | Reynolds et al. | |
| 6,091,995 A | 7/2000 | Ingle et al. | |
| 6,093,166 A | 7/2000 | Knudson et al. | |
| 6,096,021 A | 8/2000 | Helm et al. | |
| 6,099,526 A | 8/2000 | Whayne et al. | |
| 6,102,908 A | 8/2000 | Tu et al. | |
| 6,106,477 A | 8/2000 | Miesel et al. | |
| 6,110,187 A | 8/2000 | Donlon et al. | |
| 6,114,311 A | 9/2000 | Parmacek et al. | |
| 6,117,101 A | 9/2000 | Diederich et al. | |
| 6,117,128 A | 9/2000 | Gregory | |
| 6,120,476 A | 9/2000 | Fung et al. | |
| 6,120,516 A | 9/2000 | Selmon et al. | |
| 6,121,775 A | 9/2000 | Pearlman | |
| 6,123,679 A | 9/2000 | Lafaut et al. | |
| 6,123,682 A | 9/2000 | Knudson et al. | |
| 6,123,702 A | 9/2000 | Swanson et al. | |
| 6,123,703 A | 9/2000 | Tu et al. | |
| 6,123,718 A | 9/2000 | Tu et al. | |
| 6,129,725 A | 10/2000 | Tu et al. | |
| 6,135,997 A | 10/2000 | Laufer et al. | |
| 6,142,991 A | 11/2000 | Schatzberger | |
| 6,142,993 A | 11/2000 | Whayne et al. | |
| 6,149,647 A | 11/2000 | Tu et al. | |
| 6,152,899 A | 11/2000 | Farley et al. | |
| 6,152,912 A | 11/2000 | Jansen et al. | |
| 6,156,046 A | 12/2000 | Passafaro et al. | |
| 6,158,250 A | 12/2000 | Tibbals et al. | |
| 6,159,187 A | 12/2000 | Park et al. | |
| 6,159,225 A | 12/2000 | Makower | |
| 6,161,048 A | 12/2000 | Sluijter et al. | |
| 6,162,184 A | 12/2000 | Swanson et al. | |
| 6,165,163 A | 12/2000 | Chien et al. | |
| 6,165,172 A | 12/2000 | Farley et al. | |
| 6,165,187 A | 12/2000 | Reger et al. | |
| 6,168,594 B1 | 1/2001 | Lafontaine et al. | |
| 6,171,321 B1 | 1/2001 | Gifford, III et al. | |
| 6,179,832 B1 | 1/2001 | Jones et al. | |
| 6,179,835 B1 | 1/2001 | Panescu et al. | |
| 6,179,859 B1 | 1/2001 | Bates et al. | |
| 6,183,468 B1 | 2/2001 | Swanson et al. | |
| 6,183,486 B1 | 2/2001 | Snow et al. | |
| 6,190,379 B1 | 2/2001 | Heuser et al. | |
| 6,191,862 B1 | 2/2001 | Swanson et al. | |
| 6,197,021 B1 | 3/2001 | Panescu et al. | |
| 6,200,266 B1 | 3/2001 | Shokrollahi et al. | |
| 6,203,537 B1 | 3/2001 | Adrian | |
| 6,203,561 B1 | 3/2001 | Ramee et al. | |
| 6,210,406 B1 | 4/2001 | Webster | |
| 6,211,247 B1 | 4/2001 | Goodman | |
| 6,216,044 B1 * | 4/2001 | Kordis | 607/122 |
| 6,216,704 B1 | 4/2001 | Ingle et al. | |
| 6,217,576 B1 | 4/2001 | Tu et al. | |
| 6,219,577 B1 | 4/2001 | Brown, III et al. | |
| 6,228,076 B1 | 5/2001 | Winston et al. | |
| 6,228,109 B1 | 5/2001 | Tu et al. | |
| 6,231,516 B1 | 5/2001 | Keilman et al. | |
| 6,231,587 B1 | 5/2001 | Makower | |
| 6,235,044 B1 | 5/2001 | Root et al. | |
| 6,236,883 B1 | 5/2001 | Ciaccio et al. | |
| 6,237,605 B1 | 5/2001 | Vaska et al. | |
| 6,238,389 B1 | 5/2001 | Paddock et al. | |
| 6,238,392 B1 | 5/2001 | Long | |
| 6,241,666 B1 | 6/2001 | Pomeranz et al. | |
| 6,241,753 B1 | 6/2001 | Knowlton | |
| 6,245,020 B1 | 6/2001 | Moore et al. | |
| 6,245,045 B1 | 6/2001 | Stratienko | |
| 6,248,126 B1 | 6/2001 | Lesser et al. | |
| 6,251,128 B1 | 6/2001 | Knopp et al. | |
| 6,258,087 B1 * | 7/2001 | Edwards et al. | 606/41 |
| 6,273,886 B1 | 8/2001 | Edwards et al. | |
| 6,280,466 B1 | 8/2001 | Kugler et al. | |
| 6,283,935 B1 | 9/2001 | Laufer et al. | |
| 6,283,959 B1 | 9/2001 | Lalonde et al. | |
| 6,284,743 B1 | 9/2001 | Parmacek et al. | |
| 6,287,323 B1 | 9/2001 | Hammerslag | |
| 6,290,696 B1 | 9/2001 | Lafontaine | |
| 6,292,695 B1 | 9/2001 | Webster, Jr. et al. | |
| 6,293,942 B1 | 9/2001 | Goble et al. | |
| 6,293,943 B1 | 9/2001 | Panescu et al. | |
| 6,296,619 B1 | 10/2001 | Brisken et al. | |
| 6,298,256 B1 | 10/2001 | Meyer | |
| 6,299,379 B1 | 10/2001 | Lewis | |
| 6,299,623 B1 | 10/2001 | Wulfman | |
| 6,309,379 B1 | 10/2001 | Willard et al. | |
| 6,309,399 B1 | 10/2001 | Barbut et al. | |
| 6,311,090 B1 | 10/2001 | Knowlton | |
| 6,317,615 B1 | 11/2001 | KenKnight et al. | |
| 6,319,242 B1 | 11/2001 | Patterson et al. | |
| 6,319,251 B1 | 11/2001 | Tu et al. | |
| 6,322,559 B1 | 11/2001 | Daulton et al. | |
| 6,325,797 B1 | 12/2001 | Stewart et al. | |
| 6,325,799 B1 | 12/2001 | Goble | |
| 6,328,699 B1 | 12/2001 | Eigler et al. | |
| 6,346,074 B1 | 2/2002 | Roth | |
| 6,346,104 B2 | 2/2002 | Daly et al. | |
| 6,350,248 B1 | 2/2002 | Knudson et al. | |
| 6,350,276 B1 | 2/2002 | Knowlton | |
| 6,353,751 B1 | 3/2002 | Swanson et al. | |
| 6,355,029 B1 | 3/2002 | Joye et al. | |
| 6,357,447 B1 | 3/2002 | Swanson et al. | |
| 6,361,519 B1 | 3/2002 | Knudson et al. | |
| 6,364,840 B1 | 4/2002 | Crowley | |
| 6,371,965 B2 | 4/2002 | Gifford, III et al. | |
| 6,375,668 B1 | 4/2002 | Gifford et al. | |
| 6,377,854 B1 | 4/2002 | Knowlton | |
| 6,377,855 B1 | 4/2002 | Knowlton | |
| 6,379,352 B1 | 4/2002 | Reynolds et al. | |
| 6,379,373 B1 | 4/2002 | Sawhney et al. | |
| 6,381,497 B1 | 4/2002 | Knowlton | |
| 6,381,498 B1 | 4/2002 | Knowlton | |
| 6,383,151 B1 | 5/2002 | Diederich et al. | |
| 6,387,105 B1 | 5/2002 | Gifford, III et al. | |
| 6,387,380 B1 | 5/2002 | Knowlton | |
| 6,389,311 B1 | 5/2002 | Whayne et al. | |
| 6,389,314 B2 | 5/2002 | Feiring | |
| 6,391,024 B1 | 5/2002 | Sun et al. | |
| 6,394,096 B1 | 5/2002 | Constantz | |
| 6,394,956 B1 | 5/2002 | Chandrasekaran et al. | |
| 6,398,780 B1 | 6/2002 | Farley et al. | |
| 6,398,782 B1 | 6/2002 | Pecor et al. | |
| 6,398,792 B1 | 6/2002 | O'Connor | |
| 6,401,720 B1 | 6/2002 | Stevens et al. | |
| 6,402,719 B1 | 6/2002 | Ponzi et al. | |
| 6,405,090 B1 | 6/2002 | Knowlton | |
| 6,409,723 B1 | 6/2002 | Edwards | |
| 6,413,255 B1 | 7/2002 | Stern | |
| 6,421,559 B1 | 7/2002 | Pearlman | |
| 6,423,057 B1 | 7/2002 | He et al. | |
| 6,425,867 B1 | 7/2002 | Vaezy et al. | |
| 6,425,912 B1 | 7/2002 | Knowlton | |
| 6,427,089 B1 | 7/2002 | Knowlton | |
| 6,427,118 B1 | 7/2002 | Suzuki | |
| 6,428,534 B1 | 8/2002 | Joye et al. | |

(56) References Cited

U.S. PATENT DOCUMENTS

| | | |
|---|---|---|
| 6,428,536 B2 | 8/2002 | Panescu et al. |
| 6,430,446 B1 | 8/2002 | Knowlton |
| 6,432,102 B2 | 8/2002 | Joye et al. |
| 6,436,056 B1 | 8/2002 | Wang et al. |
| 6,438,424 B1 | 8/2002 | Knowlton |
| 6,440,125 B1 | 8/2002 | Rentrop |
| 6,442,413 B1 | 8/2002 | Silver |
| 6,443,965 B1 | 9/2002 | Gifford, III et al. |
| 6,445,939 B1 | 9/2002 | Swanson et al. |
| 6,447,505 B2 | 9/2002 | McGovern et al. |
| 6,447,509 B1 | 9/2002 | Bonnet et al. |
| 6,451,034 B1 | 9/2002 | Gifford, III et al. |
| 6,451,044 B1 | 9/2002 | Naghavi et al. |
| 6,453,202 B1 | 9/2002 | Knowlton |
| 6,454,737 B1 | 9/2002 | Nita et al. |
| 6,454,757 B1 | 9/2002 | Nita et al. |
| 6,454,775 B1 | 9/2002 | Demarais et al. |
| 6,458,098 B1 | 10/2002 | Kanesaka |
| 6,461,378 B1 | 10/2002 | Knowlton |
| 6,468,276 B1 | 10/2002 | McKay |
| 6,468,297 B1 | 10/2002 | Williams et al. |
| 6,470,216 B1 | 10/2002 | Knowlton |
| 6,470,219 B1 | 10/2002 | Edwards et al. |
| 6,471,696 B1 | 10/2002 | Berube et al. |
| 6,475,213 B1 | 11/2002 | Whayne et al. |
| 6,475,215 B1 | 11/2002 | Tanrisever |
| 6,475,238 B1 | 11/2002 | Fedida et al. |
| 6,477,426 B1 | 11/2002 | Fenn et al. |
| 6,480,745 B2 | 11/2002 | Nelson et al. |
| 6,481,704 B1 | 11/2002 | Koster et al. |
| 6,482,202 B1 | 11/2002 | Goble et al. |
| 6,484,052 B1 | 11/2002 | Visuri et al. |
| 6,485,489 B2 | 11/2002 | Teirstein et al. |
| 6,488,679 B1 | 12/2002 | Swanson et al. |
| 6,489,307 B1 | 12/2002 | Phillips et al. |
| 6,491,705 B2 | 12/2002 | Gifford, III et al. |
| 6,494,891 B1 | 12/2002 | Cornish et al. |
| 6,497,711 B1 | 12/2002 | Plaia et al. |
| 6,500,172 B1 | 12/2002 | Panescu et al. |
| 6,500,174 B1 | 12/2002 | Maguire et al. |
| 6,508,765 B2 | 1/2003 | Suorsa et al. |
| 6,508,804 B2 | 1/2003 | Sarge et al. |
| 6,508,815 B1 | 1/2003 | Strul et al. |
| 6,511,478 B1 | 1/2003 | Burnside et al. |
| 6,511,496 B1 | 1/2003 | Huter et al. |
| 6,511,500 B1 | 1/2003 | Rahme |
| 6,514,236 B1 | 2/2003 | Stratienko |
| 6,514,245 B1 | 2/2003 | Williams et al. |
| 6,514,248 B1 | 2/2003 | Eggers et al. |
| 6,517,534 B1 | 2/2003 | McGovern et al. |
| 6,517,572 B2 | 2/2003 | Kugler et al. |
| 6,522,913 B2 | 2/2003 | Panescu et al. |
| 6,522,926 B1 | 2/2003 | Kieval et al. |
| 6,524,274 B1 | 2/2003 | Rosenthal et al. |
| 6,524,299 B1 | 2/2003 | Tran et al. |
| 6,527,765 B2 | 3/2003 | Kelman et al. |
| 6,527,769 B2 | 3/2003 | Langberg et al. |
| 6,540,761 B2 | 4/2003 | Houser |
| 6,542,781 B1 | 4/2003 | Koblish et al. |
| 6,544,780 B1 | 4/2003 | Wang |
| 6,546,272 B1 | 4/2003 | MacKinnon et al. |
| 6,547,788 B1 | 4/2003 | Maguire et al. |
| 6,549,800 B1 | 4/2003 | Atalar et al. |
| 6,552,796 B2 | 4/2003 | Magnin et al. |
| 6,554,780 B1 | 4/2003 | Sampson et al. |
| 6,558,381 B2 | 5/2003 | Ingle et al. |
| 6,558,382 B2 | 5/2003 | Jahns et al. |
| 6,564,096 B2 | 5/2003 | Mest |
| 6,565,582 B2 | 5/2003 | Gifford, III et al. |
| 6,569,109 B2 | 5/2003 | Sakurai et al. |
| 6,569,177 B1 | 5/2003 | Dillard et al. |
| 6,570,659 B2 | 5/2003 | Schmitt |
| 6,572,551 B1 | 6/2003 | Smith et al. |
| 6,572,612 B2 | 6/2003 | Stewart et al. |
| 6,577,902 B1 | 6/2003 | Laufer et al. |
| 6,579,308 B1 | 6/2003 | Jansen et al. |
| 6,579,311 B1 | 6/2003 | Makower |
| 6,582,423 B1 | 6/2003 | Thapliyal et al. |
| 6,589,238 B2 | 7/2003 | Edwards et al. |
| 6,592,526 B1 | 7/2003 | Lenker |
| 6,592,567 B1 | 7/2003 | Levin et al. |
| 6,595,959 B1 | 7/2003 | Stratienko |
| 6,600,956 B2 | 7/2003 | Maschino et al. |
| 6,602,242 B1 | 8/2003 | Fung et al. |
| 6,602,246 B1 | 8/2003 | Joye et al. |
| 6,605,061 B2 | 8/2003 | Vantassel et al. |
| 6,605,084 B2 | 8/2003 | Acker et al. |
| 6,623,452 B2 | 9/2003 | Chien et al. |
| 6,623,453 B1 | 9/2003 | Guibert et al. |
| 6,632,193 B1 | 10/2003 | Davison et al. |
| 6,632,196 B1 | 10/2003 | Houser |
| 6,640,120 B1 * | 10/2003 | Swanson et al. ............... 600/374 |
| 6,645,223 B2 | 11/2003 | Boyle et al. |
| 6,648,854 B1 | 11/2003 | Patterson et al. |
| 6,648,878 B2 | 11/2003 | Lafontaine |
| 6,648,879 B2 | 11/2003 | Joye et al. |
| 6,651,672 B2 | 11/2003 | Roth |
| 6,652,513 B2 | 11/2003 | Panescu et al. |
| 6,652,515 B1 | 11/2003 | Maguire et al. |
| 6,656,136 B1 | 12/2003 | Weng et al. |
| 6,658,279 B2 | 12/2003 | Swanson et al. |
| 6,659,981 B2 | 12/2003 | Stewart et al. |
| 6,666,858 B2 | 12/2003 | Lafontaine |
| 6,666,863 B2 | 12/2003 | Wentzel et al. |
| 6,669,655 B1 | 12/2003 | Acker et al. |
| 6,669,692 B1 | 12/2003 | Nelson et al. |
| 6,673,040 B1 | 1/2004 | Samson et al. |
| 6,673,064 B1 | 1/2004 | Rentrop |
| 6,673,066 B2 | 1/2004 | Werneth |
| 6,673,090 B2 | 1/2004 | Root et al. |
| 6,673,101 B1 | 1/2004 | Fitzgerald et al. |
| 6,673,290 B1 | 1/2004 | Whayne et al. |
| 6,676,678 B2 | 1/2004 | Gifford, III et al. |
| 6,679,268 B2 | 1/2004 | Stevens et al. |
| 6,681,773 B2 | 1/2004 | Murphy et al. |
| 6,682,541 B1 | 1/2004 | Gifford, III et al. |
| 6,684,098 B2 | 1/2004 | Oshio et al. |
| 6,685,732 B2 | 2/2004 | Kramer |
| 6,685,733 B1 | 2/2004 | Dae et al. |
| 6,689,086 B1 | 2/2004 | Nita et al. |
| 6,689,148 B2 | 2/2004 | Sawhney et al. |
| 6,690,181 B1 | 2/2004 | Dowdeswell et al. |
| 6,692,490 B1 | 2/2004 | Edwards |
| 6,695,830 B2 | 2/2004 | Vigil et al. |
| 6,695,857 B2 | 2/2004 | Gifford, III et al. |
| 6,699,241 B2 | 3/2004 | Rappaport et al. |
| 6,699,257 B2 | 3/2004 | Gifford, III et al. |
| 6,702,748 B1 | 3/2004 | Nita et al. |
| 6,702,811 B2 | 3/2004 | Stewart et al. |
| 6,706,010 B1 | 3/2004 | Miki et al. |
| 6,706,011 B1 | 3/2004 | Murphy-Chutorian et al. |
| 6,706,037 B2 | 3/2004 | Zvuloni et al. |
| 6,709,431 B2 | 3/2004 | Lafontaine |
| 6,711,429 B1 | 3/2004 | Gilboa et al. |
| 6,712,815 B2 | 3/2004 | Sampson et al. |
| 6,714,822 B2 | 3/2004 | King et al. |
| 6,716,184 B2 | 4/2004 | Vaezy et al. |
| 6,720,350 B2 | 4/2004 | Kunz et al. |
| 6,723,043 B2 | 4/2004 | Kleeman et al. |
| 6,723,064 B2 | 4/2004 | Babaev |
| 6,736,811 B2 | 5/2004 | Panescu et al. |
| 6,743,184 B2 | 6/2004 | Sampson et al. |
| 6,746,401 B2 | 6/2004 | Panescu |
| 6,746,464 B1 | 6/2004 | Makower |
| 6,746,474 B2 | 6/2004 | Saadat |
| 6,748,953 B2 | 6/2004 | Sherry et al. |
| 6,749,607 B2 | 6/2004 | Edwards et al. |
| 6,752,805 B2 | 6/2004 | Maguire et al. |
| 6,760,616 B2 | 7/2004 | Hoey et al. |
| 6,763,261 B2 | 7/2004 | Casscells, III et al. |
| 6,764,501 B2 | 7/2004 | Ganz |
| 6,769,433 B2 | 8/2004 | Zikorus et al. |
| 6,770,070 B1 | 8/2004 | Balbierz |
| 6,771,996 B2 | 8/2004 | Bowe et al. |

(56) References Cited

U.S. PATENT DOCUMENTS

| | | |
|---|---|---|
| 6,773,433 B2 | 8/2004 | Stewart et al. |
| 6,786,900 B2 | 9/2004 | Joye et al. |
| 6,786,901 B2 | 9/2004 | Joye et al. |
| 6,786,904 B2 | 9/2004 | Döscher et al. |
| 6,788,977 B2 | 9/2004 | Fenn et al. |
| 6,790,206 B2 | 9/2004 | Panescu |
| 6,790,222 B2 | 9/2004 | Kugler et al. |
| 6,796,981 B2 | 9/2004 | Wham et al. |
| 6,797,933 B1 | 9/2004 | Mendis et al. |
| 6,797,960 B1 | 9/2004 | Spartiotis et al. |
| 6,800,075 B2 | 10/2004 | Mische et al. |
| 6,802,857 B1 | 10/2004 | Walsh et al. |
| 6,807,444 B2 | 10/2004 | Tu et al. |
| 6,811,550 B2 | 11/2004 | Holland et al. |
| 6,813,520 B2 | 11/2004 | Truckai et al. |
| 6,814,730 B2 | 11/2004 | Li |
| 6,814,733 B2 | 11/2004 | Leatham et al. |
| 6,823,205 B1 | 11/2004 | Jara |
| 6,824,516 B2 | 11/2004 | Batten et al. |
| 6,827,726 B2 | 12/2004 | Parodi |
| 6,827,926 B2 | 12/2004 | Robinson et al. |
| 6,829,497 B2 | 12/2004 | Mogul |
| 6,830,568 B1 | 12/2004 | Kesten et al. |
| 6,837,886 B2 * | 1/2005 | Collins et al. .................. 606/41 |
| 6,837,888 B2 | 1/2005 | Ciarrocca et al. |
| 6,845,267 B2 | 1/2005 | Harrison et al. |
| 6,847,848 B2 | 1/2005 | Sterzer |
| 6,849,073 B2 | 2/2005 | Hoey et al. |
| 6,849,075 B2 | 2/2005 | Bertolero et al. |
| 6,853,425 B2 | 2/2005 | Kim et al. |
| 6,855,123 B2 | 2/2005 | Nita |
| 6,855,143 B2 | 2/2005 | Davison |
| 6,869,431 B2 | 3/2005 | Maguire et al. |
| 6,872,183 B2 | 3/2005 | Sampson et al. |
| 6,884,260 B2 | 4/2005 | Kugler et al. |
| 6,889,694 B2 | 5/2005 | Hooven |
| 6,893,436 B2 | 5/2005 | Woodard et al. |
| 6,895,077 B2 | 5/2005 | Karellas et al. |
| 6,895,265 B2 | 5/2005 | Silver |
| 6,898,454 B2 | 5/2005 | Atalar et al. |
| 6,899,711 B2 | 5/2005 | Stewart et al. |
| 6,899,718 B2 | 5/2005 | Gifford, III et al. |
| 6,905,494 B2 | 6/2005 | Yon et al. |
| 6,908,462 B2 | 6/2005 | Joye et al. |
| 6,909,009 B2 | 6/2005 | Koridze |
| 6,911,026 B1 | 6/2005 | Hall et al. |
| 6,915,806 B2 | 7/2005 | Pacek et al. |
| 6,923,805 B1 | 8/2005 | LaFontaine et al. |
| 6,926,246 B2 | 8/2005 | Ginggen |
| 6,926,713 B2 | 8/2005 | Rioux et al. |
| 6,926,716 B2 | 8/2005 | Baker et al. |
| 6,929,009 B2 | 8/2005 | Makower et al. |
| 6,929,632 B2 | 8/2005 | Nita et al. |
| 6,929,639 B2 | 8/2005 | Lafontaine |
| 6,932,776 B2 | 8/2005 | Carr |
| 6,936,047 B2 | 8/2005 | Nasab et al. |
| 6,942,620 B2 | 9/2005 | Nita et al. |
| 6,942,657 B2 | 9/2005 | Sinofsky et al. |
| 6,942,677 B2 | 9/2005 | Nita et al. |
| 6,942,692 B2 | 9/2005 | Landau et al. |
| 6,949,097 B2 | 9/2005 | Stewart et al. |
| 6,949,121 B1 | 9/2005 | Laguna |
| 6,952,615 B2 | 10/2005 | Satake |
| 6,953,425 B2 | 10/2005 | Brister |
| 6,955,174 B2 | 10/2005 | Joye et al. |
| 6,955,175 B2 | 10/2005 | Stevens et al. |
| 6,958,075 B2 | 10/2005 | Mon et al. |
| 6,959,711 B2 | 11/2005 | Murphy et al. |
| 6,960,207 B2 | 11/2005 | Vanney et al. |
| 6,962,584 B1 | 11/2005 | Stone et al. |
| 6,964,660 B2 | 11/2005 | Maguire et al. |
| 6,966,908 B2 | 11/2005 | Maguire et al. |
| 6,972,015 B2 | 12/2005 | Joye et al. |
| 6,972,024 B1 | 12/2005 | Kilpatrick et al. |
| 6,974,456 B2 | 12/2005 | Edwards et al. |
| 6,978,174 B2 | 12/2005 | Gelfand et al. |
| 6,979,329 B2 | 12/2005 | Burnside et al. |
| 6,979,420 B2 | 12/2005 | Weber |
| 6,984,238 B2 | 1/2006 | Gifford, III et al. |
| 6,985,774 B2 | 1/2006 | Kieval et al. |
| 6,986,739 B2 | 1/2006 | Warren et al. |
| 6,989,009 B2 | 1/2006 | Lafontaine |
| 6,989,010 B2 | 1/2006 | Francischelli et al. |
| 6,991,617 B2 | 1/2006 | Hektner et al. |
| 7,001,378 B2 | 2/2006 | Yon et al. |
| 7,006,858 B2 | 2/2006 | Silver et al. |
| 7,008,667 B2 | 3/2006 | Chudzik et al. |
| 7,011,508 B2 | 3/2006 | Lum |
| 7,022,105 B1 | 4/2006 | Edwards |
| 7,022,120 B2 | 4/2006 | Lafontaine |
| 7,025,767 B2 | 4/2006 | Schaefer et al. |
| 7,033,322 B2 | 4/2006 | Silver |
| 7,033,372 B1 | 4/2006 | Cahalan |
| 7,041,098 B2 | 5/2006 | Farley et al. |
| 7,050,848 B2 | 5/2006 | Hoey et al. |
| 7,063,670 B2 | 6/2006 | Sampson et al. |
| 7,063,679 B2 | 6/2006 | Maguire et al. |
| 7,063,719 B2 | 6/2006 | Jansen et al. |
| 7,066,895 B2 | 6/2006 | Podany |
| 7,066,900 B2 | 6/2006 | Botto et al. |
| 7,066,904 B2 | 6/2006 | Rosenthal et al. |
| 7,072,720 B2 | 7/2006 | Puskas |
| 7,074,217 B2 | 7/2006 | Strul et al. |
| 7,081,112 B2 | 7/2006 | Joye et al. |
| 7,081,114 B2 | 7/2006 | Rashidi |
| 7,083,614 B2 | 8/2006 | Fjield et al. |
| 7,084,276 B2 | 8/2006 | Vu et al. |
| 7,087,026 B2 | 8/2006 | Callister et al. |
| 7,087,051 B2 | 8/2006 | Bourne et al. |
| 7,087,052 B2 | 8/2006 | Sampson et al. |
| 7,087,053 B2 | 8/2006 | Vanney |
| 7,089,065 B2 | 8/2006 | Westlund et al. |
| 7,097,641 B1 | 8/2006 | Arless et al. |
| 7,100,614 B2 | 9/2006 | Stevens et al. |
| 7,101,368 B2 | 9/2006 | Lafontaine |
| 7,104,983 B2 | 9/2006 | Grasso, III et al. |
| 7,104,987 B2 | 9/2006 | Biggs et al. |
| 7,108,715 B2 | 9/2006 | Lawrence-Brown et al. |
| 7,112,196 B2 | 9/2006 | Brosch et al. |
| 7,112,198 B2 | 9/2006 | Satake |
| 7,112,211 B2 | 9/2006 | Gifford, III et al. |
| 7,122,019 B1 | 10/2006 | Kesten et al. |
| 7,122,033 B2 | 10/2006 | Wood |
| 7,134,438 B2 | 11/2006 | Makower et al. |
| 7,137,963 B2 | 11/2006 | Nita et al. |
| 7,137,980 B2 | 11/2006 | Buysse et al. |
| 7,153,315 B2 | 12/2006 | Miller |
| 7,155,271 B2 | 12/2006 | Halperin et al. |
| 7,157,491 B2 | 1/2007 | Mewshaw et al. |
| 7,157,492 B2 | 1/2007 | Mewshaw et al. |
| 7,158,832 B2 | 1/2007 | Kieval et al. |
| 7,160,296 B2 | 1/2007 | Pearson et al. |
| 7,162,303 B2 | 1/2007 | Levin et al. |
| 7,165,551 B2 | 1/2007 | Edwards et al. |
| 7,169,144 B2 | 1/2007 | Hoey et al. |
| 7,172,589 B2 | 2/2007 | Lafontaine |
| 7,172,610 B2 | 2/2007 | Heitzmann et al. |
| 7,181,261 B2 | 2/2007 | Silver et al. |
| 7,184,811 B2 | 2/2007 | Phan et al. |
| 7,184,827 B1 | 2/2007 | Edwards |
| 7,189,227 B2 | 3/2007 | Lafontaine |
| 7,192,427 B2 | 3/2007 | Chapelon et al. |
| 7,192,586 B2 | 3/2007 | Bander |
| 7,197,354 B2 | 3/2007 | Sobe |
| 7,198,632 B2 | 4/2007 | Lim et al. |
| 7,200,445 B1 | 4/2007 | Dalbec et al. |
| 7,201,749 B2 | 4/2007 | Govari et al. |
| 7,203,537 B2 | 4/2007 | Mower |
| 7,214,234 B2 | 5/2007 | Rapacki et al. |
| 7,220,233 B2 | 5/2007 | Nita et al. |
| 7,220,239 B2 | 5/2007 | Wilson et al. |
| 7,220,257 B1 | 5/2007 | Lafontaine |
| 7,220,270 B2 | 5/2007 | Sawhney et al. |
| 7,232,458 B2 | 6/2007 | Saadat |

(56) References Cited

U.S. PATENT DOCUMENTS

| | | |
|---|---|---|
| 7,232,459 B2 | 6/2007 | Greenberg et al. |
| 7,238,184 B2 | 7/2007 | Megerman et al. |
| 7,241,273 B2 | 7/2007 | Maguire et al. |
| 7,241,736 B2 | 7/2007 | Hunter et al. |
| 7,247,141 B2 | 7/2007 | Makin et al. |
| 7,250,041 B2 | 7/2007 | Chiu et al. |
| 7,250,440 B2 | 7/2007 | Mewshaw et al. |
| 7,252,664 B2 | 8/2007 | Nasab et al. |
| 7,252,679 B2 | 8/2007 | Fischell et al. |
| 7,264,619 B2 | 9/2007 | Venturelli |
| 7,279,600 B2 | 10/2007 | Mewshaw et al. |
| 7,280,863 B2 | 10/2007 | Shachar |
| 7,282,213 B2 | 10/2007 | Schroeder et al. |
| 7,285,119 B2 | 10/2007 | Stewart et al. |
| 7,285,120 B2 | 10/2007 | Im et al. |
| 7,288,089 B2 | 10/2007 | Yon et al. |
| 7,288,096 B2 | 10/2007 | Chin |
| 7,291,146 B2 | 11/2007 | Steinke et al. |
| 7,293,562 B2 | 11/2007 | Malecki et al. |
| 7,294,125 B2 | 11/2007 | Phalen et al. |
| 7,294,126 B2 | 11/2007 | Sampson et al. |
| 7,294,127 B2 | 11/2007 | Leung et al. |
| 7,297,131 B2 | 11/2007 | Nita |
| 7,297,475 B2 | 11/2007 | Koiwai et al. |
| 7,300,433 B2 | 11/2007 | Lane et al. |
| 7,301,108 B2 | 11/2007 | Egitto et al. |
| 7,310,150 B2 | 12/2007 | Guillermo et al. |
| 7,313,430 B2 | 12/2007 | Urquhart et al. |
| 7,314,483 B2 | 1/2008 | Landau et al. |
| 7,317,077 B2 | 1/2008 | Averback et al. |
| 7,323,006 B2 | 1/2008 | Andreas et al. |
| 7,326,206 B2 | 2/2008 | Paul et al. |
| 7,326,226 B2 | 2/2008 | Root et al. |
| 7,326,235 B2 | 2/2008 | Edwards |
| 7,326,237 B2 | 2/2008 | DePalma et al. |
| 7,329,236 B2 | 2/2008 | Kesten et al. |
| 7,335,180 B2 | 2/2008 | Nita et al. |
| 7,335,192 B2 | 2/2008 | Keren et al. |
| 7,338,467 B2 | 3/2008 | Lutter |
| 7,341,570 B2 | 3/2008 | Keren et al. |
| 7,343,195 B2 | 3/2008 | Strommer et al. |
| 7,347,857 B2 | 3/2008 | Anderson et al. |
| 7,348,003 B2 | 3/2008 | Salcedo et al. |
| 7,352,593 B2 | 4/2008 | Zeng et al. |
| 7,354,927 B2 | 4/2008 | Vu |
| 7,359,732 B2 | 4/2008 | Kim et al. |
| 7,361,341 B2 | 4/2008 | Salcedo et al. |
| 7,364,566 B2 | 4/2008 | Elkins et al. |
| 7,367,970 B2 | 5/2008 | Govari et al. |
| 7,367,975 B2 | 5/2008 | Malecki et al. |
| 7,371,231 B2 | 5/2008 | Rioux et al. |
| 7,387,126 B2 | 6/2008 | Cox et al. |
| 7,393,338 B2 | 7/2008 | Nita |
| 7,396,355 B2 | 7/2008 | Goldman et al. |
| 7,402,151 B2 | 7/2008 | Rosenman et al. |
| 7,402,312 B2 | 7/2008 | Rosen et al. |
| 7,404,824 B1 | 7/2008 | Webler et al. |
| 7,406,970 B2 | 8/2008 | Zikorus et al. |
| 7,407,502 B2 | 8/2008 | Strul et al. |
| 7,407,506 B2 | 8/2008 | Makower |
| 7,407,671 B2 | 8/2008 | McBride et al. |
| 7,408,021 B2 | 8/2008 | Averback et al. |
| 7,410,486 B2 | 8/2008 | Fuimaono et al. |
| 7,413,556 B2 | 8/2008 | Zhang et al. |
| 7,425,212 B1 | 9/2008 | Danek et al. |
| 7,426,409 B2 | 9/2008 | Casscells, III et al. |
| 7,435,248 B2 | 10/2008 | Taimisto et al. |
| 7,447,453 B2 | 11/2008 | Kim et al. |
| 7,449,018 B2 | 11/2008 | Kramer |
| 7,452,538 B2 | 11/2008 | Ni et al. |
| 7,473,890 B2 | 1/2009 | Grier et al. |
| 7,476,384 B2 | 1/2009 | Ni et al. |
| 7,479,157 B2 | 1/2009 | Weber et al. |
| 7,481,803 B2 | 1/2009 | Kesten et al. |
| 7,485,104 B2 | 2/2009 | Kieval |
| 7,486,805 B2 | 2/2009 | Krattiger |
| 7,487,780 B2 | 2/2009 | Hooven |
| 7,493,154 B2 | 2/2009 | Bonner et al. |
| 7,494,485 B2 | 2/2009 | Beck et al. |
| 7,494,486 B2 | 2/2009 | Mische et al. |
| 7,494,488 B2 | 2/2009 | Weber |
| 7,494,661 B2 | 2/2009 | Sanders |
| 7,495,439 B2 | 2/2009 | Wiggins |
| 7,497,858 B2 | 3/2009 | Chapelon et al. |
| 7,499,745 B2 | 3/2009 | Littrup et al. |
| 7,500,985 B2 | 3/2009 | Saadat |
| 7,505,812 B1 | 3/2009 | Eggers et al. |
| 7,505,816 B2 | 3/2009 | Schmeling et al. |
| 7,507,233 B2 | 3/2009 | Littrup et al. |
| 7,507,235 B2 | 3/2009 | Keogh et al. |
| 7,511,494 B2 | 3/2009 | Wedeen |
| 7,512,445 B2 | 3/2009 | Truckai et al. |
| 7,527,643 B2 | 5/2009 | Case et al. |
| 7,529,589 B2 | 5/2009 | Williams et al. |
| 7,540,852 B2 | 6/2009 | Nita et al. |
| 7,540,870 B2 | 6/2009 | Babaev |
| RE40,863 E | 7/2009 | Tay et al. |
| 7,556,624 B2 | 7/2009 | Laufer et al. |
| 7,558,625 B2 | 7/2009 | Levin et al. |
| 7,563,247 B2 | 7/2009 | Maguire et al. |
| 7,566,319 B2 | 7/2009 | McAuley et al. |
| 7,569,052 B2 | 8/2009 | Phan et al. |
| 7,582,111 B2 | 9/2009 | Krolik et al. |
| 7,584,004 B2 | 9/2009 | Caparso et al. |
| 7,585,835 B2 | 9/2009 | Hill et al. |
| 7,591,996 B2 | 9/2009 | Hwang et al. |
| 7,597,704 B2 | 10/2009 | Frazier et al. |
| 7,598,228 B2 | 10/2009 | Hattori et al. |
| 7,599,730 B2 | 10/2009 | Hunter et al. |
| 7,603,166 B2 | 10/2009 | Casscells, III et al. |
| 7,604,608 B2 | 10/2009 | Nita et al. |
| 7,604,633 B2 | 10/2009 | Truckai et al. |
| 7,615,015 B2 | 11/2009 | Coleman |
| 7,615,072 B2 | 11/2009 | Rust et al. |
| 7,617,005 B2 | 11/2009 | Demarais et al. |
| 7,620,451 B2 | 11/2009 | Demarais et al. |
| 7,621,902 B2 | 11/2009 | Nita et al. |
| 7,621,929 B2 | 11/2009 | Nita et al. |
| 7,626,015 B2 | 12/2009 | Feinstein et al. |
| 7,626,235 B2 | 12/2009 | Kinoshita |
| 7,632,268 B2 | 12/2009 | Edwards et al. |
| 7,632,845 B2 | 12/2009 | Vu et al. |
| 7,635,383 B2 | 12/2009 | Gumm |
| 7,640,046 B2 | 12/2009 | Pastore et al. |
| 7,641,633 B2 | 1/2010 | Laufer et al. |
| 7,641,679 B2 | 1/2010 | Joye et al. |
| 7,646,544 B2 | 1/2010 | Batchko et al. |
| 7,647,115 B2 | 1/2010 | Levin et al. |
| 7,653,438 B2 | 1/2010 | Deem et al. |
| 7,655,006 B2 | 2/2010 | Sauvageau et al. |
| 7,662,114 B2 | 2/2010 | Seip et al. |
| 7,664,548 B2 | 2/2010 | Amurthur et al. |
| 7,670,279 B2 | 3/2010 | Gertner |
| 7,670,335 B2 | 3/2010 | Keidar |
| 7,671,084 B2 | 3/2010 | Mewshaw et al. |
| 7,678,104 B2 | 3/2010 | Keidar |
| 7,678,106 B2 | 3/2010 | Lee |
| 7,678,108 B2 | 3/2010 | Christian et al. |
| 7,691,080 B2 | 4/2010 | Seward et al. |
| 7,699,809 B2 | 4/2010 | Urmey |
| 7,706,882 B2 | 4/2010 | Francischelli et al. |
| 7,715,912 B2 | 5/2010 | Rezai et al. |
| 7,717,853 B2 | 5/2010 | Nita |
| 7,717,909 B2 | 5/2010 | Strul et al. |
| 7,717,948 B2 | 5/2010 | Demarais et al. |
| 7,722,539 B2 | 5/2010 | Carter et al. |
| 7,725,157 B2 | 5/2010 | Dumoulin et al. |
| 7,727,178 B2 | 6/2010 | Wilson et al. |
| 7,736,317 B2 | 6/2010 | Stephens et al. |
| 7,736,360 B2 | 6/2010 | Mody et al. |
| 7,736,362 B2 | 6/2010 | Eberl et al. |
| 7,738,952 B2 | 6/2010 | Yun et al. |
| 7,740,629 B2 | 6/2010 | Anderson et al. |
| 7,741,299 B2 | 6/2010 | Feinstein et al. |

(56) References Cited

U.S. PATENT DOCUMENTS

| | | |
|---|---|---|
| 7,742,795 B2 | 6/2010 | Stone et al. |
| 7,744,594 B2 | 6/2010 | Yamazaki et al. |
| 7,753,907 B2 | 7/2010 | DiMatteo et al. |
| 7,756,583 B2 | 7/2010 | Demarais et al. |
| 7,758,510 B2 | 7/2010 | Nita et al. |
| 7,758,520 B2 | 7/2010 | Griffin et al. |
| 7,759,315 B2 | 7/2010 | Cuzzocrea et al. |
| 7,766,833 B2 | 8/2010 | Lee et al. |
| 7,766,878 B2 | 8/2010 | Tremaglio, Jr. et al. |
| 7,766,892 B2 | 8/2010 | Keren et al. |
| 7,767,844 B2 | 8/2010 | Lee et al. |
| 7,769,427 B2 | 8/2010 | Shachar |
| 7,771,372 B2 | 8/2010 | Wilson |
| 7,771,421 B2 | 8/2010 | Stewart et al. |
| 7,776,967 B2 | 8/2010 | Perry et al. |
| 7,777,486 B2 | 8/2010 | Hargreaves et al. |
| 7,780,660 B2 | 8/2010 | Bourne et al. |
| 7,789,876 B2 | 9/2010 | Zikorus et al. |
| 7,792,568 B2 | 9/2010 | Zhong et al. |
| 7,799,021 B2 | 9/2010 | Leung et al. |
| 7,803,168 B2 | 9/2010 | Gifford et al. |
| 7,806,871 B2 | 10/2010 | Li et al. |
| 7,811,265 B2 | 10/2010 | Hering et al. |
| 7,811,281 B1 | 10/2010 | Rentrop |
| 7,811,313 B2 | 10/2010 | Mon et al. |
| 7,816,511 B2 | 10/2010 | Kawashima et al. |
| 7,818,053 B2 | 10/2010 | Kassab |
| 7,819,866 B2 | 10/2010 | Bednarek |
| 7,822,460 B2 | 10/2010 | Halperin et al. |
| 7,828,837 B2 | 11/2010 | Khoury |
| 7,832,407 B2 | 11/2010 | Gertner |
| 7,833,220 B2 | 11/2010 | Mon et al. |
| 7,837,676 B2 | 11/2010 | Sinelnikov et al. |
| 7,837,720 B2 | 11/2010 | Mon |
| 7,841,978 B2 | 11/2010 | Gertner |
| 7,846,157 B2 | 12/2010 | Kozel |
| 7,846,160 B2 | 12/2010 | Payne et al. |
| 7,846,172 B2 | 12/2010 | Makower |
| 7,849,860 B2 | 12/2010 | Makower et al. |
| 7,850,685 B2 | 12/2010 | Kunis et al. |
| 7,853,333 B2 | 12/2010 | Demarais |
| 7,854,734 B2 | 12/2010 | Biggs et al. |
| 7,857,756 B2 | 12/2010 | Warren et al. |
| 7,862,565 B2 | 1/2011 | Eder et al. |
| 7,863,897 B2 | 1/2011 | Slocum, Jr. et al. |
| 7,869,854 B2 | 1/2011 | Shachar et al. |
| 7,873,417 B2 | 1/2011 | Demarais et al. |
| 7,887,538 B2 | 2/2011 | Bleich et al. |
| 7,894,905 B2 | 2/2011 | Pless et al. |
| 7,896,873 B2 | 3/2011 | Hiller et al. |
| 7,901,400 B2 | 3/2011 | Wham et al. |
| 7,901,402 B2 | 3/2011 | Jones et al. |
| 7,901,420 B2 | 3/2011 | Dunn |
| 7,905,862 B2 | 3/2011 | Sampson |
| 7,918,850 B2 | 4/2011 | Govari et al. |
| 7,927,370 B2 | 4/2011 | Webler et al. |
| 7,937,143 B2 | 5/2011 | Demarais et al. |
| 7,938,830 B2 | 5/2011 | Saadat et al. |
| 7,942,874 B2 | 5/2011 | Eder et al. |
| 7,942,928 B2 | 5/2011 | Webler et al. |
| 7,946,976 B2 | 5/2011 | Gertner |
| 7,950,397 B2 | 5/2011 | Thapliyal et al. |
| 7,955,293 B2 | 6/2011 | Nita et al. |
| 7,956,613 B2 | 6/2011 | Wald |
| 7,959,627 B2 | 6/2011 | Utley et al. |
| 7,962,854 B2 | 6/2011 | Vance et al. |
| 7,967,782 B2 | 6/2011 | Laufer et al. |
| 7,967,808 B2 | 6/2011 | Fitzgerald et al. |
| 7,972,327 B2 | 7/2011 | Eberl et al. |
| 7,972,330 B2 | 7/2011 | Alejandro et al. |
| 7,983,751 B2 | 7/2011 | Zdeblick et al. |
| 8,001,976 B2 | 8/2011 | Gertner |
| 8,007,440 B2 | 8/2011 | Magnin et al. |
| 8,012,147 B2 | 9/2011 | Lafontaine |
| 8,019,435 B2 | 9/2011 | Hastings et al. |
| 8,021,362 B2 | 9/2011 | Deem et al. |
| 8,021,413 B2 | 9/2011 | Dierking et al. |
| 8,025,661 B2 | 9/2011 | Arnold et al. |
| 8,027,718 B2 | 9/2011 | Spinner et al. |
| 8,031,927 B2 | 10/2011 | Karl et al. |
| 8,033,284 B2 | 10/2011 | Porter et al. |
| 8,048,144 B2 | 11/2011 | Thistle et al. |
| 8,052,636 B2 | 11/2011 | Moll et al. |
| 8,052,700 B2 | 11/2011 | Dunn |
| 8,062,289 B2 | 11/2011 | Babaev |
| 8,075,580 B2 | 12/2011 | Makower |
| 8,080,006 B2 | 12/2011 | Lafontaine et al. |
| 8,088,127 B2 | 1/2012 | Mayse et al. |
| 8,116,883 B2 | 2/2012 | Williams et al. |
| 8,119,183 B2 | 2/2012 | O'Donoghue et al. |
| 8,120,518 B2 | 2/2012 | Jang et al. |
| 8,123,741 B2 | 2/2012 | Marrouche et al. |
| 8,128,617 B2 | 3/2012 | Bencini et al. |
| 8,131,371 B2 | 3/2012 | Demarals et al. |
| 8,131,372 B2 | 3/2012 | Levin et al. |
| 8,131,382 B2 | 3/2012 | Asada |
| 8,137,274 B2 | 3/2012 | Weng et al. |
| 8,140,170 B2 | 3/2012 | Rezai et al. |
| 8,143,316 B2 | 3/2012 | Ueno |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,152,830 B2 | 4/2012 | Gumm |
| 8,162,933 B2 | 4/2012 | Francischelli et al. |
| 8,175,711 B2 | 5/2012 | Demarais et al. |
| 8,187,261 B2 | 5/2012 | Watson |
| 8,190,238 B2 | 5/2012 | Moll et al. |
| 8,192,053 B2 | 6/2012 | Owen et al. |
| 8,198,611 B2 | 6/2012 | LaFontaine et al. |
| 8,214,056 B2 | 7/2012 | Hoffer et al. |
| 8,221,407 B2 | 7/2012 | Phan et al. |
| 8,226,637 B2 | 7/2012 | Satake |
| 8,231,617 B2 | 7/2012 | Satake |
| 8,241,217 B2 | 8/2012 | Chiang et al. |
| 8,257,724 B2 | 9/2012 | Cromack et al. |
| 8,257,725 B2 | 9/2012 | Cromack et al. |
| 8,260,397 B2 | 9/2012 | Ruff et al. |
| 8,263,104 B2 | 9/2012 | Ho et al. |
| 8,273,023 B2 | 9/2012 | Razavi |
| 8,277,379 B2 | 10/2012 | Lau et al. |
| 8,287,524 B2 | 10/2012 | Siegel |
| 8,287,532 B2 | 10/2012 | Carroll et al. |
| 8,292,881 B2 | 10/2012 | Brannan et al. |
| 8,293,703 B2 | 10/2012 | Averback et al. |
| 8,295,902 B2 | 10/2012 | Salahieh et al. |
| 8,295,912 B2 | 10/2012 | Gertner |
| 8,308,722 B2 | 11/2012 | Ormsby et al. |
| 8,317,776 B2 | 11/2012 | Ferren et al. |
| 8,317,810 B2 | 11/2012 | Stangenes et al. |
| 8,329,179 B2 | 12/2012 | Ni et al. |
| 8,336,705 B2 | 12/2012 | Okahisa |
| 8,343,031 B2 | 1/2013 | Gertner |
| 8,343,145 B2 | 1/2013 | Brannan |
| 8,347,891 B2 | 1/2013 | Demarais et al. |
| 8,353,945 B2 | 1/2013 | Andreas et al. |
| 8,364,237 B2 | 1/2013 | Stone et al. |
| 8,366,615 B2 | 2/2013 | Razavi |
| 8,382,697 B2 | 2/2013 | Brenneman et al. |
| 8,388,680 B2 | 3/2013 | Starksen et al. |
| 8,396,548 B2 | 3/2013 | Perry et al. |
| 8,398,629 B2 | 3/2013 | Thistle |
| 8,401,667 B2 | 3/2013 | Gustus et al. |
| 8,403,881 B2 | 3/2013 | Ferren et al. |
| 8,406,877 B2 | 3/2013 | Smith et al. |
| 8,409,172 B2 | 4/2013 | Moll et al. |
| 8,409,193 B2 | 4/2013 | Young et al. |
| 8,409,195 B2 | 4/2013 | Young |
| 8,418,362 B2 | 4/2013 | Zerfas et al. |
| 8,452,988 B2 | 5/2013 | Wang |
| 8,454,594 B2 | 6/2013 | Demarais et al. |
| 8,460,358 B2 | 6/2013 | Andreas et al. |
| 8,465,452 B2 | 6/2013 | Kassab |

(56) References Cited

U.S. PATENT DOCUMENTS

| | | |
|---|---|---|
| 8,469,919 B2 | 6/2013 | Ingle et al. |
| 8,473,067 B2 | 6/2013 | Hastings et al. |
| 8,480,663 B2 | 7/2013 | Ingle et al. |
| 8,485,992 B2 | 7/2013 | Griffin et al. |
| 8,486,060 B2 | 7/2013 | Kotmel et al. |
| 8,486,063 B2 | 7/2013 | Werneth et al. |
| 8,488,591 B2 | 7/2013 | Miali et al. |
| 2001/0007070 A1 | 7/2001 | Stewart et al. |
| 2001/0039419 A1 | 11/2001 | Francischelli et al. |
| 2001/0051774 A1 | 12/2001 | Littrup et al. |
| 2002/0022864 A1 | 2/2002 | Mahvi et al. |
| 2002/0042639 A1 | 4/2002 | Murphy-Chutorian et al. |
| 2002/0045811 A1 | 4/2002 | Kittrell et al. |
| 2002/0045890 A1 | 4/2002 | Celliers et al. |
| 2002/0062123 A1 | 5/2002 | McClurken et al. |
| 2002/0062146 A1 | 5/2002 | Makower et al. |
| 2002/0065542 A1 | 5/2002 | Lax et al. |
| 2002/0072686 A1 | 6/2002 | Hoey et al. |
| 2002/0077592 A1 | 6/2002 | Barry |
| 2002/0082552 A1 | 6/2002 | Ding et al. |
| 2002/0087151 A1 | 7/2002 | Mody et al. |
| 2002/0087156 A1 | 7/2002 | Maguire et al. |
| 2002/0091381 A1 | 7/2002 | Edwards |
| 2002/0095197 A1 | 7/2002 | Lardo et al. |
| 2002/0107511 A1 | 8/2002 | Collins et al. |
| 2002/0107536 A1 | 8/2002 | Hussein |
| 2002/0143324 A1 | 10/2002 | Edwards |
| 2002/0147480 A1 | 10/2002 | Mamayek |
| 2002/0169444 A1 | 11/2002 | Mest et al. |
| 2002/0198520 A1 | 12/2002 | Coen et al. |
| 2003/0004510 A1 | 1/2003 | Wham et al. |
| 2003/0028114 A1 | 2/2003 | Casscells, III et al. |
| 2003/0050635 A1 | 3/2003 | Truckai et al. |
| 2003/0060857 A1 | 3/2003 | Perrson et al. |
| 2003/0060858 A1 | 3/2003 | Kieval et al. |
| 2003/0065317 A1 | 4/2003 | Rudie et al. |
| 2003/0069619 A1 | 4/2003 | Fenn et al. |
| 2003/0088189 A1 | 5/2003 | Tu et al. |
| 2003/0092995 A1 | 5/2003 | Thompson |
| 2003/0114791 A1 | 6/2003 | Rosenthal et al. |
| 2003/0139689 A1 | 7/2003 | Shturman et al. |
| 2003/0195501 A1 | 10/2003 | Sherman et al. |
| 2003/0199747 A1 | 10/2003 | Michlitsch et al. |
| 2003/0212394 A1 | 11/2003 | Pearson et al. |
| 2003/0220639 A1 | 11/2003 | Chapelon et al. |
| 2003/0229340 A1 | 12/2003 | Sherry et al. |
| 2003/0229384 A1 | 12/2003 | Mon |
| 2004/0000633 A1 | 1/2004 | Casper et al. |
| 2004/0006359 A1 | 1/2004 | Laguna |
| 2004/0010118 A1 | 1/2004 | Zerhusen et al. |
| 2004/0019348 A1 | 1/2004 | Stevens et al. |
| 2004/0024371 A1 | 2/2004 | Plicchi et al. |
| 2004/0043030 A1 | 3/2004 | Griffiths et al. |
| 2004/0062852 A1 | 4/2004 | Schroeder et al. |
| 2004/0064090 A1 | 4/2004 | Keren et al. |
| 2004/0064093 A1 | 4/2004 | Hektner et al. |
| 2004/0073206 A1 | 4/2004 | Foley et al. |
| 2004/0088002 A1 | 5/2004 | Boyle et al. |
| 2004/0093055 A1 | 5/2004 | Bartorelli et al. |
| 2004/0106871 A1 | 6/2004 | Hunyor et al. |
| 2004/0111016 A1 | 6/2004 | Casscells, III et al. |
| 2004/0117032 A1 | 6/2004 | Roth |
| 2004/0122421 A1 | 6/2004 | Wood |
| 2004/0147915 A1 | 7/2004 | Hasebe |
| 2004/0162555 A1 | 8/2004 | Farley et al. |
| 2004/0167506 A1 | 8/2004 | Chen |
| 2004/0181165 A1 | 9/2004 | Hoey et al. |
| 2004/0186356 A1 | 9/2004 | O'Malley et al. |
| 2004/0186468 A1 | 9/2004 | Edwards |
| 2004/0187875 A1 | 9/2004 | He et al. |
| 2004/0193211 A1 | 9/2004 | Voegele et al. |
| 2004/0220556 A1 | 11/2004 | Cooper et al. |
| 2004/0243022 A1 | 12/2004 | Carney et al. |
| 2004/0243199 A1 | 12/2004 | Mon et al. |
| 2004/0253304 A1 | 12/2004 | Gross et al. |
| 2004/0267250 A1 | 12/2004 | Yon et al. |
| 2005/0010095 A1 | 1/2005 | Stewart et al. |
| 2005/0010208 A1 | 1/2005 | Winston et al. |
| 2005/0015125 A1 | 1/2005 | Mioduski et al. |
| 2005/0033136 A1 | 2/2005 | Govari et al. |
| 2005/0080374 A1 | 4/2005 | Esch et al. |
| 2005/0090820 A1 | 4/2005 | Cornelius et al. |
| 2005/0096647 A1 | 5/2005 | Steinke et al. |
| 2005/0129616 A1 | 6/2005 | Salcedo et al. |
| 2005/0137180 A1 | 6/2005 | Robinson et al. |
| 2005/0143817 A1 | 6/2005 | Hunter et al. |
| 2005/0148842 A1 | 7/2005 | Wang et al. |
| 2005/0149069 A1 | 7/2005 | Bertolero et al. |
| 2005/0149080 A1 | 7/2005 | Hunter et al. |
| 2005/0149158 A1 | 7/2005 | Hunter et al. |
| 2005/0149173 A1 | 7/2005 | Hunter et al. |
| 2005/0149175 A1 | 7/2005 | Hunter et al. |
| 2005/0154277 A1 | 7/2005 | Tang et al. |
| 2005/0154445 A1 | 7/2005 | Hunter et al. |
| 2005/0154453 A1 | 7/2005 | Hunter et al. |
| 2005/0154454 A1 | 7/2005 | Hunter et al. |
| 2005/0165389 A1 | 7/2005 | Swain et al. |
| 2005/0165391 A1 | 7/2005 | Maguire et al. |
| 2005/0165467 A1 | 7/2005 | Hunter et al. |
| 2005/0165488 A1 | 7/2005 | Hunter et al. |
| 2005/0175661 A1 | 8/2005 | Hunter et al. |
| 2005/0175662 A1 | 8/2005 | Hunter et al. |
| 2005/0175663 A1 | 8/2005 | Hunter et al. |
| 2005/0177103 A1 | 8/2005 | Hunter et al. |
| 2005/0177225 A1 | 8/2005 | Hunter et al. |
| 2005/0181004 A1 | 8/2005 | Hunter et al. |
| 2005/0181008 A1 | 8/2005 | Hunter et al. |
| 2005/0181011 A1 | 8/2005 | Hunter et al. |
| 2005/0181977 A1 | 8/2005 | Hunter et al. |
| 2005/0182479 A1 | 8/2005 | Bonsignore et al. |
| 2005/0183728 A1 | 8/2005 | Hunter et al. |
| 2005/0186242 A1 | 8/2005 | Hunter et al. |
| 2005/0186243 A1 | 8/2005 | Hunter et al. |
| 2005/0191331 A1 | 9/2005 | Hunter et al. |
| 2005/0203410 A1 | 9/2005 | Jenkins |
| 2005/0203434 A1 | 9/2005 | Kassab |
| 2005/0203498 A1 | 9/2005 | Mon et al. |
| 2005/0209587 A1 | 9/2005 | Joye et al. |
| 2005/0214205 A1 | 9/2005 | Salcedo et al. |
| 2005/0214207 A1 | 9/2005 | Salcedo et al. |
| 2005/0214208 A1 | 9/2005 | Salcedo et al. |
| 2005/0214209 A1 | 9/2005 | Salcedo et al. |
| 2005/0214210 A1 | 9/2005 | Salcedo et al. |
| 2005/0214268 A1 | 9/2005 | Cavanagh et al. |
| 2005/0228286 A1 | 10/2005 | Messerly et al. |
| 2005/0228415 A1 | 10/2005 | Gertner |
| 2005/0228460 A1 | 10/2005 | Levin et al. |
| 2005/0232921 A1 | 10/2005 | Rosen et al. |
| 2005/0234312 A1 | 10/2005 | Suzuki et al. |
| 2005/0245862 A1 | 11/2005 | Seward |
| 2005/0251116 A1 | 11/2005 | Steinke et al. |
| 2005/0252553 A1 | 11/2005 | Ginggen |
| 2005/0256398 A1 | 11/2005 | Hastings et al. |
| 2005/0267556 A1 | 12/2005 | Shuros et al. |
| 2005/0283195 A1 | 12/2005 | Pastore et al. |
| 2006/0004323 A1 | 1/2006 | Chang et al. |
| 2006/0018949 A1 | 1/2006 | Ammon et al. |
| 2006/0024564 A1 | 2/2006 | Manclaw |
| 2006/0025765 A1 | 2/2006 | Landman et al. |
| 2006/0062786 A1 | 3/2006 | Salcedo et al. |
| 2006/0083194 A1 | 4/2006 | Dhrimaj et al. |
| 2006/0085054 A1 | 4/2006 | Zikorus et al. |
| 2006/0089637 A1 | 4/2006 | Werneth et al. |
| 2006/0089638 A1 | 4/2006 | Carmel et al. |
| 2006/0095096 A1 | 5/2006 | DeBenedictis et al. |
| 2006/0106375 A1 | 5/2006 | Werneth et al. |
| 2006/0142790 A1 | 6/2006 | Gertner |
| 2006/0147492 A1 | 7/2006 | Hunter et al. |
| 2006/0149166 A1 | 7/2006 | Zvuloni |
| 2006/0167106 A1 | 7/2006 | Zhang et al. |
| 2006/0167498 A1 | 7/2006 | DiLorenzo |
| 2006/0171895 A1 | 8/2006 | Bucay-Couto |
| 2006/0184060 A1 | 8/2006 | Belalcazar et al. |
| 2006/0184221 A1 | 8/2006 | Stewart et al. |

(56) References Cited

U.S. PATENT DOCUMENTS

| | | |
|---|---|---|
| 2006/0195139 A1 | 8/2006 | Gertner |
| 2006/0206150 A1 | 9/2006 | Demarais et al. |
| 2006/0224153 A1 | 10/2006 | Fischell et al. |
| 2006/0235286 A1 | 10/2006 | Stone et al. |
| 2006/0239921 A1 | 10/2006 | Mangat et al. |
| 2006/0240070 A1 | 10/2006 | Cromack et al. |
| 2006/0246143 A1 | 11/2006 | Ege |
| 2006/0247266 A1 | 11/2006 | Yamada et al. |
| 2006/0247760 A1 | 11/2006 | Ganesan et al. |
| 2006/0263393 A1 | 11/2006 | Demopulos et al. |
| 2006/0269555 A1 | 11/2006 | Salcedo et al. |
| 2006/0271111 A1 | 11/2006 | Demarais et al. |
| 2006/0280858 A1 | 12/2006 | Kokish |
| 2006/0287644 A1 | 12/2006 | Inganas et al. |
| 2007/0016184 A1 | 1/2007 | Cropper et al. |
| 2007/0016274 A1 | 1/2007 | Boveja et al. |
| 2007/0027390 A1 | 2/2007 | Maschke et al. |
| 2007/0043077 A1 | 2/2007 | Mewshaw et al. |
| 2007/0043409 A1 | 2/2007 | Brian et al. |
| 2007/0049924 A1 | 3/2007 | Rahn |
| 2007/0066972 A1 | 3/2007 | Ormsby et al. |
| 2007/0073151 A1 | 3/2007 | Lee |
| 2007/0078498 A1 | 4/2007 | Rezai et al. |
| 2007/0093710 A1 | 4/2007 | Maschke |
| 2007/0100405 A1 | 5/2007 | Thompson et al. |
| 2007/0106247 A1 | 5/2007 | Burnett et al. |
| 2007/0112327 A1 | 5/2007 | Yun et al. |
| 2007/0118107 A1 | 5/2007 | Francischelli et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0149963 A1 | 6/2007 | Matsukuma et al. |
| 2007/0162109 A1 | 7/2007 | Davila et al. |
| 2007/0173805 A1 | 7/2007 | Weinberg et al. |
| 2007/0173899 A1 | 7/2007 | Levin et al. |
| 2007/0179496 A1 | 8/2007 | Swoyer et al. |
| 2007/0197891 A1 | 8/2007 | Shachar et al. |
| 2007/0203480 A1 | 8/2007 | Mody et al. |
| 2007/0207186 A1 | 9/2007 | Scanlon et al. |
| 2007/0208134 A1 | 9/2007 | Hunter et al. |
| 2007/0208210 A1 | 9/2007 | Gelfand et al. |
| 2007/0208256 A1 | 9/2007 | Marilla |
| 2007/0208301 A1 | 9/2007 | Evard et al. |
| 2007/0219576 A1 | 9/2007 | Cangialosi |
| 2007/0225781 A1 | 9/2007 | Saadat et al. |
| 2007/0233170 A1 | 10/2007 | Gertner |
| 2007/0239062 A1 | 10/2007 | Chopra et al. |
| 2007/0248639 A1 | 10/2007 | Demopulos et al. |
| 2007/0249703 A1 | 10/2007 | Mewshaw et al. |
| 2007/0254833 A1 | 11/2007 | Hunter et al. |
| 2007/0265687 A1 | 11/2007 | Deem et al. |
| 2007/0278103 A1 | 12/2007 | Hoerr et al. |
| 2007/0282302 A1 | 12/2007 | Wachsman et al. |
| 2007/0292411 A1 | 12/2007 | Salcedo et al. |
| 2007/0293782 A1 | 12/2007 | Marino |
| 2007/0299043 A1 | 12/2007 | Hunter et al. |
| 2008/0004673 A1 | 1/2008 | Rossing et al. |
| 2008/0009927 A1 | 1/2008 | Vilims |
| 2008/0015501 A1 | 1/2008 | Gertner |
| 2008/0021408 A1 | 1/2008 | Jacobsen et al. |
| 2008/0033049 A1 | 2/2008 | Mewshaw et al. |
| 2008/0039746 A1 | 2/2008 | Hissong et al. |
| 2008/0039830 A1 | 2/2008 | Munger et al. |
| 2008/0051454 A1 | 2/2008 | Wang |
| 2008/0064957 A1 | 3/2008 | Spence |
| 2008/0071269 A1 | 3/2008 | Hilario et al. |
| 2008/0071306 A1 | 3/2008 | Gertner |
| 2008/0082109 A1 | 4/2008 | Moll et al. |
| 2008/0086072 A1 | 4/2008 | Bonutti et al. |
| 2008/0091193 A1 | 4/2008 | Kauphusman et al. |
| 2008/0097251 A1 | 4/2008 | Babaev |
| 2008/0097426 A1 | 4/2008 | Root et al. |
| 2008/0108867 A1 | 5/2008 | Zhou |
| 2008/0119879 A1 | 5/2008 | Brenneman et al. |
| 2008/0125772 A1 | 5/2008 | Stone et al. |
| 2008/0132450 A1 | 6/2008 | Lee et al. |
| 2008/0140002 A1 | 6/2008 | Ramzipoor et al. |
| 2008/0147002 A1 | 6/2008 | Gertner |
| 2008/0161662 A1 | 7/2008 | Golijanin et al. |
| 2008/0161717 A1 | 7/2008 | Gertner |
| 2008/0161801 A1 | 7/2008 | Steinke et al. |
| 2008/0171974 A1 | 7/2008 | Lafontaine et al. |
| 2008/0172035 A1 | 7/2008 | Starksen et al. |
| 2008/0172104 A1 | 7/2008 | Kieval et al. |
| 2008/0188912 A1 | 8/2008 | Stone et al. |
| 2008/0188913 A1 | 8/2008 | Stone et al. |
| 2008/0208162 A1 | 8/2008 | Joshi |
| 2008/0208169 A1 | 8/2008 | Boyle et al. |
| 2008/0213331 A1 | 9/2008 | Gelfand et al. |
| 2008/0215117 A1 | 9/2008 | Gross |
| 2008/0221448 A1 | 9/2008 | Khuri-Yakub et al. |
| 2008/0234790 A1 | 9/2008 | Bayer et al. |
| 2008/0243091 A1 | 10/2008 | Humphreys et al. |
| 2008/0245371 A1 | 10/2008 | Gruber |
| 2008/0249525 A1 | 10/2008 | Lee et al. |
| 2008/0249547 A1 | 10/2008 | Dunn |
| 2008/0255550 A1 | 10/2008 | Bell |
| 2008/0255642 A1 | 10/2008 | Zarins et al. |
| 2008/0262489 A1 | 10/2008 | Steinke |
| 2008/0275484 A1 | 11/2008 | Gertner |
| 2008/0281312 A1 | 11/2008 | Werneth et al. |
| 2008/0281347 A1 | 11/2008 | Gertner |
| 2008/0287918 A1 | 11/2008 | Rosenman et al. |
| 2008/0294037 A1 | 11/2008 | Richter |
| 2008/0300618 A1 | 12/2008 | Gertner |
| 2008/0312644 A1 | 12/2008 | Fourkas et al. |
| 2008/0312673 A1 | 12/2008 | Viswanathan et al. |
| 2008/0317818 A1 | 12/2008 | Griffith et al. |
| 2009/0018486 A1 | 1/2009 | Goren et al. |
| 2009/0018609 A1 | 1/2009 | DiLorenzo |
| 2009/0024194 A1 | 1/2009 | Arcot-Krishnamurthy et al. |
| 2009/0030312 A1 | 1/2009 | Hadjicostis |
| 2009/0036948 A1 | 2/2009 | Levin et al. |
| 2009/0043372 A1 | 2/2009 | Northrop et al. |
| 2009/0054082 A1 | 2/2009 | Kim et al. |
| 2009/0062873 A1 | 3/2009 | Wu et al. |
| 2009/0069671 A1 | 3/2009 | Anderson |
| 2009/0074828 A1 | 3/2009 | Alexis et al. |
| 2009/0076409 A1 | 3/2009 | Wu et al. |
| 2009/0088735 A1 | 4/2009 | Abboud et al. |
| 2009/0105631 A1 | 4/2009 | Kieval |
| 2009/0112202 A1 | 4/2009 | Young |
| 2009/0118620 A1 | 5/2009 | Tgavalekos et al. |
| 2009/0118726 A1 | 5/2009 | Auth et al. |
| 2009/0125099 A1 | 5/2009 | Weber et al. |
| 2009/0131798 A1 | 5/2009 | Minar et al. |
| 2009/0143640 A1 | 6/2009 | Saadat et al. |
| 2009/0156988 A1 | 6/2009 | Ferren et al. |
| 2009/0157057 A1 | 6/2009 | Ferren et al. |
| 2009/0157161 A1 | 6/2009 | Desai et al. |
| 2009/0171333 A1 | 7/2009 | Hon |
| 2009/0192558 A1 | 7/2009 | Whitehurst et al. |
| 2009/0198223 A1 | 8/2009 | Thilwind et al. |
| 2009/0203962 A1 | 8/2009 | Miller et al. |
| 2009/0203993 A1 | 8/2009 | Mangat et al. |
| 2009/0204170 A1 | 8/2009 | Hastings et al. |
| 2009/0210953 A1 | 8/2009 | Moyer et al. |
| 2009/0216317 A1 | 8/2009 | Cromack et al. |
| 2009/0221955 A1 | 9/2009 | Babaev |
| 2009/0226429 A1 | 9/2009 | Salcedo et al. |
| 2009/0240249 A1 | 9/2009 | Chan et al. |
| 2009/0247933 A1 | 10/2009 | Maor et al. |
| 2009/0247966 A1 | 10/2009 | Gunn et al. |
| 2009/0248012 A1 | 10/2009 | Maor et al. |
| 2009/0253974 A1 | 10/2009 | Rahme |
| 2009/0264755 A1 | 10/2009 | Chen et al. |
| 2009/0270850 A1 | 10/2009 | Zhou et al. |
| 2009/0281533 A1 | 11/2009 | Ingle et al. |
| 2009/0287137 A1 | 11/2009 | Crowley |
| 2009/0318749 A1 | 12/2009 | Stolen et al. |
| 2010/0009267 A1 | 1/2010 | Chase et al. |
| 2010/0030061 A1 | 2/2010 | Canfield et al. |
| 2010/0048983 A1 | 2/2010 | Ball et al. |
| 2010/0049099 A1 | 2/2010 | Thapliyal et al. |

(56) References Cited

U.S. PATENT DOCUMENTS

| | | |
|---|---|---|
| 2010/0049186 A1 | 2/2010 | Ingle et al. |
| 2010/0049188 A1 | 2/2010 | Nelson et al. |
| 2010/0049191 A1 | 2/2010 | Habib et al. |
| 2010/0049283 A1 | 2/2010 | Johnson |
| 2010/0069837 A1 | 3/2010 | Rassat et al. |
| 2010/0076299 A1 | 3/2010 | Gustus et al. |
| 2010/0076425 A1 | 3/2010 | Carroux |
| 2010/0087782 A1 | 4/2010 | Ghaffari et al. |
| 2010/0106005 A1 | 4/2010 | Karczmar et al. |
| 2010/0114244 A1 | 5/2010 | Manda et al. |
| 2010/0125239 A1 | 5/2010 | Perry et al. |
| 2010/0125268 A1 | 5/2010 | Gustus et al. |
| 2010/0130836 A1 | 5/2010 | Malchano et al. |
| 2010/0137860 A1 | 6/2010 | Demarais et al. |
| 2010/0137952 A1 | 6/2010 | Demarais et al. |
| 2010/0160903 A1 | 6/2010 | Krespi |
| 2010/0160906 A1 | 6/2010 | Jarrard |
| 2010/0168624 A1 | 7/2010 | Sliwa |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0191112 A1 | 7/2010 | Demarais et al. |
| 2010/0191232 A1 | 7/2010 | Boveda |
| 2010/0204560 A1 | 8/2010 | Salahieh et al. |
| 2010/0217162 A1 | 8/2010 | Hissong et al. |
| 2010/0222786 A1 | 9/2010 | Kassab |
| 2010/0222851 A1 | 9/2010 | Deem et al. |
| 2010/0222854 A1 | 9/2010 | Demarais et al. |
| 2010/0228122 A1 | 9/2010 | Keenan et al. |
| 2010/0249604 A1 | 9/2010 | Hastings et al. |
| 2010/0249702 A1 | 9/2010 | Magana et al. |
| 2010/0249773 A1 | 9/2010 | Clark et al. |
| 2010/0256616 A1 | 10/2010 | Katoh et al. |
| 2010/0268217 A1 | 10/2010 | Habib |
| 2010/0268307 A1 | 10/2010 | Demarais et al. |
| 2010/0284927 A1 | 11/2010 | Lu et al. |
| 2010/0286684 A1 | 11/2010 | Hata et al. |
| 2010/0298821 A1 | 11/2010 | Garbagnati |
| 2010/0305036 A1 | 12/2010 | Barnes et al. |
| 2010/0312141 A1 | 12/2010 | Keast et al. |
| 2010/0324472 A1 | 12/2010 | Wulfman |
| 2011/0009750 A1 | 1/2011 | Taylor et al. |
| 2011/0021976 A1 | 1/2011 | Li et al. |
| 2011/0034832 A1 | 2/2011 | Cioanta et al. |
| 2011/0040324 A1 | 2/2011 | McCarthy et al. |
| 2011/0044942 A1 | 2/2011 | Puri et al. |
| 2011/0060324 A1 | 3/2011 | Wu et al. |
| 2011/0071400 A1 | 3/2011 | Hastings et al. |
| 2011/0071401 A1 | 3/2011 | Hastings et al. |
| 2011/0077498 A1 | 3/2011 | McDaniel |
| 2011/0092781 A1 | 4/2011 | Gertner |
| 2011/0092880 A1 | 4/2011 | Gertner |
| 2011/0104061 A1 | 5/2011 | Seward |
| 2011/0112400 A1 | 5/2011 | Emery et al. |
| 2011/0118598 A1 | 5/2011 | Gertner |
| 2011/0118600 A1 | 5/2011 | Gertner |
| 2011/0118726 A1 | 5/2011 | De La Rama et al. |
| 2011/0130708 A1 | 6/2011 | Perry et al. |
| 2011/0137155 A1 | 6/2011 | Weber et al. |
| 2011/0144479 A1 | 6/2011 | Hastings et al. |
| 2011/0146673 A1 | 6/2011 | Keast et al. |
| 2011/0166499 A1 | 7/2011 | Demarais et al. |
| 2011/0178403 A1 | 7/2011 | Weng et al. |
| 2011/0178570 A1 | 7/2011 | Demarais |
| 2011/0200171 A1 | 8/2011 | Beetel et al. |
| 2011/0202098 A1 | 8/2011 | Demarais et al. |
| 2011/0207758 A1 | 8/2011 | Sobotka et al. |
| 2011/0208096 A1 | 8/2011 | Demarais et al. |
| 2011/0257523 A1 | 10/2011 | Hastings et al. |
| 2011/0257564 A1 | 10/2011 | Demarais et al. |
| 2011/0257622 A1 | 10/2011 | Salahieh et al. |
| 2011/0257641 A1 | 10/2011 | Hastings et al. |
| 2011/0257642 A1 | 10/2011 | Griggs, III |
| 2011/0263921 A1 | 10/2011 | Vrba et al. |
| 2011/0264011 A1 | 10/2011 | Wu et al. |
| 2011/0264075 A1 | 10/2011 | Leung et al. |
| 2011/0264086 A1 | 10/2011 | Ingle |
| 2011/0264116 A1 | 10/2011 | Kocur et al. |
| 2011/0270238 A1 | 11/2011 | Rizq et al. |
| 2011/0306851 A1 | 12/2011 | Wang |
| 2011/0307034 A1 | 12/2011 | Hastings et al. |
| 2011/0319809 A1 | 12/2011 | Smith |
| 2012/0029496 A1 | 2/2012 | Smith |
| 2012/0029500 A1 | 2/2012 | Jenson |
| 2012/0029505 A1 | 2/2012 | Jenson |
| 2012/0029509 A1 | 2/2012 | Smith |
| 2012/0029510 A1 | 2/2012 | Haverkost |
| 2012/0029511 A1 | 2/2012 | Smith et al. |
| 2012/0029512 A1 | 2/2012 | Willard et al. |
| 2012/0029513 A1 | 2/2012 | Smith et al. |
| 2012/0059241 A1 | 3/2012 | Hastings et al. |
| 2012/0059286 A1 | 3/2012 | Hastings et al. |
| 2012/0065506 A1 | 3/2012 | Smith |
| 2012/0065554 A1 | 3/2012 | Pikus |
| 2012/0095461 A1 | 4/2012 | Herscher et al. |
| 2012/0101413 A1 | 4/2012 | Beetel et al. |
| 2012/0101490 A1 | 4/2012 | Smith |
| 2012/0101538 A1 | 4/2012 | Ballakur et al. |
| 2012/0109021 A1 | 5/2012 | Hastings et al. |
| 2012/0116382 A1 | 5/2012 | Ku et al. |
| 2012/0116383 A1 | 5/2012 | Mauch et al. |
| 2012/0116392 A1 | 5/2012 | Willard |
| 2012/0116438 A1 | 5/2012 | Salahieh et al. |
| 2012/0116486 A1 | 5/2012 | Naga et al. |
| 2012/0123243 A1 | 5/2012 | Hastings |
| 2012/0123258 A1 | 5/2012 | Willard |
| 2012/0123261 A1 | 5/2012 | Jenson et al. |
| 2012/0123303 A1 | 5/2012 | Sogard et al. |
| 2012/0123406 A1 | 5/2012 | Edmunds et al. |
| 2012/0130289 A1 | 5/2012 | Demarais et al. |
| 2012/0130345 A1 | 5/2012 | Levin et al. |
| 2012/0130359 A1 | 5/2012 | Turovskiy |
| 2012/0130360 A1 | 5/2012 | Buckley et al. |
| 2012/0130362 A1 | 5/2012 | Hastings et al. |
| 2012/0130368 A1 | 5/2012 | Jenson |
| 2012/0130458 A1 | 5/2012 | Ryba et al. |
| 2012/0136344 A1 | 5/2012 | Buckley et al. |
| 2012/0136349 A1 | 5/2012 | Hastings |
| 2012/0136350 A1 | 5/2012 | Goshgarian et al. |
| 2012/0136417 A1 | 5/2012 | Buckley et al. |
| 2012/0136418 A1 | 5/2012 | Buckley et al. |
| 2012/0143181 A1 | 6/2012 | Demarais et al. |
| 2012/0143293 A1 | 6/2012 | Mauch et al. |
| 2012/0143294 A1 | 6/2012 | Clark et al. |
| 2012/0150267 A1 | 6/2012 | Buckley et al. |
| 2012/0157986 A1 | 6/2012 | Stone et al. |
| 2012/0157987 A1 | 6/2012 | Steinke et al. |
| 2012/0157988 A1 | 6/2012 | Stone et al. |
| 2012/0157989 A1 | 6/2012 | Stone et al. |
| 2012/0157992 A1 | 6/2012 | Smith et al. |
| 2012/0157993 A1 | 6/2012 | Jenson et al. |
| 2012/0158101 A1 | 6/2012 | Stone et al. |
| 2012/0158104 A1 | 6/2012 | Huynh et al. |
| 2012/0172837 A1 | 7/2012 | Demarais et al. |
| 2012/0172870 A1 | 7/2012 | Jenson et al. |
| 2012/0184952 A1 | 7/2012 | Jenson et al. |
| 2012/0197198 A1 | 8/2012 | Demarais et al. |
| 2012/0197252 A1 | 8/2012 | Deem et al. |
| 2012/0232409 A1 | 9/2012 | Stahmann et al. |
| 2012/0265066 A1 | 10/2012 | Crow et al. |
| 2012/0265198 A1 | 10/2012 | Crow et al. |
| 2013/0012844 A1 | 1/2013 | Demarais et al. |
| 2013/0012866 A1 | 1/2013 | Deem et al. |
| 2013/0012867 A1 | 1/2013 | Demarais et al. |
| 2013/0013024 A1 | 1/2013 | Levin et al. |
| 2013/0023865 A1 | 1/2013 | Steinke et al. |
| 2013/0035681 A1 | 2/2013 | Subramaniam et al. |
| 2013/0066316 A1 | 3/2013 | Steinke et al. |
| 2013/0085489 A1 | 4/2013 | Fain et al. |
| 2013/0090563 A1 | 4/2013 | Weber |
| 2013/0090578 A1 | 4/2013 | Smith et al. |
| 2013/0090647 A1 | 4/2013 | Smith |
| 2013/0090649 A1 | 4/2013 | Smith et al. |
| 2013/0090650 A1 | 4/2013 | Jenson et al. |

(56) References Cited

U.S. PATENT DOCUMENTS

| | | |
|---|---|---|
| 2013/0090651 A1 | 4/2013 | Smith |
| 2013/0090652 A1 | 4/2013 | Jenson |
| 2013/0096550 A1 | 4/2013 | Hill |
| 2013/0096553 A1 | 4/2013 | Hill et al. |
| 2013/0096554 A1 | 4/2013 | Groff et al. |
| 2013/0096604 A1 | 4/2013 | Hanson et al. |
| 2013/0110106 A1 | 5/2013 | Richardson |
| 2013/0116687 A1 | 5/2013 | Willard |
| 2013/0165764 A1 | 6/2013 | Scheuermann et al. |
| 2013/0165844 A1 | 6/2013 | Shuros et al. |
| 2013/0165916 A1 | 6/2013 | Mathur et al. |
| 2013/0165917 A1 | 6/2013 | Mathur et al. |
| 2013/0165920 A1 | 6/2013 | Weber et al. |
| 2013/0165923 A1 | 6/2013 | Mathur et al. |
| 2013/0165924 A1 | 6/2013 | Mathur et al. |
| 2013/0165925 A1 | 6/2013 | Mathur et al. |
| 2013/0165926 A1 | 6/2013 | Mathur et al. |
| 2013/0165990 A1 | 6/2013 | Mathur et al. |
| 2013/0172815 A1 | 7/2013 | Perry et al. |
| 2013/0172872 A1 | 7/2013 | Subramaniam et al. |
| 2013/0172877 A1 | 7/2013 | Subramaniam et al. |
| 2013/0172878 A1 | 7/2013 | Smith |
| 2013/0172879 A1 | 7/2013 | Sutermeister |
| 2013/0172880 A1 | 7/2013 | Willard |
| 2013/0172881 A1 | 7/2013 | Hill et al. |

FOREIGN PATENT DOCUMENTS

| | | | |
|---|---|---|---|
| CN | 102271607 A | | 12/2011 |
| DE | 10038737 A1 | | 2/2002 |
| DE | 102005041601 A1 | | 4/2007 |
| DE | 102008048616 A1 | | 4/2010 |
| EP | 558297 A2 | | 9/1993 |
| EP | 647435 A1 | | 4/1995 |
| EP | 634910 B1 | | 8/1997 |
| EP | 868884 A2 | | 10/1998 |
| EP | 1005838 A1 | | 6/2000 |
| EP | 1053720 A1 | | 11/2000 |
| EP | 1064886 A1 | | 1/2001 |
| EP | 1180004 A1 | | 2/2002 |
| EP | 1181895 A2 | | 2/2002 |
| EP | 1297795 A1 | | 6/2002 |
| EP | 1264613 A2 | | 12/2002 |
| EP | 1286625 A1 | | 3/2003 |
| EP | 1332724 A1 | | 8/2003 |
| EP | 1335677 B1 | | 8/2003 |
| EP | 866675 B1 | | 10/2003 |
| EP | 1433448 A1 | | 6/2004 |
| EP | 1442719 A1 | | 8/2004 |
| EP | 1547537 A1 | | 6/2005 |
| EP | 1634542 A1 | | 3/2006 |
| EP | 1698296 A1 | | 6/2006 |
| EP | 1709922 A1 | | 10/2006 |
| EP | 1874211 A2 | | 1/2008 |
| EP | 1906853 A2 | | 4/2008 |
| EP | 1946712 A1 | | 7/2008 |
| EP | 1961394 A2 | | 8/2008 |
| EP | 1715798 B1 | | 4/2009 |
| EP | 1620156 B1 | | 7/2009 |
| EP | 2076193 A2 | | 7/2009 |
| EP | 2091455 A2 | | 8/2009 |
| EP | 2092957 A1 | | 8/2009 |
| EP | 2197533 A1 | | 6/2010 |
| EP | 2208506 A1 | | 7/2010 |
| EP | 1579889 B1 | | 8/2010 |
| EP | 2241279 A1 | | 10/2010 |
| EP | 2092957 B1 | | 1/2011 |
| EP | 2329859 A1 | | 6/2011 |
| EP | 2349044 A1 | | 8/2011 |
| EP | 2027882 B1 | | 10/2011 |
| EP | 2378956 A2 | | 10/2011 |
| EP | 2037840 B1 | | 12/2011 |
| EP | 2204134 B1 | | 4/2012 |
| EP | 2320821 B1 | | 10/2012 |
| GB | 2313062 A | | 11/1997 |
| GB | 2453601 A | | 4/2009 |
| GB | 2456301 A | | 7/2009 |
| JP | 7213621 | | 8/1995 |
| JP | 7313603 | | 12/1995 |
| JP | 2003-510126 A | | 3/2003 |
| WO | WO 91/03207 A1 | | 3/1991 |
| WO | WO 91/17731 A1 | | 11/1991 |
| WO | 9222239 A1 | | 12/1992 |
| WO | WO 93/20747 A1 | | 10/1993 |
| WO | WO 93/20770 A2 | | 10/1993 |
| WO | WO 94/18896 A1 | | 9/1994 |
| WO | WO 94/28809 A1 | | 12/1994 |
| WO | WO 95/01751 A1 | | 1/1995 |
| WO | WO 95/31142 A1 | | 11/1995 |
| WO | WO 96/34559 A1 | | 11/1996 |
| WO | WO 97/03604 A1 | | 2/1997 |
| WO | WO 97/17104 | | 5/1997 |
| WO | WO 97/20510 A1 | | 6/1997 |
| WO | WO 97/32532 A1 | | 9/1997 |
| WO | WO 97/40760 A1 | | 11/1997 |
| WO | 9745157 A1 | | 12/1997 |
| WO | WO 97/45156 A2 | | 12/1997 |
| WO | WO 98/18393 A1 | | 5/1998 |
| WO | 9829030 A1 | | 7/1998 |
| WO | WO 98/34565 A1 | | 8/1998 |
| WO | WO 98/35638 A1 | | 8/1998 |
| WO | WO 98/40023 A1 | | 9/1998 |
| WO | 9858588 A1 | | 12/1998 |
| WO | 9900060 A1 | | 1/1999 |
| WO | WO 99/00060 | | 1/1999 |
| WO | WO 99/16370 A1 | | 4/1999 |
| WO | WO 99/21608 A1 | | 5/1999 |
| WO | WO 99/34741 A1 | | 7/1999 |
| WO | WO 99/44522 A1 | | 9/1999 |
| WO | 0001313 A1 | | 1/2000 |
| WO | WO 00/10475 A1 | | 3/2000 |
| WO | 0047118 A1 | | 8/2000 |
| WO | WO 00/51513 A1 | | 9/2000 |
| WO | WO 00/59394 A1 | | 10/2000 |
| WO | WO 00/62727 A1 | | 10/2000 |
| WO | WO 00/64387 A1 | | 11/2000 |
| WO | WO 00/69376 A1 | | 11/2000 |
| WO | WO 00/72909 A1 | | 12/2000 |
| WO | WO 01/22897 A1 | | 4/2001 |
| WO | WO 01/37746 A1 | | 5/2001 |
| WO | WO 01/87172 A1 | | 5/2001 |
| WO | 0174255 A1 | | 10/2001 |
| WO | 0137723 A2 | | 11/2001 |
| WO | WO 01/87154 A1 | | 11/2001 |
| WO | WO 01/95820 A1 | | 12/2001 |
| WO | 0215807 A1 | | 2/2002 |
| WO | WO 02/28475 A1 | | 4/2002 |
| WO | WO 02/39915 A1 | | 5/2002 |
| WO | WO 02/058549 A1 | | 8/2002 |
| WO | WO 02/080766 A2 | | 10/2002 |
| WO | 02089871 A1 | | 11/2002 |
| WO | WO 02/087679 | | 11/2002 |
| WO | WO 02/089686 | | 11/2002 |
| WO | 03026525 A1 | | 4/2003 |
| WO | WO 03/077781 A1 | | 9/2003 |
| WO | WO 2004/047659 A2 | | 6/2004 |
| WO | WO 2004/049976 A1 | | 6/2004 |
| WO | WO 2004/064606 A2 | | 8/2004 |
| WO | WO 2004/069300 A2 | | 8/2004 |
| WO | WO 2004/076146 A2 | | 9/2004 |
| WO | 2004100813 A2 | | 11/2004 |
| WO | WO 2004/098694 A1 | | 11/2004 |
| WO | 2004110258 A2 | | 12/2004 |
| WO | WO 2004/105807 A2 | | 12/2004 |
| WO | WO 2005/007000 A1 | | 1/2005 |
| WO | WO 2005/037070 A2 | | 4/2005 |
| WO | WO 2005/041748 A2 | | 5/2005 |
| WO | WO 2005/074829 A1 | | 8/2005 |
| WO | WO 2006/041881 A2 | | 4/2006 |
| WO | 2006105121 A2 | | 10/2006 |
| WO | WO 2006/105121 A2 | | 10/2006 |
| WO | WO 2006/116198 A2 | | 11/2006 |
| WO | WO 2007/011634 A1 | | 1/2007 |

(56) References Cited

FOREIGN PATENT DOCUMENTS

| | | |
|---|---|---|
| WO | WO 2007/014063 A2 | 2/2007 |
| WO | WO 2007/047870 A2 | 4/2007 |
| WO | WO 2007/113865 A1 | 10/2007 |
| WO | WO 2007/135431 A2 | 11/2007 |
| WO | WO 2007/146215 A2 | 12/2007 |
| WO | 2008014465 A2 | 1/2008 |
| WO | WO 2008/003058 A2 | 1/2008 |
| WO | WO 2008/009972 A2 | 1/2008 |
| WO | WO 2008/010150 A2 | 1/2008 |
| WO | WO 2008/036281 A2 | 3/2008 |
| WO | WO 2008/049084 A2 | 4/2008 |
| WO | WO 2008/061152 A2 | 5/2008 |
| WO | WO 2008/102363 A2 | 8/2008 |
| WO | WO 2009/036471 A1 | 3/2009 |
| WO | WO 2009/082635 A1 | 7/2009 |
| WO | WO 2009/088678 A1 | 7/2009 |
| WO | WO 2009/113064 A2 | 9/2009 |
| WO | 2009121017 A1 | 10/2009 |
| WO | WO 2009/121017 A1 | 10/2009 |
| WO | WO 2009/137819 A1 | 11/2009 |
| WO | WO 2010/042653 A1 | 4/2010 |
| WO | WO 2010/048007 A1 | 4/2010 |
| WO | WO 2010/056771 A1 | 5/2010 |
| WO | WO 2010/057043 A1 | 5/2010 |
| WO | 2010067360 A2 | 6/2010 |
| WO | WO 2010/070766 A1 | 6/2010 |
| WO | 2010102310 A2 | 9/2010 |
| WO | WO 2010/099207 A1 | 9/2010 |
| WO | WO 2010/120944 A2 | 10/2010 |
| WO | WO 2010/134503 A1 | 11/2010 |
| WO | 2011005901 A2 | 1/2011 |
| WO | 2011053757 A1 | 5/2011 |
| WO | 2011053772 A1 | 5/2011 |
| WO | WO 2011/055143 A2 | 5/2011 |
| WO | WO 2011/060339 A1 | 5/2011 |
| WO | 2011091069 A1 | 7/2011 |
| WO | 2011130534 A2 | 10/2011 |
| WO | WO 2011/126580 A2 | 10/2011 |
| WO | 2012019156 A1 | 2/2012 |
| WO | 2013049601 A2 | 4/2013 |

OTHER PUBLICATIONS

Brown et al., "Radiofrequency capacitive heaters: the effect of coupling medium resistivity on power absorption along a mouse leg," Phys Med Biol 1993, 38 1-12 (abstract).

Carrington, "Future of CVI: It's All About the Plaque", Diagnostic Imaging Special Edition Forum [online] [retrieved on Sep. 3, 2003] Retrieved from the Internet: <http://dimag.com/specialedition/cardiacimg.shtml> 5 pages total.

Cimino, "Preventing Plaque Attack", [online] [retrieved on Sep. 3, 2003] Retrieved from the Internet: <http://Masshightech.com/displayarticledetail.ap?art_id=52283&cat_id=10>, 3 pages total.

Dahm et al, "Relation of Degree of Laser Debulking of In-Stent Restenosis as a Predictor of Restenosis Rate", Am J Cardiol, vol. 90, (Jul. 20020, pp. 68-70.

De Korte et al., "Characterization of Plaque Components with Intravascular Ultrasound Elastography in Human Femoral and Coronary Arteries In Vitro," Circulation 2000;102:617-623.

Fujimori et al., "Significant Prevention of In-Stent Restenosis by Evans Blue in Patients with Acute Myocardial Infarction", Abstract #2925, AHA (2002), 1 page total.

Fujita, "Sarpogrelate, An Antagonist of 5-HT2a Receptor Treatment Reduces Restenosis After Coronary Stenting", Abstract #2927, AHA (2002), 1 page total.

Gregory et al., "Liquid Core Light Guide for Laser Angioplasty", Journal of Quantum Electronics, vol. 26, No. 12, (Dec. 1990), pp. 2289-2296.

Intraluminal, Product description [online] [retrieved on Sep. 3, 2003] Retrieved from the Internet: http://www.intraluminal.com/products/index.html> 1 page total.

Kolata, "New Studies Question Value of Opening Arteries", New York Times [online] [retrieved on Jan. 25, 2005]. Retrieved from the Internet: <http://nytimes.com/2004/03/21/health/21HEAR.html?ei=5070&en=641bc03214e&ex=11067>, 5 pages total.

Konings M K, et al., "Development of an Intravascular Impedance Catheter for Detection of Fatty Lesions in Arteries," IEEE Transactions on Medical Imaging, vol. 16 No. 4, Aug. 1997.

Kurtz et al., "Lamellar Refractive Surgery with Scanned Intrastromal Picosecond and Femtosecond Laser Pulses in Animal Eyes", J Refract Surg, vol. 14, (Sep./Oct. 1998), pp. 541-548.

Lightlab Imaging Technology, "Advantages of OCT", [online] [retrieved on Sep. 3, 2003]. Retrieved from the Internet: <http:www.lightlabimaging.com/advantage.html> 2 pages total.

Lightlab Imaging Technology, "Image Gallery", [online] [retrieved on Sep. 3, 2003]. Retrieved from the Internet: <http:lightlabimaging.com/gallery/cvpstill.html> 4 pages total.

Lightlab Imaging Technology, "LightLab Imaging Starts US Cardiology Clinical Investigations", LightLab Company Press Release, [online] [retrieved on Sep. 3, 2003]. Retrieved from the Internet: <http://www.lighlabimaging.com/press/cardtrails.html> 2 pages total.

Lightlab Imaging Technology, "LightLab Sees Bright Prospects for Cardiac Application of OCT Technology" The Graysheet Medical Devices Diagnostics & Instrumentation, vol. 27, No. 35, (Aug. 27, 2001) [online] [retrieved on Sep. 3, 2003]. Retrieved from the Internet: <http://www.lighlabimaging.com/press/graysheet.html> 1 page total.

Lightlab Imaging Technology, "What is OCT?", [online] [retrieved on Sep. 3, 2003]. Retrieved from the Internet: <http:lightlabimaging.com/oct.html.> 2 pages total.

Lightlab Imaging Technology, "Why use OCT?", [online] [retrieved on Sep. 3, 2003]. Retrieved from the Internet: <httplightlabimaging.com/whyoct.html> 2 pages total.

Lima et al., "Efficacy and Safety of Oral Sirolimus to Treat and Prevent In-Stent Restenosis: A Pilot Study Results", Abstract #2929, AHA (2002), 1 page total.

Lima et al., "Systemic Immunosuppression Inhibits In-Stent Coronary Intimal Proliferation in Renal Transplant Patients", Abstract #2928, AHA (2002), 1 page total.

MIT Techtalk, "Laser Catheter to Aid Coronary Surgery", Jan. 9, 1991 [online] [retrieved on Feb. 7, 2005]. Retrieved from the Internet : <http://web.mit.edu/newsoffice/tt/1991/jan09/24037.html> 4 pages total.

Morice et al., " A Randomized Comparison of A Sirolimus-Eluting Stent With a Standard Stent for Coronary Revascularization", N. Engl J Med, vol. 346, No. 23, (Jun. 6, 2002), pp. 1773-1779.

Müller et al., "Effectiveness and Safety of Ultrasonic Atherosclerotic Plaque Ablation: In Vitro Investigation", CardioVas. Intervent. Radiol., (1993) 16: 303-307.

Nair A, et al., "Regularized Autoregressive Analysis of Intravascular Ultrasound Backscatter: Improvement in Spatial Accuracy of Tissue Maps," IEEE Transactions on Ultrasonics, Ferroelectrics, and Frequency Control, vol. 51, No. 4, Apr. 2004.

Popma et al., "Chapter 38—Percutaneous Coronary and Valvular Intervention", Heart Disease: A Textbook of Cardiovascular Medicine, 6th ed., (2001) W.B> Saunders Company, pp. 1364-1405.

Scheller, "Coronary Paclitaxel Added to Contrast Media Inhibits In-Stent Restenosis of Porcine Coronary Arteries", Abstract #2227, AHA (2002), 1 page total.

Shaffer, "Scientific Basis of Laser Energy", Clin Sports Med 21: 4 (2002) pp. 585-598.

Shmatukha A V et al., "MRI temperature mapping during thermal balloon angioplasty," Phys Med Biol 51, (2006) N163-N171.

Slager et al., Vaporization of Atherosclerotic Plaques by Spark Erosion, J Am Coll Cardiol, vol. 5 (Jun. 1985), pp. 1382-1386.

Stiles D K, et al., "Simulated Characterization of Atherosclerotic Lesions in the Coronary Arteries by Measurement of Bioimpedance," IEEE Transactions on Biomedical Engineering, vol. 50 No. 4, Jul. 2003.

Suselbeck et al., "In vivo intravascular electrical impedance spectroscopy using a new catheter with integrated microelectrodes," Basic Res Cardiol 100:28-34 (2005).

(56) References Cited

OTHER PUBLICATIONS

Van Den Berg, "Light Echoes Image the Human Body", OLE, (Oct. 2001), pp. 35-37.
Volcano Therapeutics, "Product—Functional Measurement", [online] [retrieved on Mar. 9, 2003]. Retrieved from the Internet: <http://www.volcanotherapeutics.com/pages/products/functional_measurement-us.html> 2 pages total.
Kaplan et al., "Healing after arterial dilatation with radiofrequency thermal and nonthermal balloon angioplasty systems," J Invest Surg. Jan.-Feb. 1993;6(1):33-52.
Van Den Berg, "Light echoes image the human body," OLE, Oct. 2001, p. 35-37.
"IntraLuminal: Products," IntraLuminal Therapeutics, Inc., 2003, p. 1-9.
"Laser Catheter to Aid Coronary Surgery," TechTalk: MIT, Jan. 9, 1991, p. 1-4.
"Optical Coherence Tomography: LightLab Imaging Starts US Cardiology Clinical Investigations," LightLab Imaging Technology, 2002.
"Optical Coherence Tomography: LightLab Sees Bright Prospects for Cardiac Application of OCT Technology," LightLab Imaging Technology, 2001, vol. 27, No. 35.
"Products—Functional Measurement," VOLCANO Functional Measurement Products US, Mar. 24, 2003, p. 1-2.
Brown et al., "Radiofrequency capacitive heaters: the effect of coupling medium resistivity on power absorption along a mouse leg," Physics in Medicine and Biology, 1993, p. 1-12, vol. 38.
Carrington, "Future of CVI: It's all about plaque: Identification of vulnerable lesions, not 'rusty pipes,' could become cornerstone of preventive cardiology," Diagnostic Imaging, 2001, p. 1-8.
Chen et al., "Percutaneous pulmonary artery denervation completely abolishes experimental pulmonary arterial hypertension in vivo," EuroIntervention, 2013, p. 1-8.
Cimino, "Preventing plaque attack," Mass High Tech, 2001, p. 1-2.
Dahm et al., "Relation of Degree of Laser Debulking of In-Stent Restenosis as a Predictor of Restenosis Rate," The American Journal of Cardiology, 2002, p. 68-70, vol. 90.
De Korte et al., "Characterization of Plaque Components With Intravascular Ultrasound Elastography in Human Femoral and Coronary Arteries In Vitro," Circulation, Aug. 8, 2000, p. 617-623.
Durney et al., "Radiofrequency Radiation Dosimetry Handbook," Oct. 1986, p. 1-2, Fourth Edition.
Durney et al., "Radiofrequency Radiation Dosimetry Handbook: Contents," Oct. 1986, p. 1-5, Fourth Edition.
Fournier-Desseux et al., "Assessment of 1-lead and 2-lead electrode patterns in electrical impedance endotomography," Physiological Measurement, 2005, p. 337-349. Vo. 26, Institute of Physics Publishing.
Fram et al., "Feasibility of Radiofrequency Powered, Thermal Balloon Ablation of Atrioventricular Bypass Tracts via the Coronary Sinus: In Vivo Canine Studies," PACE, Aug. 1995, p. 1518-1530, vol. 18.
Fram et al., "Low Pressure Radiofrequency Balloon Angioplasty: Evaluation in Porcine Peripheral Arteries," JACC, 1993, p. 1512-1521, vol. 21, No. 6, American College of Cardiology.
Fujimori et al., "Significant Prevention of In-Stent Restenosis by Evans Blue in Patients with Acute Myocardial Infarction," American Heart Association, 2002.
Fujita et al., "Sarpogrelate, An Antagonist of 5-HT(2A) Receptor, Treatment Reduces Restenosis After Coronary Stenting," American Heart Association, 2002.
Gabriel, "Appendix A: Experimental Data," 1999, p. 1-21.
Gregory et al., "Liquid Core Light Guide for Laser Angioplasty," The Journal of Quantum Electronics, Dec. 1990, p. 2289-2296, vol. 26, No. 12.
Kaplan et al., "Healing after Arterial Dilatation with Radiofrequency Thermal and Nonthermal Balloon Angioplasty Sytems," Journal of Investigative Surgery, 1993, p. 33-52, vol. 6.
Kolata, "New Studies Question Value of Opening Arteries," The New York Times, Mar. 21, 2004, p. 1-5.
Konings et al., "Development of an Intravascular Impedance Catheter for Detection of Fatty Lesions in Arteries," IEEE Transactions on Medical Imaging, Aug. 1997, p. 439-446, vol. 16, No. 4.
Kurtz et al., "Lamellar Refractive Surgery with Scanned Intrastromal Picosecond and Femtosecond Laser Pulses in Animal Eyes," Journal of Refractive Surgery, Sep./Oct. 1998, p. 541-548.
Lee et al., "Thermal Compression and Molding of Atherosclerotic Vascular Tissue With Use of Radiofrequency Energy: Implications for Radiofrequency Balloon Angioplasty," JACC, 1989, p. 1167-1175, vol. 13, No. 5, American College of Cardiology.
Lima et al., "Efficacy and Safety of Oral Sirolimus to Treat and Prevent In-Stent Restenosis: A Pilot Study Results," American Heart Association, 2002, p. 2929.
Lima et al., "Systemic Immunosuppression Inhibits In-Stent Coronary Intimal Proliferation in Renal Transplant Patients," American Heart Association, 2002, p. 2928.
Morice et al., "A Randomized Comparison of a Sirolimus-Eluting Stent With a Standard Stent for Coronary Revascularization," The New England Journal of Medicine, Jun. 6, 2012, p. 1773-1780, vol. 346, No. 23.
Muller-Leisse et al., "Effectiveness and Safety of Ultrasonic Atherosclerotic Plaque Ablation: In Vitro Investigation," CardioVascular and Interventional Radiology, 1993, p. 303-307, vol. 16.
Nair et al., "Regularized Autoregressive Analysis of Intravascular Ultrasound Backscatter: Improvement in Spatial Accuracy of Tissue Maps," IEEE Transactions on Ultrasonics, Apr. 2004, p. 420-431, vol. 51, No. 4.
Resar et al., "Endoluminal Sealing of Vascular Wall Disruptions With Radiofrequency-Heated Balloon Angioplasty," Catheterization and Cardiovascular Diagnosis, 1993, p. 161-167, vol. 29.
Romer et al., "Histopathology of Human Coronary Atherosclerosis by Quantifying Its Chemical Composition With Raman Spectroscopy," Circulation, 1998, p. 878-885, vol. 97.
Schauerte et al., "Catheter Ablation of Cardiac Autonomic Nerves for Prevention of Vagal Atrial Fibrillation," Circulation, 2000, p. 2774-2780, vol. 102.
Scheller et al., "Intracoronary Paclitaxel Added to Contrast Media Inhibits In-Stent Restenosis of Porcine Coronary Arteries," American Heart Association, 2002, p. 2227.
Scheller et al., "Potential solutions to the current problem: coated balloon," EuroIntervention, 2008, p. C63-C66, vol. 4 (Supplement C).
Shaffer, "Scientific basis of laser energy," Clinics in Sports Medicine, 2002, p. 585-598, vol. 21.
Shmatukha et al., "MRI temperature mapping during thermal balloon angioplasty," Physics in Medicine and Biology, 2006, p. N163-N171, vol. 51.
Slager et al., "Vaporization of Atherosclerotic Plaques by Spark Erosion," J Am Coll Cardiol, 1985, p. 21-25.
Stiles et al., "Simulated Characterization of Atherosclerotic Lesions in the Coronary Arteries by Measurement of Bioimpedance," IEEE Transactions on Biomedical Engineering, Jul. 2003, p. 916-921, vol. 50, No. 7.
Suselbeck et al., "In vivo intravascular electric impedance spectroscopy using a new catheter with integrated microelectrodes," Basic Res Cardiol, 2005, p. 28-34, vol. 100.
Suselbeck et al., "Intravascular electric impedance spectroscopy of atherosclerotic lesions using a new impedance catheter system," Basic Res Cardiol, 2005, p. 446-452, vol. 100.
Tepe et al., "Local Delivery of Paclitaxel to Inhibit Restenosis during Angioplasty of the Leg," The New England Journal of Medicine, 2008, p. 689-699, vol. 358.
US 8,398,630, 3/2013, Demarais et al. (withdrawn).
CardioVascular Technologies Inc., "Heated Balloon Device Technology," 11 pages, 2008.
Strategic Business Development, Inc., "Thermal and Disruptive Angioplasty: A Physician's Guide," 8 pages, 1990.
Zhang et al., "Non-contact Radio-Frequency Ablation for Obtaining Deeper Lesions," IEEE Transaction on Biomedical Engineering, vol. 50, No. 2, 6 pages, Feb. 2003.
Lazebnik et al., "Tissue Strain Analytics Virtual Touch Tissue Imaging and Qualification," Siemens Whitepaper, Oct. 2008, 7 pages.

(56) References Cited

OTHER PUBLICATIONS

Zhou et al., "Mechanism Research of Ciyoanalgesia," Forefront Publishing Group, 1995.
Florete, "Cryoblative Procedure for Back Pain," Jacksonville Medicine, Oct. 1998, 10 pages.
Stevenson, "Irrigated RF Ablation: Power Titration and Fluid Management for Optimal Safety Efficacy," 2005, 4 pages.
Giliatt et al., "The Cause of Nerve Damage in Acute Compression," Trans Am Neurol Assoc, 1974: 99; 71-4.
Baun, "Interaction with Soft Tissue," Principles of General & Vascular Sonography, Chapter 2, pp. 23-24, Before Mar. 2012.
Blue Cross Blue Shield Medicaly Policy, "Surgery Section—MRI-Guided Focused Ultrasound (MRgFUS) for the Treatment of Uterine Fibroids and Other Tumors," 2005, 5 pages.
Gentry et al., "Combines 3D Intracardiac Echo and Ultrasound Ablation," Medical Imaging 2003: Ultrasonic and Signal Processing, vol. 5035, 2003, pp. 166-173.
Lafon et al., "Optmizing the Shape of Ultrasound Transducers for Interstitial Thermal Ablations," MEd Phys. Mar. 2002; 29(3): 290-7 (abstract only).
G. Ter Haar, "Ultrasound Focal Beam Surgery," Ultrasound in Med. & Biol., 1995, vol. 21, No. 9, pp. 1089-1100.
Seip et al., "Transurethral High Intensity Focused Ultrasound: Catheter Based Prototypes and Experimental Results," IEEE Ultrasonics Symposium Proceeding, 2000, 4 pages.
Toytman et al., "Tissue Dissection with Ultrafast Laser Using Extended and Multiple Foci," SPIE Proceeding, Optical Interactions with Tissues and Cells XXI, vol. 7562, 2010, 10 pages.
Zhoue et al., "Non-Thermal Ablation of Rabbit Liver VX2 Tumore by Pulsed High Intensity Focused Ultrasound Contrast Agent: Pathological Characteristics," World Journal of Gastroenterology, vol. 14(43), Nov. 21, 2008, pp. 6743-6747.
Cardiovascular Technologies, Inc., "Heated Balloon Device Technology" [Presentation], 2007-2008, 11 pages total. Retrieved from: <<http://www.cvtechinc.com/pr/presoCVT_Heated_Balloon_Tech.pdf>>.
Durney C., et al., Radiofrequency Radiation Dosimetry Handbook (with table of contents), Oct. 1986, 4th ed., 7 pages, Armstrong Laboratory (AFMC) Occupational and Environmental Health Directorate Radiofrequency Radiation Division, USAF School of Aerospace Medicine, Aerospace Medical Division (AFSC), Brooks Air Force Base, http://www.brooks.af.mil/AFRL/HED/hedr/reports/handbook/home.htm.
Fournier-Desseux et al. "Assessment of 1-lead and 2-lead electrode patterns in electrical impedance endotomography", Physiol. Meas. (2005) 26:337-349.
Gabriel C, et al., Compilation of the Dielectric Properties of Body Tissues at RF and Microwave Frequencies (with table of contents), Jun. 1996, 17 pages, Armstrong Laboratory (AFMC) Occupational and Environmental Health Directorate Radiofrequency Radiation Division, USAF School of Aerospace Medicine, Aerospace Medical Division (AFSC), Brooks Air Force Base, http://www.brooks.af.mil/AFRL/HED/hedr/Reports/dielectric/Report/Report.html.
Gabriel C, et al., Compilation of the Dielectric Properties of Body Tissues at RF and Microwave Frequencies, Appendi04-10-2009 A, Jun. 1996, 21 pages, Armstrong Laboratory (AFMC) Occupational and Environmental Health Directorate Radiofrequency Radiation Division, USAF School of Aerospace Medicine, Aerospace Medical Division (AFSC), Brooks Air Force Base, http://www.brooks.af.mil/AFRL/HED/hedr/reports/dielectric/Appendi04-10-2009.A/Appendi04-10-2009 A.html.
Gabriel C, et al., Compilation of the Dielectric Properties of Body Tissues at RF and Microwave Frequencies, Appendi04-10-2009 C, Jun. 1996, 6 pages, Armstrong Laboratory (AFMC) Occupational and Environmental Health Directorate Radiofrequency Radiation Division, USAF School of Aerospace Medicine, Aerospace Medical Division (AFSC), Brooks Air Force Base, http://www.brooks.af.mil/AFRL/HED/hedr/reports/dielectric/Appendi04-10-2009.C/Appendi04-10-2009 C.html.
Romer et al., "Histopathology of Human Coronary Atherosclerosis by Quantifying Its Chemical Composition with Raman Spectroscopy," Circulation 97:878-885 (1998).
Scheller et al., "Potential Solutions to the Current Problem: Coated Balloon," EuroIntervention, Aug. 2008; 4 Suppl C: C63-66.
Süselbeck et al. "Intravascular electric impedance spectroscopy of atherosclerotic lesions using a new impedance system", Basic Res Cardiol (2005) 100:446-452.
Tepe et al., "Local Delivery of Paclitaxel to Inhibit Restenosis During Angioplasty of the Leg," N Engl J Med, Feb. 14, 2008; 358(7): 689-699; retrieved from the Internet: <<http://content.nejm.org/cgi/reprint/358/7/689.pdf>>.
Examiners Report of Canadian Patent Application No. 2,539,026, mailed Feb. 6, 2012, 4 pages total.
Office Action issued in Chinese Patent Application No. 200480030163.9, mailed Jan. 16, 2009, 8 pages total.
Office Action issued in Chinese Patent Application No. 200480030163.9, mailed Mar. 28, 2008, 7 pages total.
Office Action issued in Chinese Patent Application No. 200480030163.9, mailed Aug. 31, 2007, 8 pages total.
Office Action issued in Chinese Patent Application No. 200480030163.9, mailed Jul. 31, 2009, 5 pages total.
Office Action issued in European Application No. 04816863.7, mailed Jun. 4, 2010, 5 pages total.
Office Action issued in European Application No. 04816863.7, mailed Dec. 5, 2011, 4 pages total.
Office Action issued in European Application No. 04816863.7, mailed Jan. 22, 2010, 6 pages total.
Formal Inquiry issued in Japanese Patent Application No. 2006-526351, mailed Jan. 17, 2012, 5 pages total.
Notice of the Reason for Refusal issued in Japanese Patent Application No. 2006-526351, mailed Apr. 27, 2010, 6 pages total.
Final Decision of Rejection issued in Japanese Patent Application No. 2006-526351, mailed Jan. 18, 2011, 4 pages total.
European Search Report and Search Opinion of EP Patent Application No. 12151957.3, mailed Apr. 16, 2012, 8 pages total.
Office Action issued in Chinese Patent Application No. 200680016424.0, mailed Apr. 13, 2010, 10 pages total.
European Search Report and Search Opinion of EP Patent Application No. 06748830.4, mailed Nov. 16, 2009, 12 pages total.
Partial European Search Report of EP Patent Application No. 11191822.3, mailed Mar. 19, 2012, 7 pages total.
Office Action issued in Chinese Patent Application No. 20111031923.X, mailed Nov. 17, 2011, 16 pages total.
Office Action issued in Chinese Patent Application No. 20111031923.X, mailed May 22, 2012, 10 pages total.
Examiner's First Report of Australian Patent Application No. 2007310988, mailed May 23, 2012, 4 pages total.
European Search Report and Search Opinion of EP Patent Application No. 07844421.3, mailed Jan. 4, 2010, 15 pages total.
European Search Report and Search Opinion of EP Patent Application No. 12155447.1, mailed May 10, 2012, 6 pages total.
International Search Report and Written Opinion of PCT Application No. PCT/US2009/064027, mailed Jan. 19, 2010, 9 pages total.
European Search Report and Search Opinion of EP Patent Application No. 07844417.1, mailed Nov. 5, 2009.
European Search Report and Search Opinion of EP Patent Application No. 12154120.5, mailed May 8, 2012, 8 pages total.
European Search Report and Search Opinion of EP Patent Application No. 07844424.7, mailed Nov. 11, 2009, 11 pages total.
Partial European Search Report of EP Patent Application No. 12154069.4, mailed May 10, 2012, 5 pages total.
International Search Report and Written Opinion of PCT Application No. PCT/US2009/064465, mailed Jan. 13, 2010, 13 pages total.
International Search Report of PCT Application No. PCT/US09/57728, mailed Nov. 30, 2009, 10 pages total. (2410PC).
International Search Report and Written Opinion of PCT/US2010/034789, mailed Jul. 9, 2010, 13 pages total.
International Search Report and Written Opinion of PCT/US2011/00661, mailed Nov. 18, 2011, 14 pages total.

(56) References Cited

OTHER PUBLICATIONS

Brown et al., "Observations on the Shrink Temperature of Collagen and Its Variations with Age and Disease," Ann Rheum Dis., vol. 17, No. 2, pp. 196-208, Jun. 1, 1958.

Gabriel, "Appendix C: Modeling the frequency dependence of the dielectric properties to a 4 dispersions spectrum," p. 1-49, Nov. 6, 1997.

Han et al., "Third-Generation Cryosurgery for Primary and Recurrent Prostate Caner," BJU International, vol. 93, pp. 14-18, 2004.

Omura et al., "A Mild Acute Compression Induces Neurapraxia in Rat Sciatic Nerve," The International Journal of Neuroscience, vol. 114 (12), pp. 1561-1572, Dec. 2004.

"Optical Coherence Tomography: Advantages of OCT," LightLab Imaging Technology, printed Sep. 3, 2003.

"Optical Coherence Tomography: Image Gallery Cardiovascular Procedures," LightLab Imaging Technology, printed Sep. 3, 2003.

"Optical Coherence Tomography: What is OCT?," LightLab Imaging Technology, printed Sep. 3, 2003.

"Optical Coherence Tomography: Why Use OCT?," LightLab Imaging Technology, printed Sep. 3, 2003.

Popma et al., "Percutaneous Coronary and Valvular Intervention," Braunwald's Heart Disease: A Textbook of Cardiovascular Medicine, 7th edition, p. 1364-1405, 2005.

\* cited by examiner

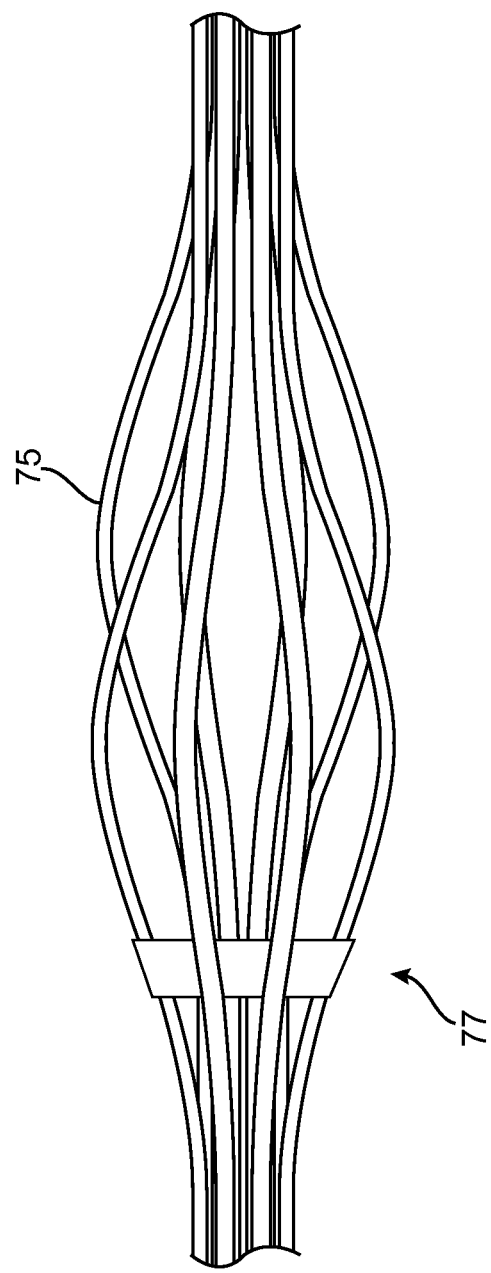

SELECTABLE ECCENTRIC REMODELING AND/OR ABLATION OF ATHEROSCLEROTIC MATERIAL

CROSS-REFERENCES TO RELATED APPLICATIONS

This application is a divisional patent application which claims priority from U.S. Patent No. 7,291,146 issued on Nov. 6, 2007, which claims the benefit under 35 USC 119(e) of U.S. Provisional Patent Application No. 60/502,515, filed on Sep. 12, 2003, the full disclosures of which are incorporated herein by reference.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK.

NOT APPLICABLE

BACKGROUND OF THE INVENTION

Field of the Invention

The present invention is generally related to medical devices, systems, and methods. In an exemplary embodiment, the invention provides catheter-based remodeling and/or removal of atherosclerosis plaque built-up in an artery to improve blood flow, often without balloon angioplasty, stenting, and/or dilation. The structures of the invention allow image-guided eccentric atherosclerotic material remodeling and/or removal typically using electrosurgical energy, optionally using electrosurgical ablation, often in a controlled environment zone within the blood vessel, and ideally with a co-located intravascular imaging capability. Related embodiments have applications in a variety of body lumens, including urinary, reproductive, gastrointestinal, and pulmonary obstructive material removal, optionally for removing or decreasing tumors, cysts, polyps, and the like.

Physicians use catheters to gain access to and repair interior tissues of the body, particularly within the lumens of the body such as blood vessels. For example, balloon angioplasty and other catheters often are used to open arteries that have been narrowed due to atherosclerotic disease.

Balloon angioplasty is often effective at opening an occluded blood vessel, but the trauma associated with balloon dilation can impose significant injury, so that the benefits of balloon dilation may be limited in time. Stents are commonly used to extend the beneficial opening of the blood vessel,.

Stenting, in conjunction with balloon dilation, is often the preferred treatment for atherosclerosis. In stenting, a collapsed metal framework is mounted on a balloon catheter which is introduced into the body. The stent is manipulated into the site of occlusion and expanded in place by the dilation of the underlying balloon. Stenting has gained widespread acceptance, and produces generally acceptable results in many cases. Along with treatment of blood vessels (particularly the coronary arteries), stents can also be used in treating many other tubular obstructions within the body, such as for treatment of reproductive, gastrointestinal, and pulmonary obstructions.

Restenosis or a subsequent narrowing of the body lumen after stenting has occurred in a significant number of cases. More recently, drug coated stents (such as Johnson and Johnson's Cypher™ stent, the associated drug comprising Sirolimus™) have demonstrated a markedly reduced restenosis rate, and others are developing and commercializing alternative drug eluting stents. In addition, work has also been initiated with systemic drug delivery (intravenous or oral) which may also improve the procedural angioplasty success rates.

While drug eluting stents appear to offer significant promise for treatment of atherosclerosis in many patients, there remain many cases where stents either cannot be used or present significant disadvantages. Generally, stenting leaves an implant in the body. Such implants can present risks, including mechanical fatigue, corrosion, and the like, particularly when removal of the implant is difficult and involves invasive surgery. Stenting may have additional disadvantages for treating diffuse artery disease, for treating bifurcations, for treating areas of the body susceptible to crush, and for treating arteries subject to torsion, elongation, and shortening.

A variety of modified restenosis treatments or restenosis-inhibiting occlusion treatment modalities have also been proposed, including intravascular radiation, cryogenic treatments, ultrasound energy, and the like, often in combination with balloon angioplasty and/or stenting. While these and different approaches show varying degrees of promise for decreasing the subsequent degradation in blood flow following angioplasty and stenting, the trauma initially imposed on the tissues by angioplasty remains problematic.

A number of alternatives to stenting and balloon angioplasty so as to open stenosed arteries have also been proposed. For example, a wide variety of atherectomy devices and techniques have been disclosed and attempted. Despite the disadvantages and limitations of angioplasty and stenting, atherectomy has not gained the widespread use and success rates of dilation-based approaches. Still further disadvantages of dilation have come to light. These include the existence of vulnerable plaque, which can rupture and release materials that may cause myocardial infarction or heart attack.

In light of the above, it would be advantageous to provide new devices, systems, and methods for remodeling and/or removal of atherosclerotic material and other occlusions of the lumens of the body, and particularly from blood vessels. It would further be desirable to enable the removal of these occlusive materials without having to resort to the trauma of a dilation, and to allow the opening of blood vessels and other body lumens which are not suitable for stenting.

BRIEF SUMMARY OF THE INVENTION

In a first aspect, the invention provides a catheter system for eccentric remodeling of atherosclerotic material of a blood vessel of a patient. The system comprises an elongate flexible catheter body having a proximal end and a distal end with an axis therebetween. A radially expandable structure is disposed near the end of the catheter body, and a plurality of energy delivery surfaces are each oriented radially when the expandable structure expands. An atherosclerotic material detector is disposed for circumferential atherosclerotic material detection. A power source is electrically coupled to the energy delivery surfaces. The power source energizes the energy delivery surfaces so as to eccentrically remodel the detected atherosclerotic material.

The power source will often selectively energize a subset of the energy delivery surfaces so as to effect eccentric remodeling. The catheter body may have a lumen extending between the proximal and distal ends, and an aspiration connector may be in fluid communication with the lumen at the proximal end of the catheter body. Proximal and distal debris barriers may be disposed proximally and distally of the energy delivery surfaces, respectively, and an aspiration port may be disposed between the proximal and distal barriers for removal of debris during atherosclerotic material remodeling.

The atherosclerotic material detector may include an intravascular ultrasound catheter disposed in the lumen of the catheter body, an intravascular optical coherence tomography catheter disposed in the lumen, an intravascular catheter having an MRI antenna disposed in the lumen, or the like. Alternative detectors may employ any of a variety of non-invasive imaging modalities, including external systems making use of X-rays, CT systems, non-invasive MRI or NMR systems, or the like, so that the detector may not be disposed in the blood vessel. In some embodiments, a brachytherapy catheter or other restenosis inhibitor may be advanced distally within the lumen.

The radially expandable body may comprise a plurality of flexible struts, and the energy delivery surfaces may define a circumferentially oriented array, with the energy delivery surfaces often comprising electrodes or microwave antennas. Struts of the radially expandable structure may have perforations disposed therebetween so as to define an expandable basket. The basket may have proximal and distal portions with intermediate portion disposed therebetween. The array of electrodes may be supported along the intermediate portion so as to engage adjacent atherosclerotic material when the basket is expanded within the blood vessel. The electrodes may comprise conductive surfaces of an electrode structure mounted to a separately formed basket strut. In other embodiments, electrode surfaces may be formed as part of the expandable structure. For example, the electrodes may comprise a localized widening of an associated strut, often disposed near center of a length of the strut. The expandable structure may comprise Nitinol™, and the remaining surface of the Nitinol strut may be insulated. For example, the surface may be coated with a high temperature polymer (such as a polyimide or the like). Other coatings may alternatively be used, including polyurethane. The struts may be electrically insulated from each other, so that each strut can be used to conduct energy to an electrode surface associated with the strut from a conductor extending proximally from the strut so as to independently couple each electrode surface to a controller.

A distal membrane may be deployable within the blood vessel distally of the electrode so as to inhibit distal movement of debris. A proximal membrane may be deployable proximally of the electrode so as to inhibit proximal movement of the debris. The membranes may inhibit blood interaction with the remodeling process, for example, during ablation of the atherosclerotic material. In other embodiments, power supplied to the energy delivery surfaces may be limited so as to inhibit debris generation, for example, by denaturing the atherosclerotic material, by melting of atherosclerotic material inside layers of the artery, by shrinking of atherosclerotic material inside layers of the artery (during treatment and/or in a tissue healing response), and the like. In some embodiments, the distal membrane may be supported by the distal portion of the basket so as to expand radially therewith. The proximal membrane may be supported by the proximal portion of the basket so as to expand radially therewith. At least one of the proximal and distal membranes may comprise a lumen axially off-set from the basket.

While some embodiments may have a single monopolar electrode or two or more monopolar or bipolar electrodes, the electrodes may comprise an array of at least three alternatively selectable electrodes distributed circumferentially about the axis, often comprising six or more electrodes. A controller may couple the power source to the electrode array so as to selectively energize that eccentric subset of the electrode array in response to the detected atherosclerotic material. A controller may selectively energize a subset of the energy directing surfaces by directing RF energy and/or microwave energy thereto. The atherosclerotic material detector may comprise an ultrasound transducer or optical coherence reflectrometer. Along with stand-alone structures that are insertable into a lumen of the catheter, these detectors may also be integrated into the catheter structure. A display may be coupled to the atherosclerotic material detector to show an image of circumferential atherosclerotic material thickness distributed about the catheter axis.

In another aspect, the invention provides a catheter system for eccentric remodeling and/or removal of atherosclerotic material from a blood vessel of a patient. The system comprises an elongate flexible catheter body having a proximal end and a distal end with an axis therebetween. A radially expandable structure is disposed near the distal end of the catheter body. A plurality of electrodes are oriented to be radially urged against atherosclerotic material when the expandable structure expands. An atherosclerotic material detector or imaging sensor is disposed near the distal end of the catheter body for circumferential identification and measurement of atherosclerotic material. A power source is electrically coupled to the electrodes. The power source energizes the electrodes so as to eccentrically remove and/or ablate the measured atherosclerotic material.

The catheter body will often have a lumen extending between the proximal end and the distal end. The lumen may be used as an aspiration lumen, for example, using an aspiration source in fluid communication with the lumen at the proximal end of the catheter body. Proximal and distal ablation debris barriers may be disposed proximally and distally of the electrodes, respectively, with an aspiration port disposed between the proximal and distal barriers for removal of ablation debris during atherosclerotic material ablation. The atherosclerotic material detector may comprise an ultrasound transducer of an intravascular ultrasound catheter, with the intravascular ultrasound catheter disposed in the lumen. Alternatively, other imaging modalities may be employed, including intravascular optical coherence tomography. Imaging or atherosclerotic material detecting capabilities might also be incorporated into the catheter body in some embodiments, with circumferential atherosclerotic thicknesses often being measured. An irrigation lumen may extend between the proximal end of the catheter body and the distal end of the catheter body, facilitating an enhanced local ablation environment adjacent the electrodes. A restenosis inhibitor may be advanced within the lumen, the restenosis inhibitor optionally comprising an intravascular radiation catheter, restenosis inhibiting drugs, or the like.

The radially expandable body may comprise a plurality of flexible members or struts, the electrodes optionally defining a circumferential electrode array. The struts may have perforations or openings therebetween so as to define an expandable basket. The array of electrodes may be supported along an intermediate portion of the basket and oriented radially so as to engage adjacent atherosclerotic material when the basket is expanded within a blood vessel. An aspiration port in fluid communication with an interior of the basket may facilitate removal of any ablation debris and tissue vaporization gasses, and may inhibit release of these byproducts of ablation within the blood vessel, and fluid flowing within the basket may act as a cooling fluid to limit collateral tissue damage. A distal membrane or barrier deployable within the blood vessel distally of the electrodes may inhibit distal movement of any ablation debris, while a proximal membrane or membrane deployable proximally of the electrodes may inhibit proximal movement of any ablation debris. Such member(s) may also reduce or inhibit blood flow within a localized remodeling and/or ablation environment. The distal membrane may be supported by the distal portion of the basket so as to expand radially therewith, and/or the proximal membrane may be supported by the proximal portion of the basket so as to expand radially therewith. Suitable membranes include, for example, one or more balloons axially offset from the basket within the blood vessel, or a braided superelastic material such as Nitinol™ dipped in silicone, polyurethane, PTFE, or another elastic material. In some embodiments, the membrane may be at least in part integrated with the basket.

The electrodes will often comprise an array of at least three, often comprising at least six alternatively selectable electrodes distributed circumferentially about the axis of the catheter body. The arrays of electrodes may be axisymmetric, with an eccentric treatment orientation being selected without physically rotating the array by selectively pairing electrodes of the array. A controller couples the power source to the electrode array for selectively energizing an eccentric subset of the electrode array in response to the measured atherosclerotic material. Exemplary electrodes may comprise stainless steel soldered to copper wires, with the copper wires insulated from supporting elements of associated expandable basket elements. Alternative electrodes may comprise platinum (which also allows the electrode to serve as a radiopaque marker). The electrode/basket assembly may be, for example, coated with a high temperature polymer, such as a polyimide. An exemplary electrode array includes alternating axially offset electrodes, and the controller will often direct RF bipolar power between pairs of the energized subset of electrodes, the pairs optionally comprising circumferentially offset electrodes, adjacent axially aligned electrodes, or alternating between axially and circumferentially offset electrodes. In some embodiments monopolar energy may be directed to selected electrodes, with the circuit being completed by a patient ground. More generally, each electrode will typically comprise a metallic body affixed to an adjacent strut of the expandable structure by a polymer with an associated conductor extending proximally from the electrode so as to electrically couple the electrode surface to the controller.

The exemplary atherosclerotic material detector will comprise an ultrasound transducer of an intravascular ultrasound catheter, a sensor of an intravascular optical coherence tomography catheter, or the like. A display may be provided to show an image of circumferential sclerotic material thickness about the catheter axis, the display and/or imaging catheter signals optionally comprising indicia of orientation for rotationally registering the selected electrodes to the measurements. Suitable indicia may comprise a "key" or distinguishable image of at least one expandable member or marker.

In another aspect, the invention provides a catheter for atherosclerotic material removal from the blood vessel of a patient. The catheter comprises an elongate flexible catheter body having a proximal end and a distal end with an axial aspiration lumen therebetween. A radially expandable basket near the distal end of the catheter body has a proximal portion and a distal portion with an intermediate portion disposed therebetween. A circumferential electrode array is distributed about the intermediate portion of the radially expandable basket so as to ablate adjacent atherosclerotic material when the basket expands within the blood vessel. An aspiration port provides fluid communication between the aspiration lumen and an interior of the basket. A distal membrane supported by the distal portion of the basket inhibits distal movement of ablation debris when the basket is expanded within the blood vessel. A proximal membrane supported by the proximal portion of the basket inhibits proximal movement of ablation debris when the basket is expanded within the blood vessel.

In a first method aspect, the invention provides a method for remodeling eccentric atherosclerotic material of a blood vessel of a patient. The method comprises positioning a working end of a catheter within the blood vessel adjacent the atherosclerotic material, the catheter defining an axis. The catheter is radially expanded so as to engage at least one energy delivery surface of the catheter against the atherosclerotic material. A circumferential distribution of the atherosclerotic material about the axis of the catheter is determined. Electrosurgical energy is directed from the at least one energy delivery surface eccentrically relative to the axis of the catheter in response to the determined atherosclerotic material distribution.

Remodeling of the atherosclerotic material may comprise ablation, removal, shrinkage, melting, denaturing, and/or the like of the atherosclerotic material. For example, relatively low power RF energy may be used to heat the atherosclerotic material until it melts, the material optionally being redistributed along the artery wall, inside layers of the vessel, or the like. Optionally, the atherosclerotic material may comprise a vulnerable plaque. Vulnerable plaques (and/or blood vessels in which vulnerable plaque is a concern) may be treated using RF energy to mildly heat the cap and underlying lipid-rich pool of the vulnerable plaque to a temperature in a range from about 50 to about 60° Celsius. This may be performed so as to generate thickening of the cap, often as an immune response to heating. Such thickening may potentially result in restenosis, and cap thickening and/or restenosis may be limited by accurate control of the RF energy, the use of anti-restenotic drugs (such as Rapamycin™ or the like). In addition to vulnerable plaque stabilization, the invention may be employed to eliminate vulnerable plaques, optionally by heating of the lipid-rich pool to a temperature of at least around 90° Celsius. Preferably, heating of the blood vessel will be performed so as to limit a temperature of an adventitia or outer layer of the blood vessel to below about 63° Celsius so as to inhibit collagen shrinkage and vessel collapse. In contrast, mild RF energy may be applied to the atherosclerotic material so as to denature the material and result in shrinkage of the material during or after treatment. Shrinkage of atherosclerotic material may lead to larger open vessel lumens and improved blood flow.

When remodeling of atherosclerotic plaques comprises ablation of atherosclerotic materials, any thrombolitic debris generated may be restrained and/or evacuated. Where ablation generates non-thrombolitic debris, or where remodeling is performed so as to inhibit debris generation, debris restraining and evacuation may be unnecessary.

Electrosurgical energy directed by the one or more energy delivery surfaces will often comprise RF and/or microwave electrical energy. The circumferential distribution of atherosclerotic material may be determined using intravascular or non-invasive techniques. The electrosurgical energy may be directed eccentrically without rotating the energy delivery surfaces about the catheter axis by energizing a subset of the electrodes. The subset of electrodes may be selected in response to the determined atherosclerotic material distribution. Selected electrodes may be rotationally registered with the atherosclerotic material distribution, for example, with reference to one or more structures of the expandable basket having a distinguishable image. For example, a strut of the electrode arbitrarily identified as electrode 1 may have one radiopaque marker or other distinguishable image, and a strut of an electrode referenced as electrode 2 may have two radiopaque markers or two distinguishable image features. This can help identify all of the electrodes, since electrode 1 is identifiable and the direction from electrode 1 to electrode 2 indicates a circumferential electrode count direction. A variety of alternative distinguishable features with integrated or separate circumferential electrode count orientation indicators may also be utilized. In some embodiments, registration may be performed automatically with reference to an electronic signal.

In yet another aspect, the invention provides a method for eccentric atherosclerotic material removal from a blood vessel of a patient. The method comprises positioning a working end of the catheter within the blood vessel and adjacent the atherosclerotic material. The catheter defines the axis. The catheter is radially expanded so as to engage a plurality of electrodes of the catheter against the atherosclerotic material. A circumferential distribution of the atherosclerotic material is measured about the axis of the catheter. RF energy is directed from the electrodes eccentrically relative to the axis of the catheter in response to the measured atherosclerotic material distribution.

BRIEF DESCRIPTION OF THE DRAWINGS

FIG. 7C illustrates an alternative basket and debris barrier.

DETAILED DESCRIPTION OF THE INVENTION

Figure 1A:
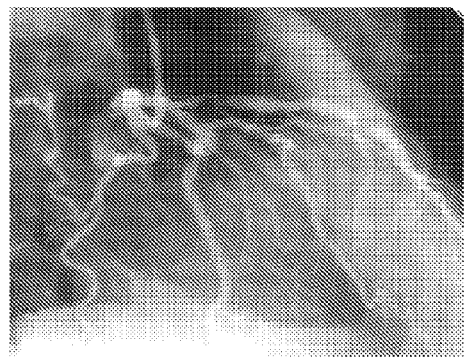
FIG. 1A illustrates diffuse atherosclerotic disease in which a substantial length of multiple blood vessels has limited effective diameters.

The present invention provides devices, systems, and methods to remodel a partially occluded artery in order to open the artery lumen and increase blood flow. Remodeling may involve the application of electrosurgical energy, typically in the form of RF and/or microwave electrical potentials to energy delivery surfaces such as electrodes, antennas, and the like. This energy will often be controlled so as to limit a temperature of target and/or collateral tissues, for example, limiting the heating of a fibrous cap of a vulnerable plaque or the intimal layer of an artery structure to a maximum structure in a range from about 50 to about 60° Celsius, by limiting the maximum temperature of an outer layer or adventitia of the blood vessel to no more than about 63° Celsius, limiting heating of a lipid-rich pool of a vulnerable plaque sufficiently to induce melting of the lipid pool while inhibiting heating of other tissues (such as an intimal layer or fibrous cap) to less than a temperature in a range from about 50 to about 60° Celsius so as to inhibit an immune response that might otherwise lead to restenosis, or the like. Relatively mild heating energies may be sufficient to denature and shrink atherosclerotic material during treatment, immediately after treatment, and/or more than one hour, more than one day, more than one week, or even more than one month after the treatment through a healing response of the tissue to the treatment so as to provide a bigger vessel lumen and improved blood flow.

In some embodiments, remodeling of the atherosclerotic plaque may comprise the use of higher energies to ablate and remove occlusive material from within body lumens, and particularly to remove atherosclerotic material from a blood vessel in order to improve blood flow. Ablation debris may be generated by such ablation, and the ablation debris may be thrombolitic or non-thrombolitic. Where thrombolitic debris is generated by ablation, that debris may be restrained, captured, and/or evacuated from the treatment site. Non-thrombolitic debris produced by ablation may not have to be restrained and/or evacuated from the vessel. The techniques of the invention will often provide electrosurgical capabilities, sensing or imaging suitable for measuring atheroma and/or vascular walls, and/or an emboli inhibitor. As atherosclerosis may be eccentric relative to an axis of the blood vessel over 50% of the time, possibly in as much as (or even more than) 75% of cases, the devices and methods of the present invention will often be particularly well suited for directing treatment eccentrically, often in response to circumferential atherosclerotic material detecting or imaging. While the methods and devices described herein allow such eccentric treatments, the devices can also be used for treatment of radially symmetric atherosclerosis by selectively directing energy in a radially symmetric pattern about an axis of the catheter or the like.

Hence, remodeling of atherosclerotic materials may comprise ablation, removal, shrinkage, melting, and the like of atherosclerotic and other plaques. Optionally, atherosclerotic material within the layers of an artery may be denatured so as to improve blood flow, so that debris will not necessarily be generated. Similarly, atherosclerotic materials within the arterial layers may be melted and/or treatment may involve a shrinking of atherosclerotic materials within the artery layers, again without necessarily generating treatment debris. The invention may also provide particular advantages for treatment of vulnerable plaques or blood vessels in which vulnerable plaque is a concern. Such vulnerable plaques may comprise eccentric lesions, and the present invention may be particularly well suited for identifying an orientation (as well as axial location) of the vulnerable plaque structure. The invention will also find applications for targeting the cap structure for mild heating (to induce thickening of the cap and make the plaque less vulnerable to rupture) and/or heating of the lipid-rich pool of the vulnerable plaque (so as to remodel, denature, melt, shrink, and/or redistribute the lipid-rich pool.

While the present invention may be used in combination with stenting and/or balloon dilation, the present invention is particularly well suited for increasing the open diameter of blood vessels in which stenting and balloon angioplasty are not a viable option. Potential applications include treatment of diffuse disease, in which atherosclerosis is spread along a significant length of an artery rather than being localized in one area. The invention may also provide advantages in treatment of vulnerable plaque or blood vessels in which vulnerable plaque is a concern, both by potentially identifying and avoiding treatment of the vulnerable plaque with selected eccentric and/or axial treatments separated from the vulnerable plaque, and by intentionally ablating and aspirating the cap and lipid-rich pool of the vulnerable plaque within a controlled environmental zone or region within the blood vessel lumen. The invention may also find advantageous use for treatment of tortuous, sharply-curved vessels, as no stent need be advanced into or expanded within the sharp bends of many blood vessel. Still further advantageous applications include treatment along bifurcations (where side branch blockage may be an issue) and in the peripheral extremities such as the legs, feet, and arms (where crushing and/or stent fracture failure may be problematic).

Figure 1B:
FIG. 1B illustrates vulnerable plaque within a blood vessel.
Figure 1C:
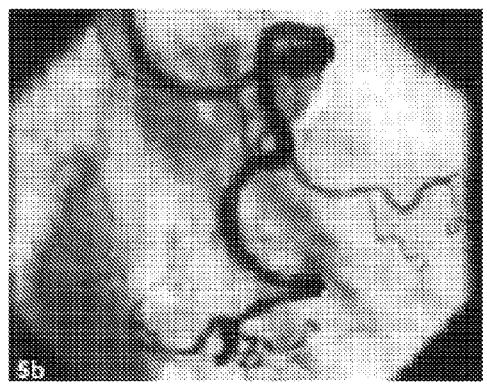
FIG. 1C illustrates the sharp bends or tortuosity of some blood vessels.
Figure 1D:
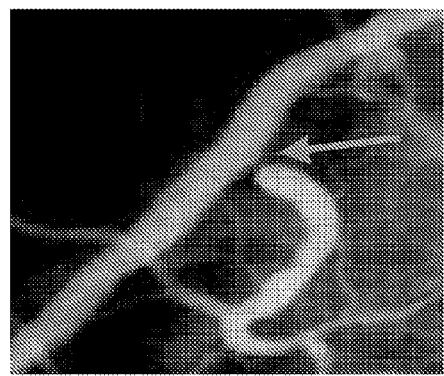
FIG. 1D illustrates atherosclerotic disease at a bifurcation.
Figure 1E:
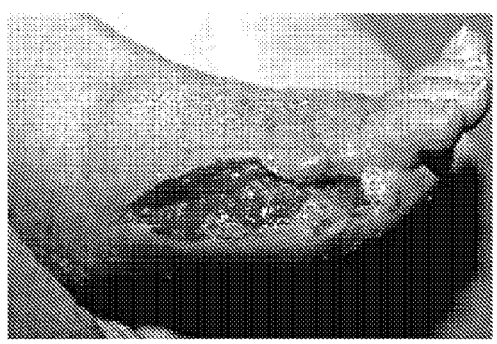
FIG. 1E illustrates a lesion associated with atherosclerotic disease of the extremities.

Diffuse disease and vulnerable plaque are illustrated in FIGS. 1A and 1B, respectively. FIG. 1C illustrates vascular tortuosity. FIG. 1D illustrates atherosclerotic material at a bifurcation, while FIG. 1E illustrates a lesion which can result from atherosclerotic disease of the extremities.

Figure 1F:
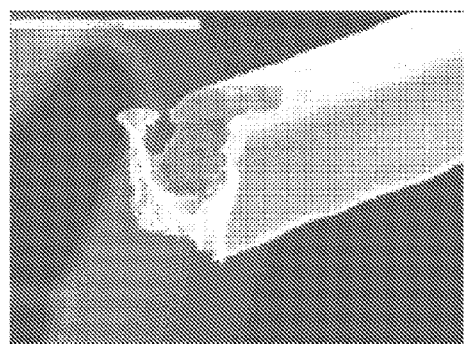
FIG. 1F is an illustration of a stent fracture or corrosion.

FIG. 1F illustrates a stent structural member fracture which may result from corrosion and/or fatigue. Stents may, for example, be designed for a ten-year implant life. As the population of stent recipients lives longer, it becomes increasingly likely that at least some of these stents will remain implanted for times longer than their designed life. As with any metal in a corrosive body environment, material degradation may occur. As the metal weakens from corrosion, the stent may fracture. As metal stents corrode, they may also generate foreign body reaction and byproducts which may irritate adjoining body tissue. Such scar tissue may, for example, result in eventual reclosure or restenosis of the artery.

Figure 1G:
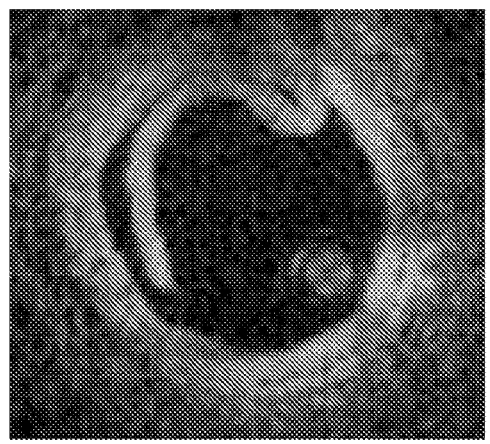
FIG. 1G illustrates a dissection within a blood vessel.
Figure 1H:
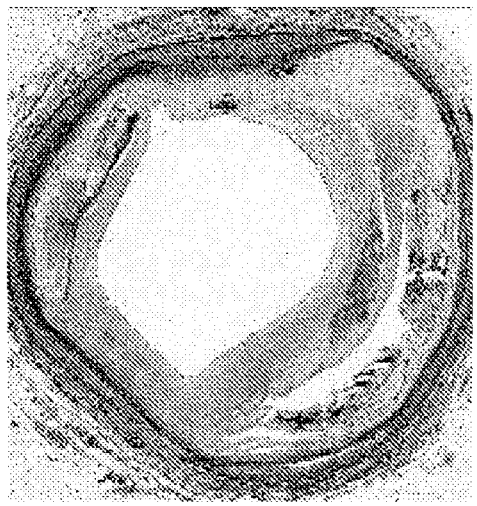
FIG. 1H illustrates a circumferential measurement of an artery wall around a healthy artery.
Figure 1I:
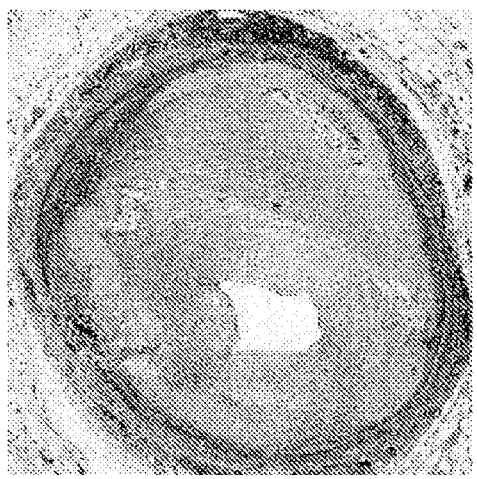
FIG. 1I illustrates circumferential distribution of atheroma about a restenosed artery.

Arterial dissection and restenosis may be understood with reference to FIGS. 1G through 1I. The artery comprises three layers, an endothelial layer, a medial layer, and an adventitial layer. During angioplasty, the inside layer may delaminate or detach partially from the wall so as to form a dissection as illustrated in FIG. 1G. Such dissections divert and may obstruct blood flow. As can be understood by comparing FIGS. 1H and 1I, angioplasty is a relatively aggressive procedure which may injure the tissue of the blood vessel. In response to this injury, in response to the presence of a stent, and/or in the continuing progression of the original atherosclerotic disease, the opened artery may restenose or subsequently decrease in diameter as illustrated in FIG. 1I. While drug eluting stents have been shown to reduce restenosis, the efficacy of these new structures several years after implantation has not be fully studied, and such drug eluting stents are not applicable in many blood vessels.

In general, the present invention provides a catheter which is relatively quick and easy to use by the physician. The catheter system of the present invention may allow arteries to be opened to at least 85% of their nominal or native artery diameter. In some embodiments, arteries may be opened to about 85%, and/or acute openings may be less than 85%. Rapid occlusive material removal may be effected using sufficient power to heat tissues locally to over about 100° C. so as to vaporize tissues, or more gentle remodeling may be employed.

The desired opening diameters may be achieved immediately after treatment by the catheter system in some embodiments. Alternatively, a milder ablation may be implemented, for example, providing to no more than a 50% native diameter when treatment is complete, but may still provide as much as 80 or even 85% or more native vessel open diameters after a subsequent healing process is complete, due to resorption of injured luminal tissues in a manner analogous to left ventricular ablation for arrhythmia and transurethral prostate (TURP) treatments. Such embodiments may heat at least some occlusive tissue to a temperature in a range from about 55° C. to about 80° C. In some embodiments, occlusive tissues may be heated to a maximum temperature in a range between about 93 and 95° C. In other embodiments described herein, heating may be controlled so as to provide tissue temperatures in a range between about 50 and 60° C., with some embodiments benefiting from maximum tissue temperatures of about 63° C. Still further treatments may benefit from treatment temperatures of about 90° C. Advantageously, the catheter systems and methods of the invention may be used without balloon angioplasty, thereby avoiding dissections and potentially limiting restenosis.

Figure 2:
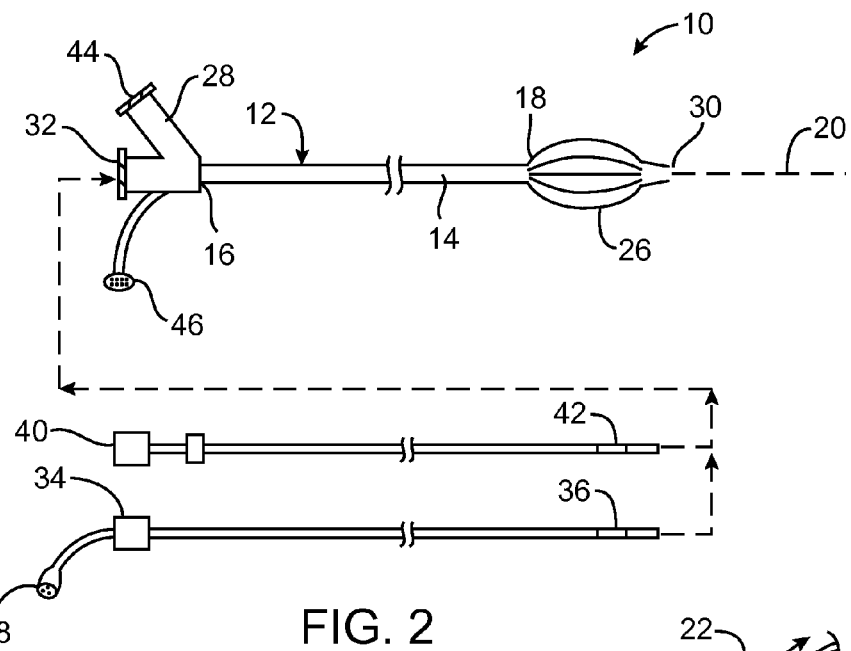
FIG. 2 schematically illustrates an atherosclerotic material catheter system according to the present invention.
Figure 2A:
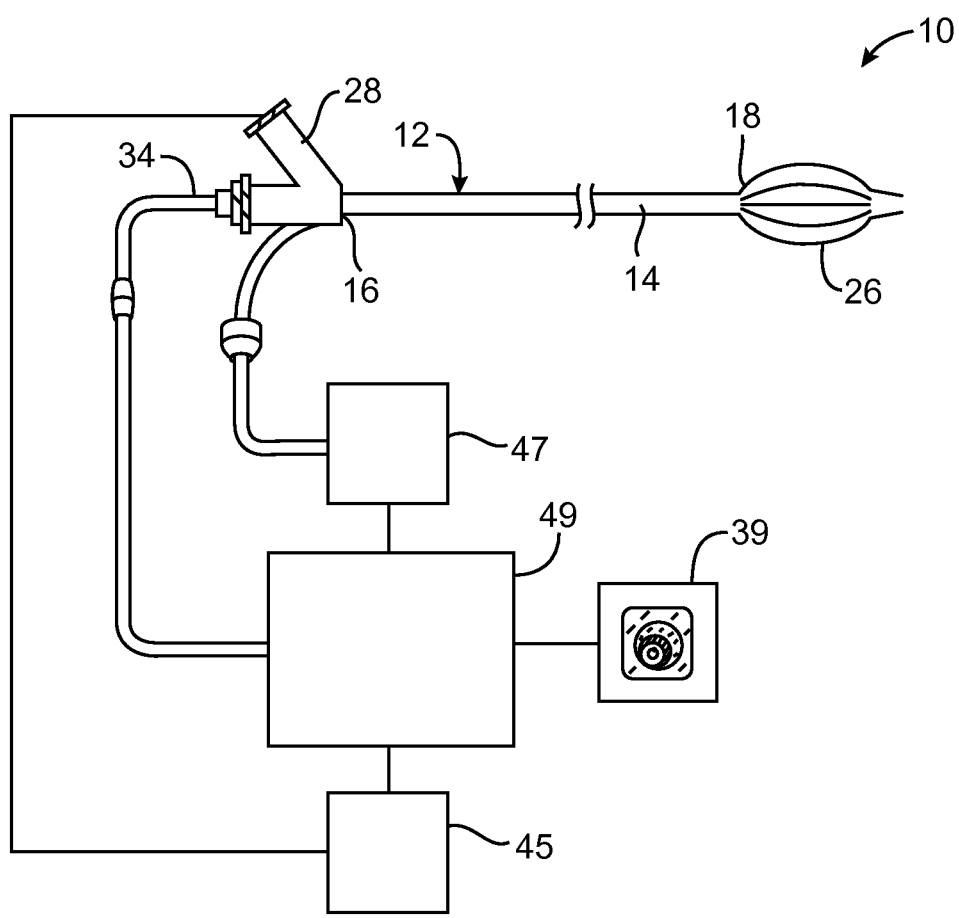
FIG. 2A schematically illustrates a catheter system for remodeling atherosclerotic material, the system including the catheter of FIG. 2.

An exemplary catheter system 10 is schematically illustrated in FIGS. 2 and 2A. A remodeling and/or ablation catheter 12 includes a catheter body 14 having a proximal end 16 and a distal end 18. Catheter body 14 is flexible and defines a catheter axis 20, and includes an aspiration lumen 22 and an irrigation lumen 24 (see FIG. 3). Still further lumens may be provided for a guidewire, imaging system, or the like as described below. Lumen 22 may be used for sensing and/or imaging of atheroma as well as aspiration.

Catheter 12 includes a radially expandable structure 26 adjacent distal end 18 and a housing 28 adjacent proximal end 16. A distal tip 30 may include an integral tip valve to seal aspiration lumen 22 and allow passage of guidewires, imaging and/or restenosis inhibiting catheters, and the like.

Proximal housing 28 includes a first connector 32 in fluid communication with aspiration lumen 22. Aspiration lumen 22 may have an aspiration port within expandable structure 26 so as to allow aspiration or aspiration of debris and gasses from within the expandable structure. Aspiration lumen 22 may also be used as an access lumen for guidewires, intravascular imaging catheters, and/or distally advancing intravascular radiation treatment catheters or restenosis inhibiting drugs. Hence, connector 32 may selectively accommodate an imaging catheter 34 having an atherosclerotic material detector 36 advancable within catheter body 14 adjacent to and/or beyond distal end 18, the detector often comprising an intravascular ultrasound transducer, an optical coherent tomography sensor, an MRI antenna, or the like. An imaging connector 38 of imaging catheter 34 transmits imaging signals allowing circumferential measurement of atherosclerotic thicknesses about axis 20 to a display 39.

Connector 32 also accommodates a restenosis inhibiting treatment catheter 40, the treatment catheter here comprising an intravascular radiation catheter. Such a radiation catheter may include a radiation source 42 which can again be advanced distally within catheter body 14 to or beyond expandable structure 26.

Figure 3:
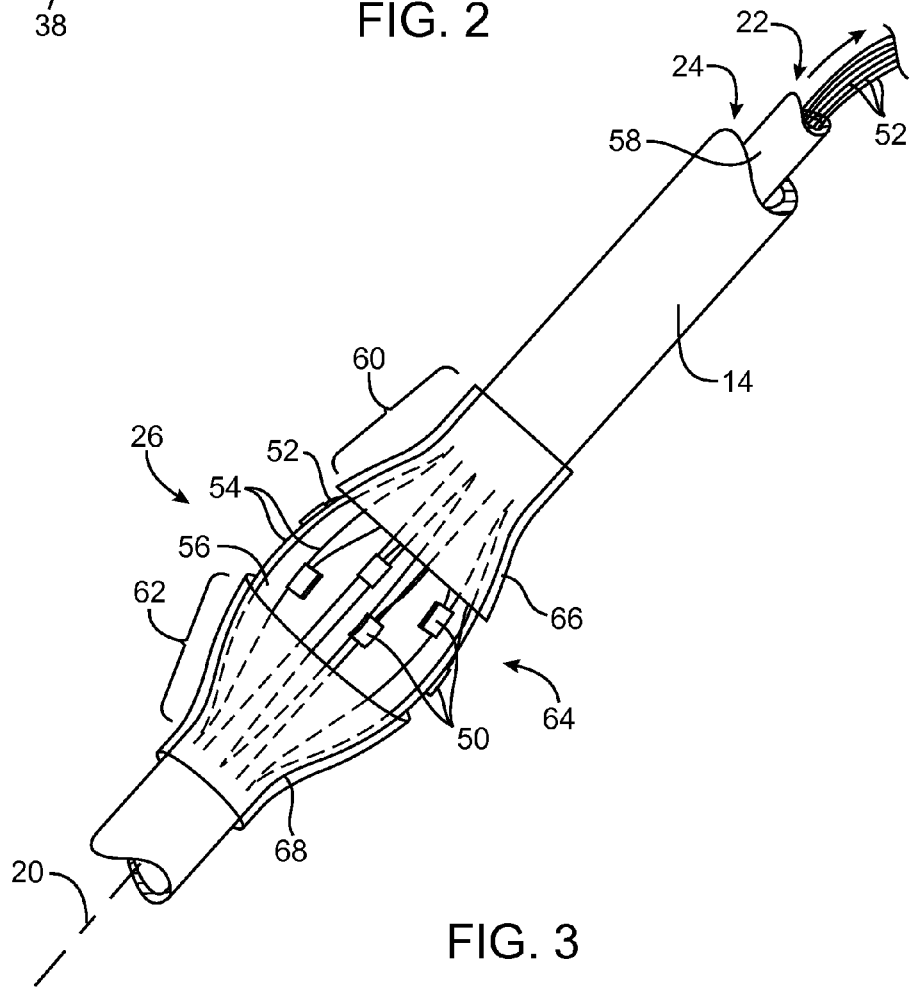
FIG. 3 illustrates an expandable basket and an associated electrode array of the catheter system of FIG. 2.

A second connector 44 of proximal housing 28 is in fluid communication with irrigation lumen 24 (see FIG. 3). Second connector 44 may be coupled to an irrigation fluid source for introducing conductive or non-conductive liquids, gases, or the like, ideally for introducing gas or heparinized saline. Both first and second connectors 32, 44 may optionally comprise a standard connector such as a Luer-Loc™ connector. In FIG. 2A connector 44 is schematically shown coupled to an aspiration vacuum source/infusion fluid source 45.

Referring now to FIGS. 2, 2A, and 3, proximal housing 28 also accommodates an electrical connector 46. Connector 46 includes a plurality of electrical connections, each electrically coupled to an electrode 50 via a dedicated conductor 52. This allows a subset of electrodes 50 to be easily energized, the electrodes often being energized with bipolar or monopolar RF energy. Hence, electrical connector 46 will often be coupled to an RF generator via a controller 47, with the controller allowing energy to be selectively directed to an eccentric portion of an engaged luminal wall. When monopolar RF energy is employed, patient ground may (for example) be provided by an external electrode or an electrode on catheter body 14. A processor 49 may manipulate signals from imaging catheter 34 to generate an image on display 39, may coordinate aspiration, irrigation, and/or treatment, and may automatically register the treatment with the image.

Expandable structure 26 is illustrated in more detail in FIG. 3. Expandable structure 26 may expand resiliently when released from within a restraining sheath, or may expand by pulling tip 30 toward distal end 18 (see FIG. 2), optionally using a pullwire, an inner catheter body 58, or the like. Expandable structure 26 here comprises a perforate structure or basket having a series of structural struts or elements 54 with opening or perforations 56 therebetween. Perforations 56 may be formed, for example, by cutting elongate slits in a flexible tube material, or the basket may be formed by braiding elongate wires or ribbons or the like.

Expandable structure 26 generally includes a proximal portion 60, a distal portion 62, and an intermediate portion 64 therebetween. Each electrode 50 is mounted on an associated basket element 54 along intermediate portion 64, with an associated conductor 52 extending proximally from the electrode. Electrodes 50 are distributed circumferentially about axis 20 in an array, adjacent electrodes preferably being axially offset, ideally being staggered or alternating between proximal and distal axial locations. This allows bipolar energy to be directed between adjacent circumferential (axially offset) electrodes between adjacent distal electrodes, between adjacent proximal electrodes, and the like.

Figure 12:
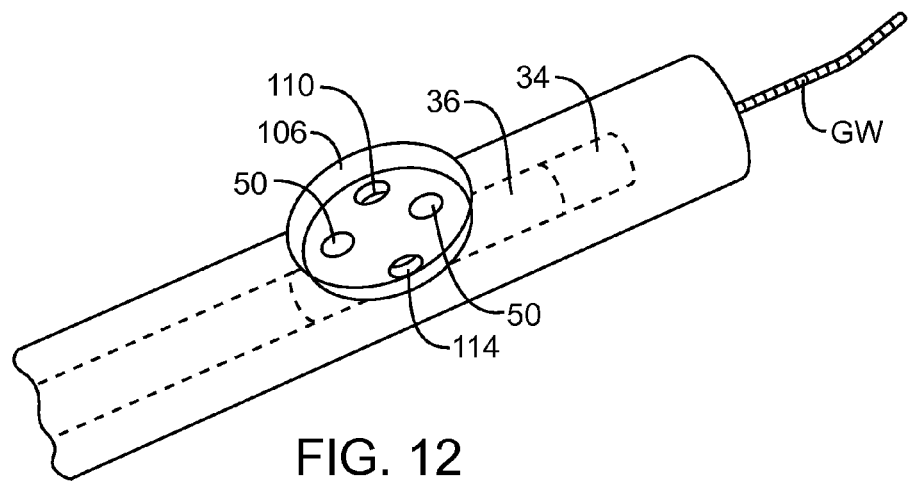
FIGS. 11-21 schematically illustrate alternative catheters and catheter systems for use in the methods described herein.
Figure 11:
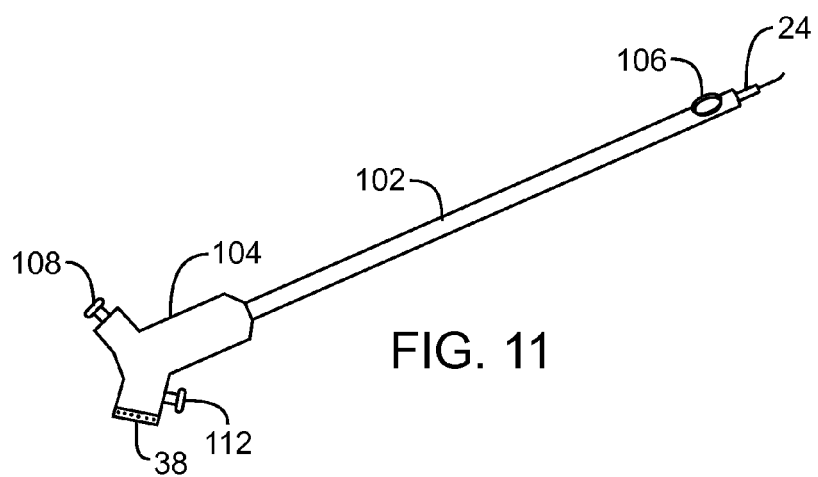
Figure 13:
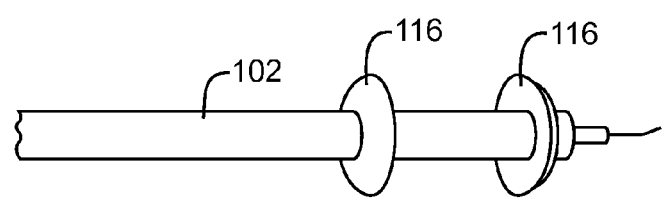

In the exemplary embodiment, proximal and distal barriers 66, 68 expand radially with proximal and distal portions 60, 62 of expandable structure 26. Barriers 66, 68 inhibit any ablation debris and gases generated adjacent electrodes 50 from traveling within the body lumen beyond catheter 12. Barriers 66, 68 also allow an at least partially isolated ablation environment to be established within the body lumen, for example, by replacing blood within a blood vessel with a more advantageous fluid environment for limiting charring of the electrodes and the like. Alternative barriers may be provided instead of (or in combination with) barriers 66, 68, including one or more balloons axially offset from expandable member 26, elastic lips as shown in FIG. 11-13, or the like. In other embodiments remodeling may be effected without generating significant thermolytic ablation debris and/or a desired treatment environment may be provided with localized irrigation and/or aspiration flows so that some systems may forego the use of barriers.

Figure 4:
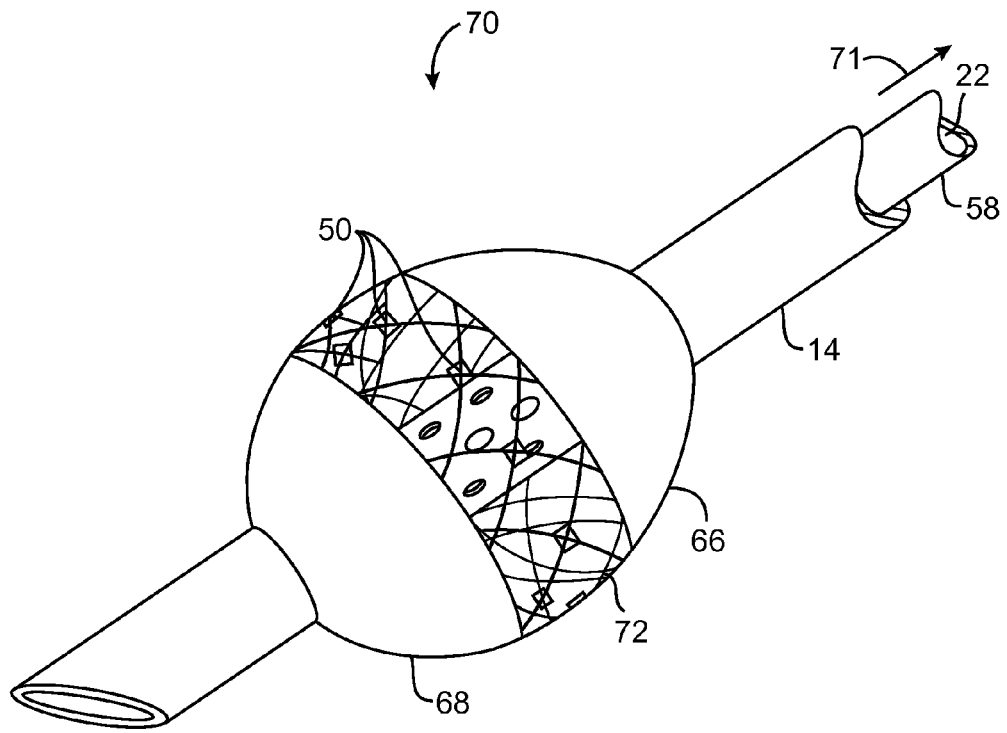
FIGS. 4 and 5 illustrate alternative basket structures for use with the catheter system of FIG. 2.
Figure 5:
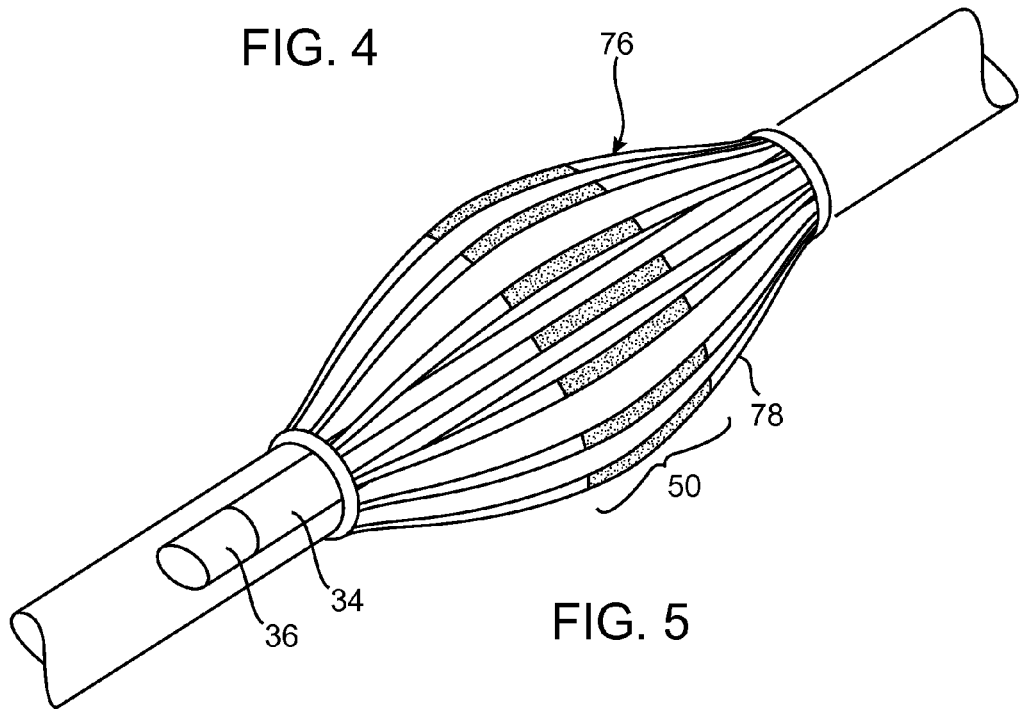
Figure 6A:
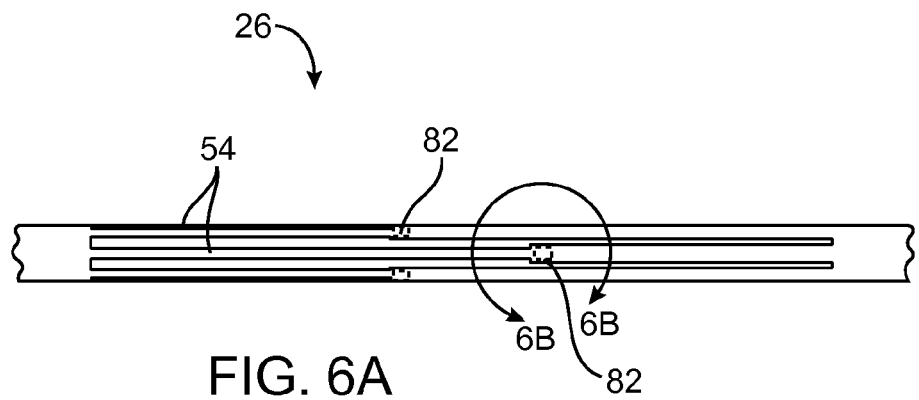
FIGS. 6A and 6B illustrate an exemplary basket structure having alternating axially offset electrodes in a circumferential array.

Referring now to FIGS. 4 and 6A, alternative embodiments may use different expandable structures in the form of different baskets. In FIG. 4, a braided basket 70 includes electrodes 50 mounted on braided structures 72. While metallic braided structures may be used in some embodiments with attention to electrical isolation of the electrodes, shorting of crossing metallic braided structures may be problematic. Hence, braided members 72 may comprise a high-temperature polymer or non-conductive material such as polyimide. An elongate electrode basket 76 may include electrodes 50 formed, for example, by selectively exposing a metallic surface along a central portion of basket member 78, while the remainder of the basket element is electrically isolated using a high-temperature polymer or the like so that the basket struts may be used as a conductor for energizing the electrode. Radial expansion of basket 76 is also illustrated by movement 71 of inner catheter body 58 relative to body 14. Expansion may also be effected by withdrawing a sleeve from over the basket, a pull wire, or the like. An intravascular ultrasound image sensor 36 of imaging catheter 34 is illustrated in FIG. 5 distal of expandable structures 76, with a proximal portion of the imaging catheter removed for clarity. Still further alternative expandable structures may be employed, including systems in which an array of electrodes is mounted circumferentially about a balloon, which may reduce blood contamination in the ablation area. Alternatively, a controlled ablation environment may be maintained with barriers proximally and/or distally of the expandable member by axially offset balloons, with an optional aspiration port again being disposed between such proximal and distal barriers.

Figure 6B:
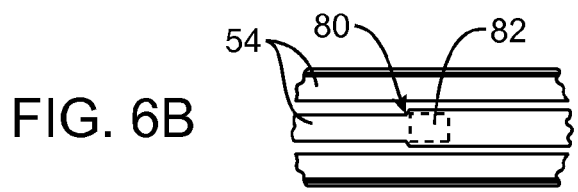

An exemplary expandable structure 26 is formed by cutting slots in a superelastic alloy tube such as a nickel titanium alloy or Nitinol™ tube. As can be understood with reference to FIG. 6B, expandable structures 54 may have circumferential widths 80 which are enhanced adjacent an electrode and/or electrode mounting location 82. As can be seen in FIG. 6A, the localized enhancement of the width 80 adjacent electrode mounting pads 82 may be axially offset, as described above. The slots forming expandable members 54, and hence the expandable members themselves may, for example, be 0.8 inches in length, with the expandable members having a circumferential width of about 0.25 inches.

Figure 7A:
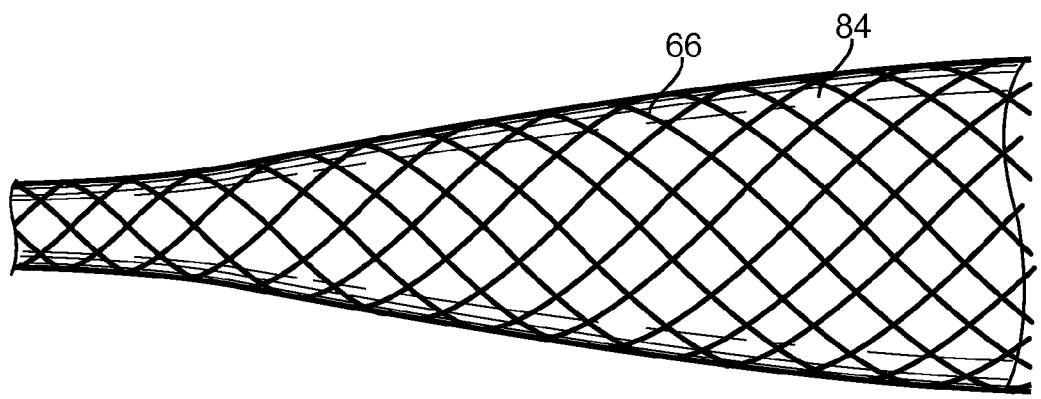
FIGS. 7A and 7B illustrate an exemplary ablation debris barrier for use with a basket.
Figure 7B:
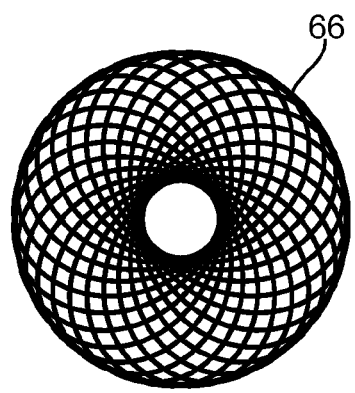

Referring now to FIGS. 7A and 7B, side and end views of an expandable barrier in the form of a collapsible cone can be seen. Barrier 66 here comprises a braided Nitinol™ wire 84 coated in silicone, for example, by dipping a braid of a superelastic alloy such as a Nitinol™ braid in liquid silicone and allowing it to harden. Such cones may then be mounted over the proximal and distal portions of the expandable structure. As noted above, a variety of alternative barrier membranes may be employed. FIG. 7C illustrates a basket 75 with an integral barrier 77 coated directly on the basket. Barrier 77 comprises a polyurethane, which may be quite tear resistant. Alternative barrier membranes may comprise other materials such as PTFE or the like.

Figure 8:
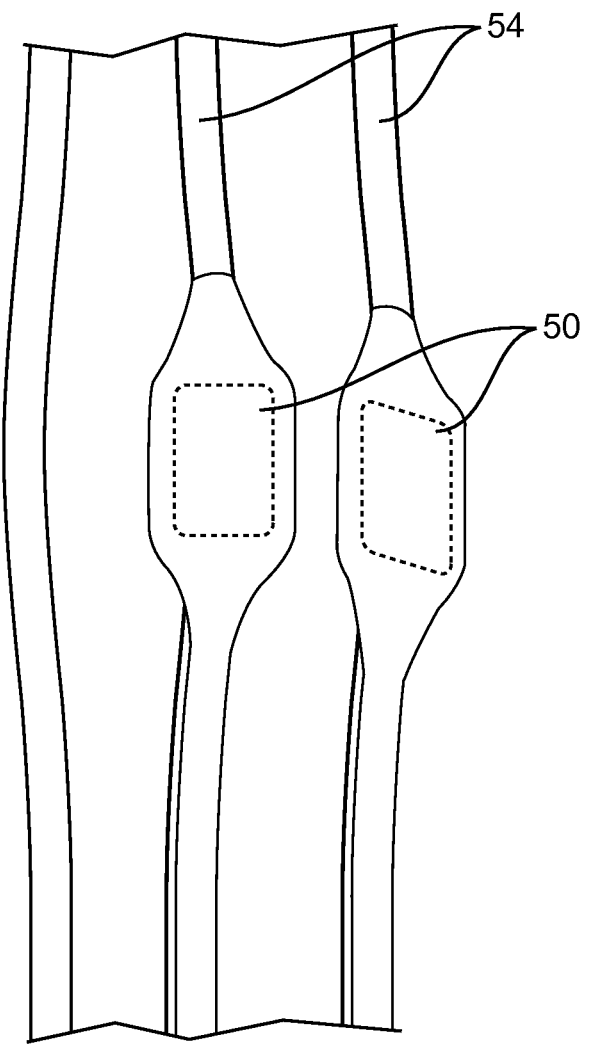
FIG. 8 illustrates electrodes having dedicated conductors mounted to associated elements of a superelastic metal basket.
Figure 9:
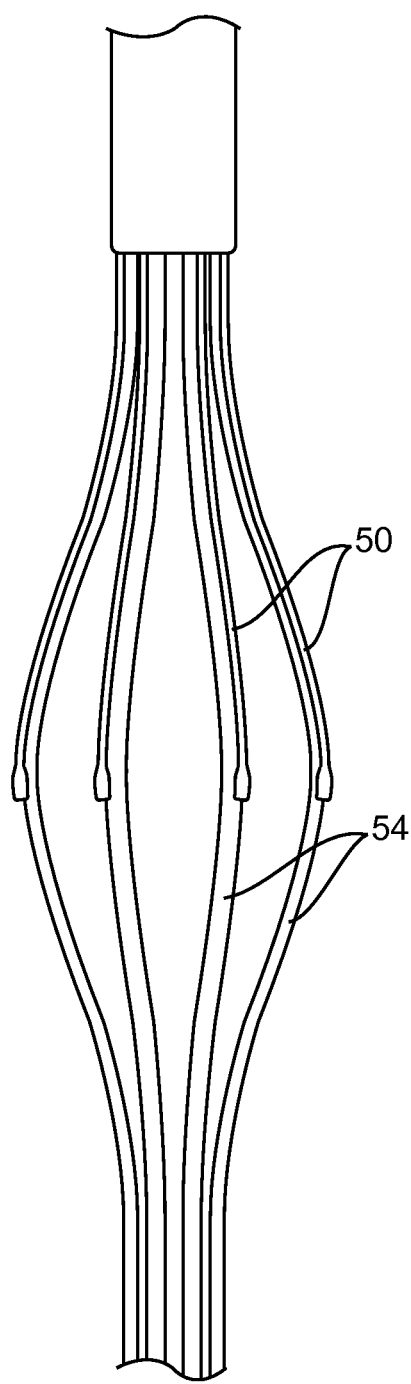
FIG. 9 is an illustration of a basket comprising polyimide supporting a circumferential array of electrodes.

Referring now to FIGS. 8 and 9, exemplary electrodes 50 supported by polyimide alloy expandable members 54 may be coated with a high-temperature polymer. Conductors 52 extend proximally from electrodes 50 as described above. High contrast radiopaque markers such as gold, platinum, platinum/iridium alloy, and the like may be attached to or near these struts. The markers could also be used as the electrodes.

Figure 10A:
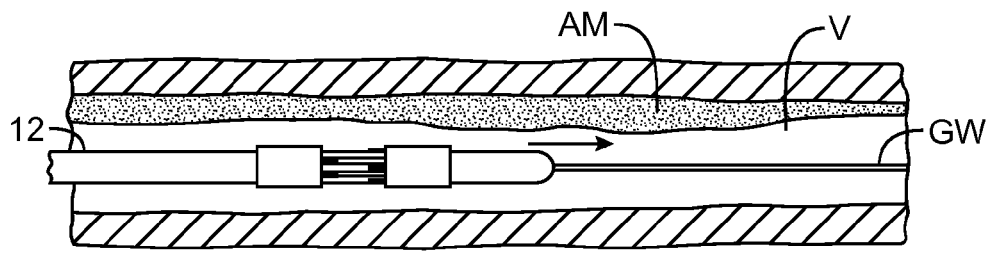
FIGS. 10A-E illustrate an exemplary atherosclerotic material remodeling and/or removal method using the catheter system of FIG. 2.

The use of catheter system 10 for remodeling and/or removal of eccentric atheroma from within a blood vessel can be understood with reference to FIGS. 10A through 10E. As seen in FIG. 10A, accessing of a treatment site will often involve advancing a guidewire GW within a blood vessel V at, and more often distally beyond a target region of atherosclerotic material AM. A wide variety of guidewires may be used. For accessing a vessel having a total occlusion, guidewire GW may comprise any commercially available guidewire suitable for crossing such a total occlusion, including the Safe-Cross™ RF system guidewire having forward-looking optical coherence reflectrometry and RF ablation. Where atherosclerotic material AM does not result in total occlusion of the lumen, such capabilities need not be provided in guidewire GW, although other advantageous features may be provided. For example, guidewire GW may include a distal balloon to hold the guidewire in place and further inhibit movement of ablation debris and the like. Guidewire GW may be positioned under fluoroscopic (or other) imaging.

Figure 10B:
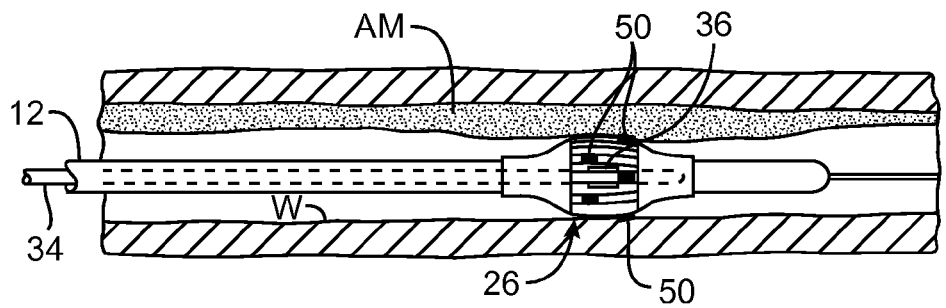

Catheter 12 is advanced distally over guidewire GW and positioned adjacent to atherosclerotic material AM, often toward a distal portion of the occlusion as can be understood with reference to FIGS. 10A and 10B. Expandable structure 26 expands radially within the lumen of the blood vessel so that electrodes 50 radially engage atherosclerotic material AM. Expandable structure 26 may be expanded by, for example, pulling a pullwire extending through catheter body 14 to the coupled (directly or indirectly) to distal portion 62 of expandable body 26 (see FIG. 3). Alternatively, an inner catheter body 58 may be moved proximally relative to outer catheter body 14, with the inner catheter again being coupled to the distal portion of the expandable body. Still further alternatives are possible, including withdrawing a sheath from around the expandable body and allowing the expandable body to flex radially outwardly. In at least some embodiments, whether actuated from the proximal end of catheter 12 or simply by releasing the expandable body, the structural members defining the expandable body may comprise elastic or superelastic materials treated to expand radially outwardly, such as by heat-setting a superelastic Nitinol™ metal, polyimide, or the like. In some embodiments, guidewire GW may be removed after the ablation catheter is positioned and/or the basket is expanded. As atherosclerotic material AM is distributed eccentrically about catheter 12, some of electrodes 50 directly engage a luminal wall W, as can be understood with reference to FIGS. 10B and 10C.

Figure 10C:
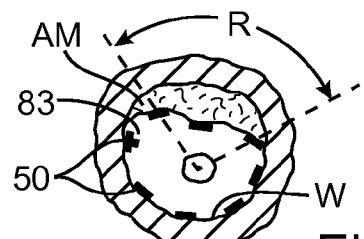

Imaging catheter 34 is positioned within a lumen of catheter 12 so that detector 42 extends to adjacent atherosclerotic material AM. The imaging catheter operates within and/or through catheter 12 so as to measure a thickness of atherosclerotic material concentrically about catheter 12 as illustrated in FIG. 10C with measurements often being taken at a plurality of axial locations so as to measure axial variation of the atherosclerotic material AM within the blood vessel, such measurements often progressing proximally. In many cases, atherosclerotic material AM will be distributed eccentrically within the vessel wall as shown in FIG. 10C. It should be noted that no portion of the vessel wall need be completely uncovered by atherosclerotic material for the measurement distribution to indicate that the obstruction is eccentric, as a relatively thin layer of atheroma along one portion or side of the blood vessel may be much different in thickness than a very thick layer of atherosclerotic material on an opposite side of the blood vessel V. In some methods, remodeling and/or ablation of all atheroma along one side may result in electrode/vessel wall engagement only after treatment begins.

In some cases, imaging catheter 34 may allow identification and/or characterization of atherosclerotic materials, plaques, tissues, lesions, and the like from within a blood vessel. For example, imaging catheter 34 may determine an axial and/or circumferential localization of a target plaque for treatment. Where treatments are intended for atherosclerotic plaques so as to enhance blood flow through the lumen, the treatment may be tailored to provide short term and/or long term increases in lumen diameter and blood flow. Where catheter 34 identifies a circumferentially and/or axially localized vulnerable plaque, that vulnerable plaque may be targeted for a suitable treatment to inhibit deleterious release of thrombolitic materials, often by thickening a fibrous cap of the vulnerable plaque, making the plaque less vulnerable to rupture, decreasing a size or danger of release from a lipid-rich pool of the vulnerable plaque, or the like. Hence, catheter 34 may be used to provide information similar to that available through histology so as to indicate a composition of an atheroma (by identifying and location, for example, a fibrous cap, smooth muscle cells, a lipid pool, calcifications, and the like.) Intravascular ultrasound catheters may now be capable of such atheroma characterizations, and these characterizations may also be provided by optical coherence tomography intravascular catheters, intravascular MRI antennas, and other catheter-based imaging systems, or by non-invasive imaging modalities such as MRI systems, and the like.

Suitable imaging catheters for use in the present catheter system are commercially available from a wide variety of manufacturers. Suitable technology and/or catheters may, for example, be commercially available from SciMed Life Systems and Jomed-Volcano Therapeutics (providers of intravascular ultrasound catheters), Light Lab™ Imaging (developing and commercializing optical coherence tomography catheters for intravascular imaging), Medtronic Cardio-Rhythm, and the like. Still further alternative technologies may be used, including ultra fast magnetic resonance imaging (MRI), electrical impedance atheroma depth measurements, optical coherence reflectrometry, and the like.

The systems, devices, and methods described herein may optionally make use of imaging techniques and/or atherosclerotic material detector devices which are at least in part (optionally being entirely) disposed outside of the body lumen, optionally being disposed outside of the patient body. Non-invasive imaging modalities which may be employed include X-ray or fluoroscopy systems, MRI systems, external ultrasound transducers, and the like. Optionally, external and/or intravascular atherosclerotic material detectors may also be used to provide temperature information. For example, a system having an MRI antenna may detect tissue temperatures such that a graphical indication of treatment penetration may be presented on the system display. Tissue temperature information may also be available from ultrasound and/or optical coherence tomography systems, and the temperature information may be used as feedback for directing ongoing treatments, for selecting tissues for treatment (for example, by identifying a hot or vulnerable plaque), and the like.

As with positioning of guidewire GW and advancement of catheter 12, positioning of sensor 30 of imaging catheter 34 may be facilitated by fluoroscopic or other imaging modalities. Location of sensor 36 relative to expandable structure 26 may be facilitated by radiopaque markers of catheter 34 adjacent sensor 36, and by the radiopaque structure (or corresponding radiopaque markers placed on or near) expandable structure 26, and/or by the use of radiopaque electrodes.

By expanding expandable structure 26 within blood vessel V, optional proximal and distal barriers 66, 68 (see FIG. 3) may form an at least partially, and preferably a substantially isolated environment within the blood vessel. That environment may be adapted to improve subsequent remodeling and/or ablation by aspirating blood from a port of aspiration lumen 22 disposed between proximal and distal barriers 66, 68, and by irrigating the isolated environment with a desired fluid, as described above. When provided, aspiration and/or irrigation may be performed, optionally simultaneously, so as to generate a flow within the controlled environment for removal of any vaporization gases, ablation debris, and the like.

Figure 10D:
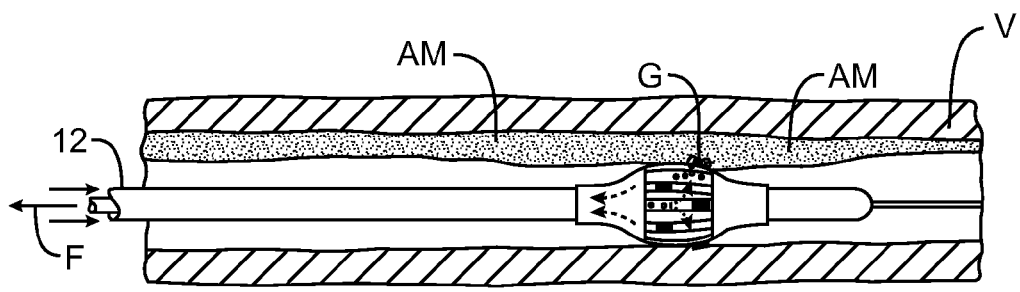

Referring now to FIGS. 10C and 10D, circumferential imaging often indicates that remodeling and/or ablation should be targeted to an eccentric portion or region R of the vessel wall W. To aid in registering the electrodes with the circumferential atheroma distribution, one strut of expandable structure 26 has an identifiable image, allowing the strut to serve as a rotational alignment key. Registering the electrodes may be achieved using intravascular imaging such as intravascular ultrasound (IVUS), optical coherence tomography ("OCT"), intravascular MRI, and/or the like, optionally using external imaging such as fluoroscopy, magnetic resonance imaging ("MRI"), or the like. Electronic registration may also be used. In response to this information, RF energy is directed to electrodes within region R. These actively energized electrodes define a subset of the overall array of electrodes, and selection of this subset of electrodes may be implemented using a controller as described hereinbelow.

The mechanisms of ablating atherosclerotic material within a blood vessel have been well described, including by Slager et al. in an article entitled, "*Vaporization of Atherosclerotic Plaque by Spark Erosion*" in *J. of Amer. Cardiol.* (June, 1985), on pp. 1382-6; and by Stephen M. Fry in "*Thermal and Disruptive Angioplasty: a Physician's Guide*;" Strategic Business Development, Inc., (1990) the full disclosures of which are incorporated herein by reference. Suitable vaporization methods and devices for adaptation and/or use in the present system may also be described in U.S. Pat. Nos. 5,098,431; 5,749,914; 5,454,809; 4,682,596; and 6,582,423, among other references. The full disclosure of each of these references is incorporated herein by reference.

As illustrated in FIG. 10, energizing of selected electrodes 50 may result in vaporization of atherosclerotic material AM, so that the atherosclerotic material is removed from the blood vessel with an aspiration flow F through a lumen of catheter 12. A concurrent irrigation flow helps maintain the environment between the proximal and distal barriers of the catheter, and these two flows allow gases G and ablation debris to be entrained while inhibiting release of such emboli within blood vessel V. The fluid may also act as a cooling fluid to limit heating and collateral damage to other tissues, the circulating fluid often being at least less than body temperature, optionally being at or below room temperature.

Figure 10E:
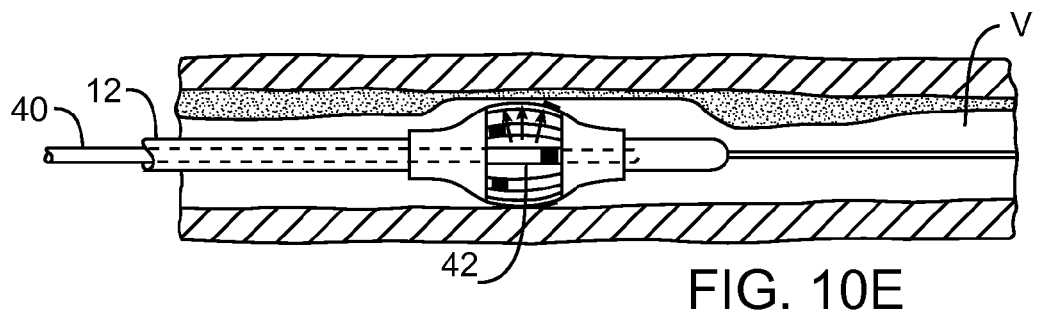

Referring now to FIG. 10E, as described above, it may not be necessary to completely remove all atheroma or atherosclerotic material from within the blood vessel. Providing an open lumen having an effective diameter of at least 80 or 85% of a nominal native lumen diameter may be sufficient. Remodeling treatments may provide acute effective open diameters in a range from about 30% to about 50%. In some embodiments, injury caused to the atherosclerotic material with the energized electrodes or other energy directing surfaces may result in subsequent resorption of the injured tissue lesions so as to provide further opening of the vessel after termination of treatment as part of the healing process.

To promote long term efficacy and inhibit restenosis of a treated region of blood vessel V, a restenosis inhibiting catheter 40 may be advanced through a lumen of catheter 12, so that a radiation source 42 irradiates the treated region of the blood vessel. Suitable intravascular radiation catheters are commercially available from Novoste™, Guidant, Johnson & Johnson, and the like. Restenosis inhibiting drugs similar to those now being employed on drug eluting stents may also be advanced through a lumen of catheter 12, optionally while the proximal and distal barriers again help to maintain a controlled environmental zone within the blood vessel, so that systemic drug delivery might be limited or avoided. In addition to known restenosis inhibiting drugs used on drug eluting stents, drugs which cause vasodilation might be employed. Known restenosis inhibiting drugs such as Rapamycin™ may also be used.

In some embodiments, expandable structure 26 may remain expanded against the vessel wall W and/or atherosclerotic material AM while catheter 12 moves within the blood vessel, the catheter often being drawn proximally during or between ablation treatments. Analogous movement of a radially expanded perforate basket is employed, for example, when measuring temperatures of blood vessels so as to detect vulnerable plaque in systems now being developed and/or commercialized by Volcano Therapeutics. Alternatively, the basket may be repeatedly contracted, axial movement of the catheter 12 employed to reposition the basket, with subsequent expansion of the basket at each of a plurality of treatment locations along atherosclerotic material AM. Repeated intravascular imaging or other atherosclerotic material thickness measurements circumferentially about catheter 12 may be employed, with the remodeling and/or ablation often being halted temporarily so as to allow an image to be acquired intermittently during an ablation procedure. A final image may be taken to verify remodeling and/or ablation has been successful.

Figure 14:
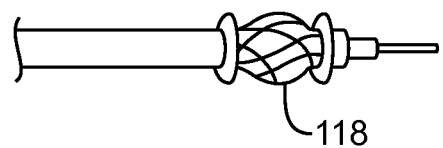

Referring now to FIGS. 11 through 21, a variety of alternative catheter structures are schematically illustrated, with many of these structures providing a microenvironment or controlled environmental zone within the blood vessel which has been enhanced for remodeling and/or ablation. A variety of emboli inhibiting barriers are also described and/or illustrated, including silastic balloons, flexible lips, or expandable cones which may be axially offset from the ablation electrodes. For example, referring to FIGS. 11 and 12, a system similar to that illustrated in FIG. 2 may employ a remodeling and/or ablation sleeve 102 having a proximal hub 104 and receiving an imaging catheter and a guidewire GW in an axial lumen of the sheath. A microenvironment is provided by a microchamber lip 106, which may comprise silicon or the like. Bipolar electrodes 50 may (though need not necessarily) generate gas and/or other ablation debris, which the silicon lip may help to contain. A vacuum port 108 of hub 104 is in fluid communication with a vacuum port 110, while a saline fluid infusion port 112 together with a saline injection passage 114 may be used to control and/or modify the microenvironment for remodeling and/or ablation. As illustrated in FIG. 13, alternate microchambers may be effected using silicon-like lips 116 fully encircling the catheter sheath 102, dual balloons, or the like. As illustrated in FIG. 14, such structures may be combined with a basket 118 supporting RF electrodes so as to provide electrode contact within a microchamber. The basket may optionally comprise a Nitinol™ shaped memory alloy.

Figure 15:
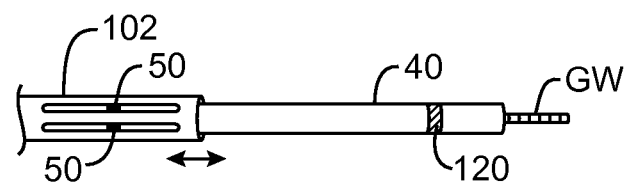

Referring now to FIG. 15, more generally, remodeling/ablation sleeve 102 may support electrode 50 for radiofrequency energy, and may provide one or more lumens for coaxial and/or biaxial insertion of an imaging catheter 34 (such as an IVUS catheter) and/or guidewire GW. Imaging catheter 34 may have a transducer in the form of an array 120.

Figure 16:
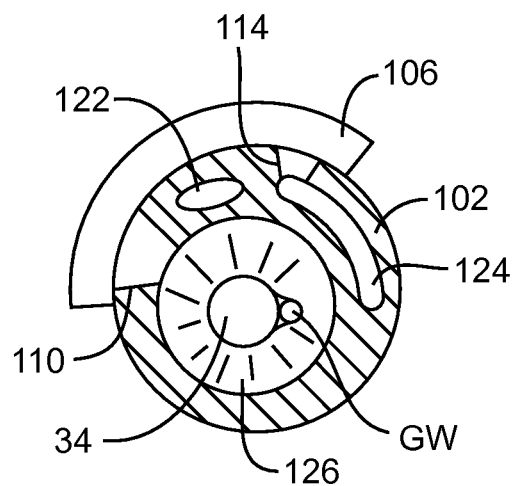

Referring now to FIG. 16, a remodeling/ablation sleeve 102 similar to that shown in FIGS. 11 and 12 has (here in cross section) has an electrode wire lumen 122, a saline injection lumen 124, and the opening of the vacuum port 110 to the working lumen of sheath 102 in which the imaging or IVUS catheter 34 and guidewire GW are disposed. A silicon lip or valve 126 allows a vacuum to be transferred to the microenvironment.

Figure 17:
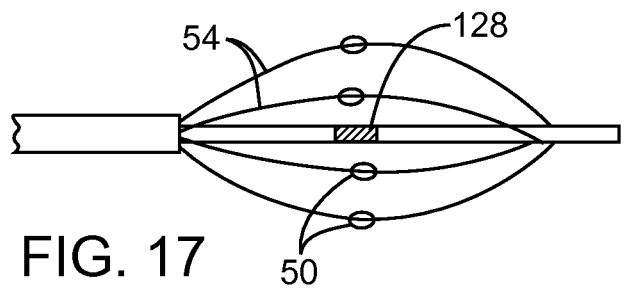
Figure 17A:
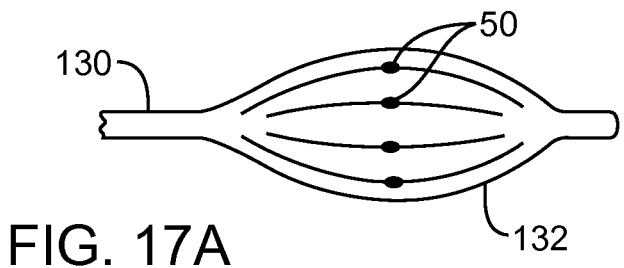

Still further alternative arrangements are illustrated in FIGS. 17 and 17A. In the embodiment of FIG. 17, an inner electrode 128 is used in a bipolar system along with outer electrodes 50, which contact the tissue for treatment. FIG. 17A schematically illustrates use of a balloon catheter 130 having a balloon 132 (such as a latex balloon). On the surface of the latex balloon electrodes 50 are mounted for use in selected pairs. Hence, a balloon (rather than a basket structure) may be used as a radially expandable structure for carrying the electrodes or other energy delivery surfaces.

Figure 18:
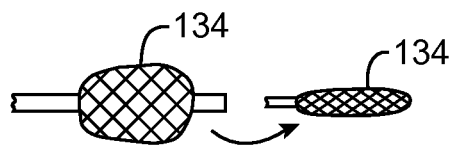
Figure 19:
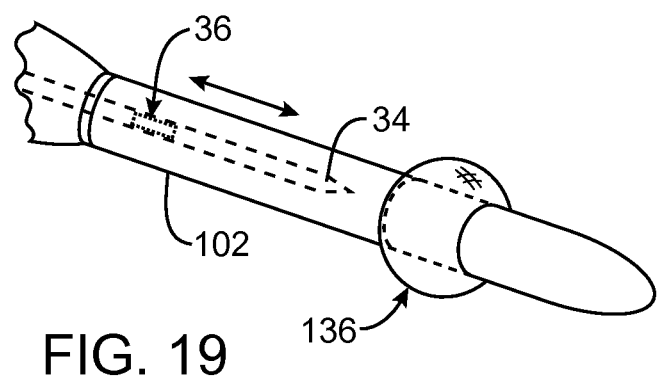
Figure 20:
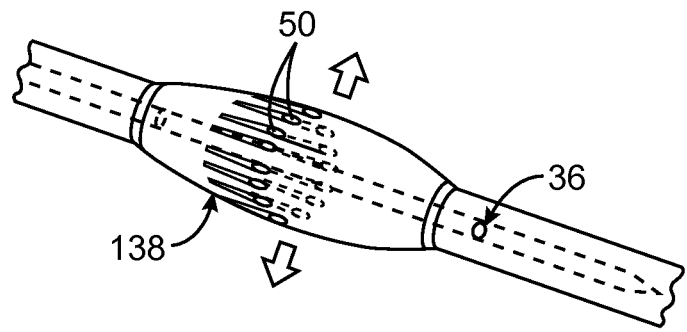
Figure 21:
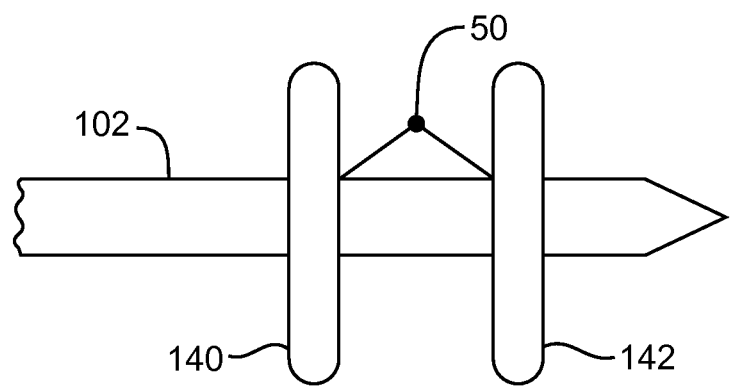

FIG. 18 schematically illustrates an expandable basket 134 being contracted from a large configuration to a small configuration. The basket may optionally be used as a cutting basket by providing appropriate edges, and/or may capture emboli within. FIG. 19 illustrates a remodeling/ablation sleeve 102 in which imaging catheter 34 travels axially back and forth to image, and in which a silastic balloon 135 is disposed distal of the treatment debris for emboli capture. FIG. 20 illustrates an alternate electrode delivery balloon 138 similar to balloon 132 of FIG. 17A, and illustrates electrodes 50 having flexible lumen extensions extending proximally therefrom. FIG. 21 schematically illustrates an RF electrode within a microchamber provided by proximal and distal barriers 140, 142 of sheath 102, in which a position of electrode 50 is actuated in the microchamber.

Figure 22:
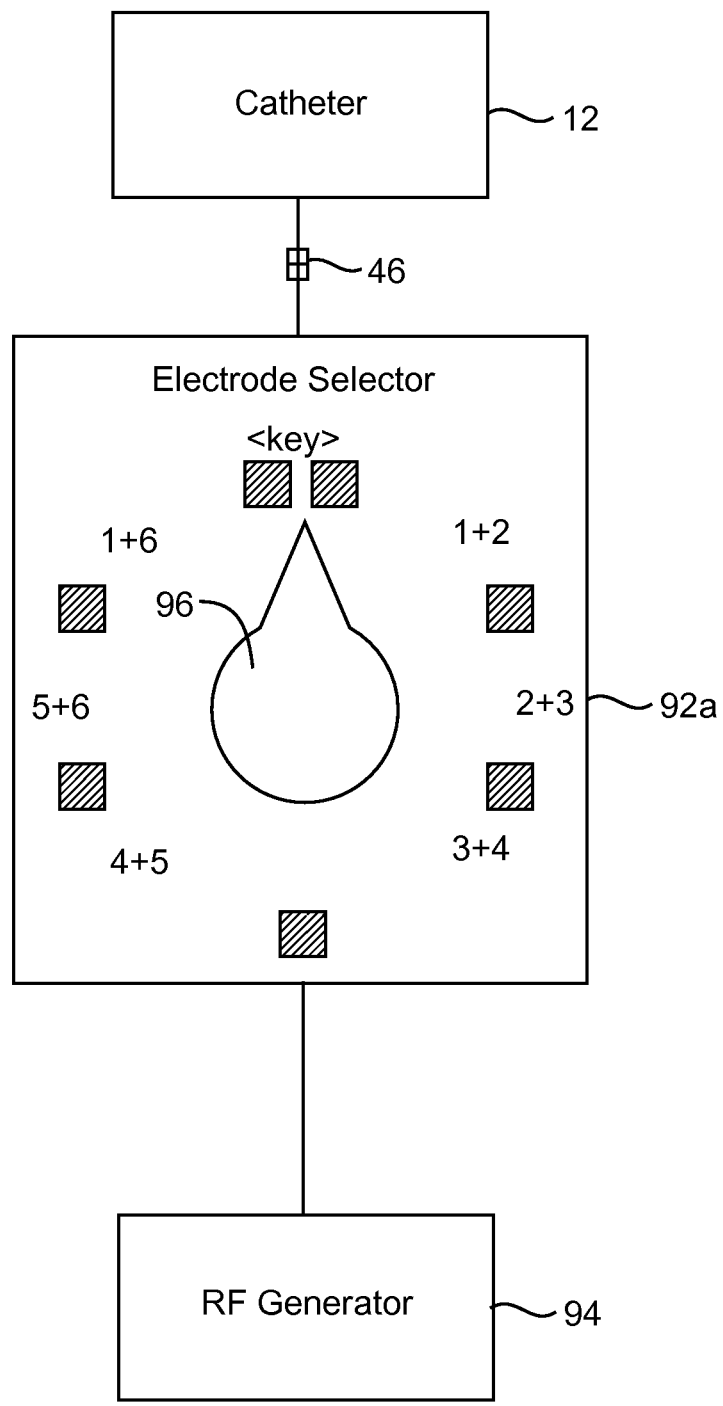
FIGS. 22-25 schematically illustrate controllers for selectively energizing electrodes in the system of FIG. 2.
Figure 23:
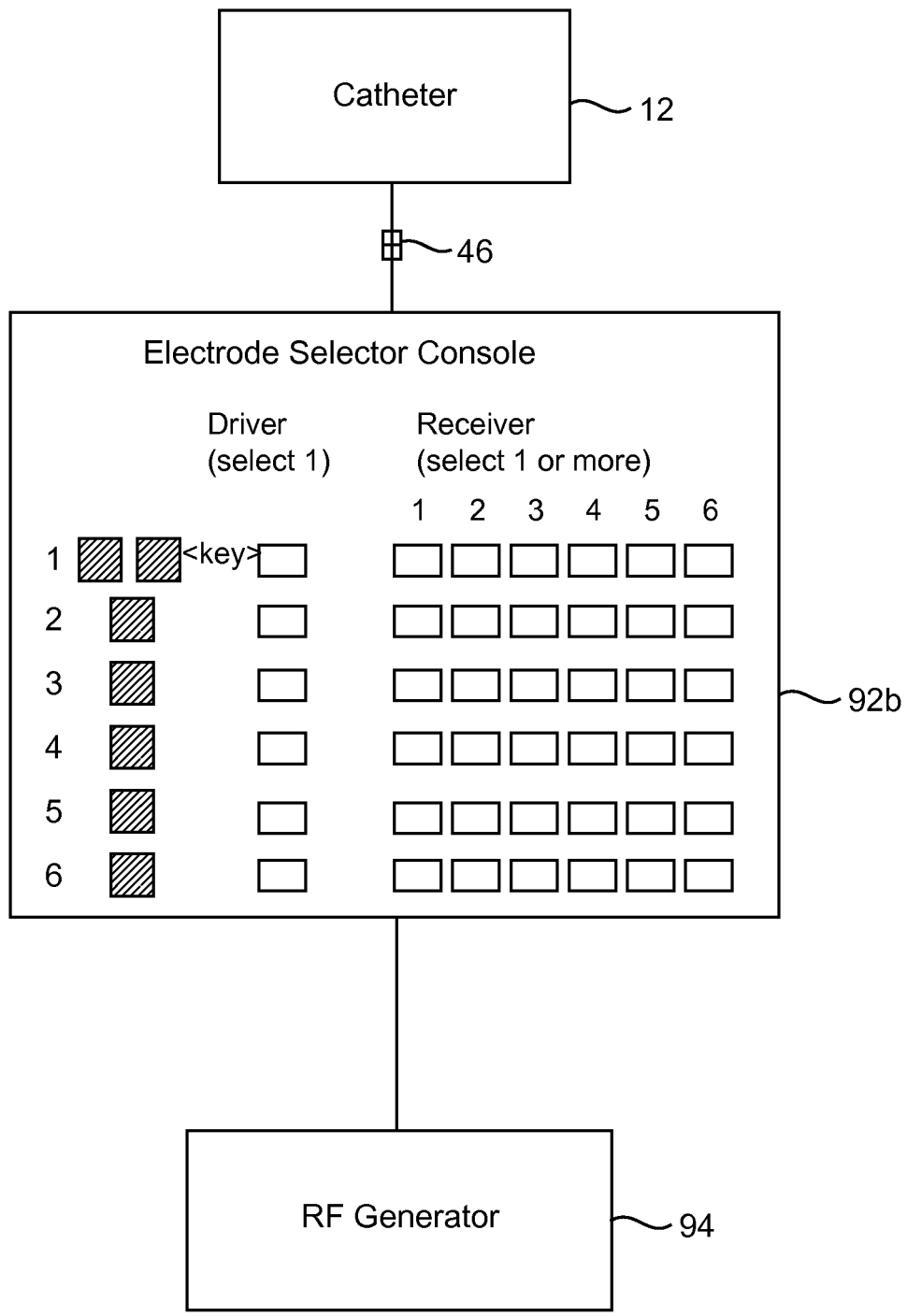
Figure 24:
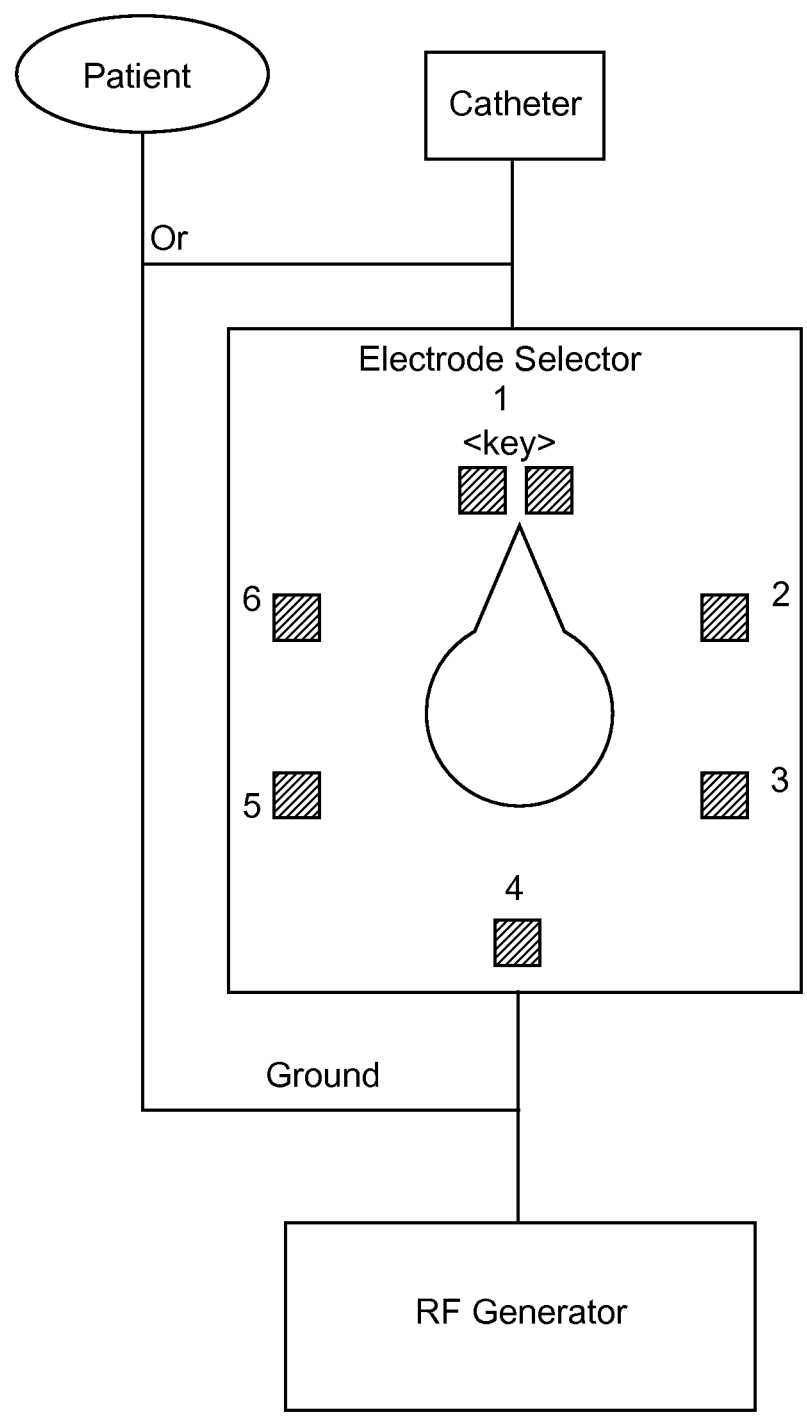
Figure 25:
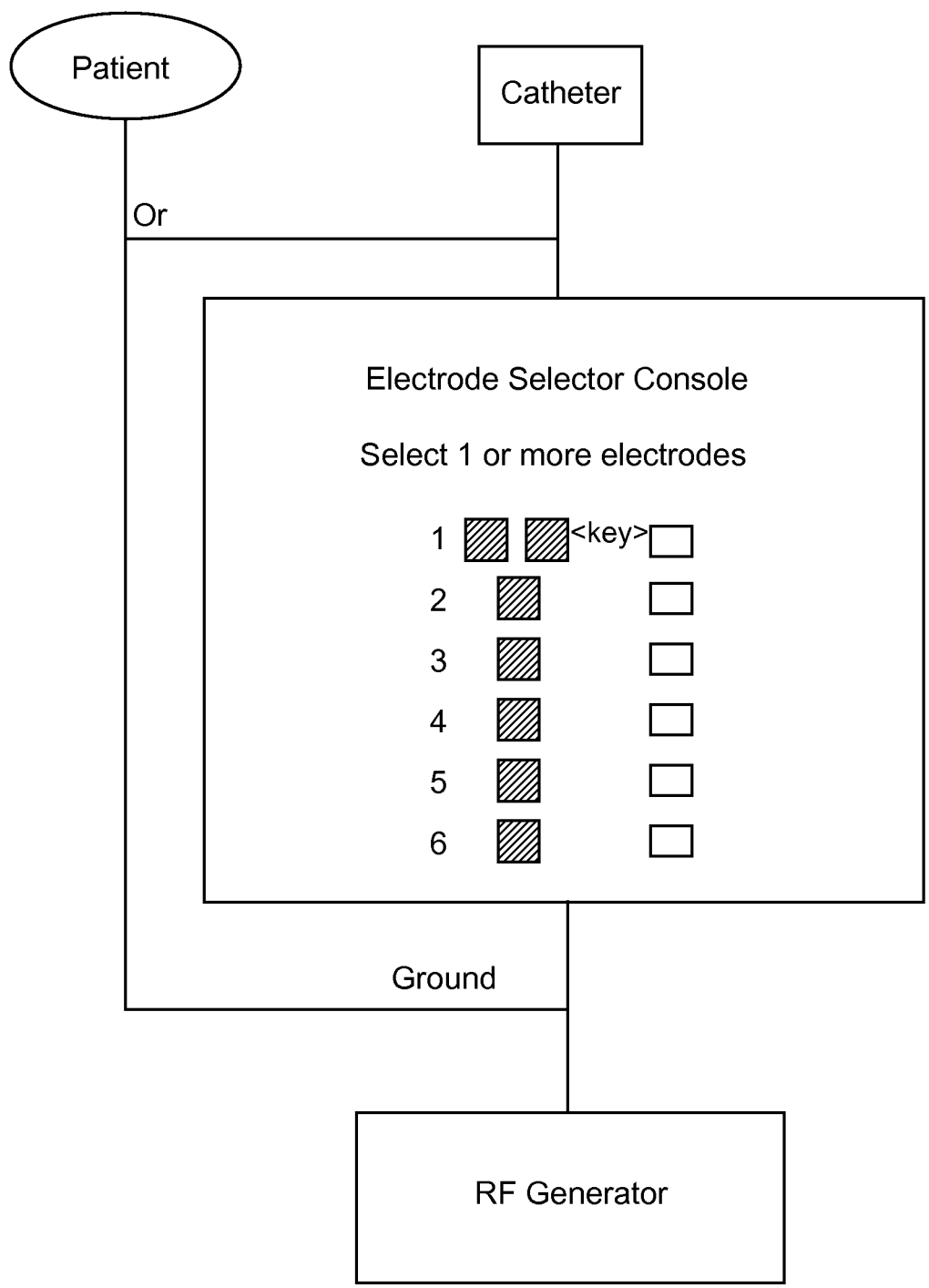

Referring now to FIGS. 22 and 23, alternative controllers 92a, 92b selectively energize electrodes of catheter 12 with RF power supplied from an RF generator 94. A wide range of RF energy types may be employed, including burst of 500 Khz, different types of waveforms, and the like. In controller 92a, a simple dial 96 is turned to point to a desired electrode pair to be energized. A "key" electrode may be registered with the intravascular imaging system, either electronically or by providing an electrode, electrode support member, or attached marker which presents a distinct image on the intravascular imaging display. This simplifies selection of one or more eccentric electrode pair along atheroma. Advantageously, catheter 12 need not be rotated into a proper orientation to accurately remodel and/or ablate the desired eccentric atherosclerotic material. Controller 92b includes similar capabilities, but allows the operator to select multiple electrodes for driving bipolar RF energy therebetween, providing greater flexibility in allowing multiple electrodes to be simultaneously energized. FIGS. 23 and 24 illustrate monopoly control arrangements similar to those of FIGS. 21 and 22, respectively. Patient grounding may be effected by a patient grounding plate, a ring electrode 2 to 5 cm proximal to basket 26, or the like. Once again, no catheter rotation is required to orient an active side of the catheter adjacent to the targeted atheroma since various eccentric ablation orientations can be selected through the electrode selection controller.

Figure 26:
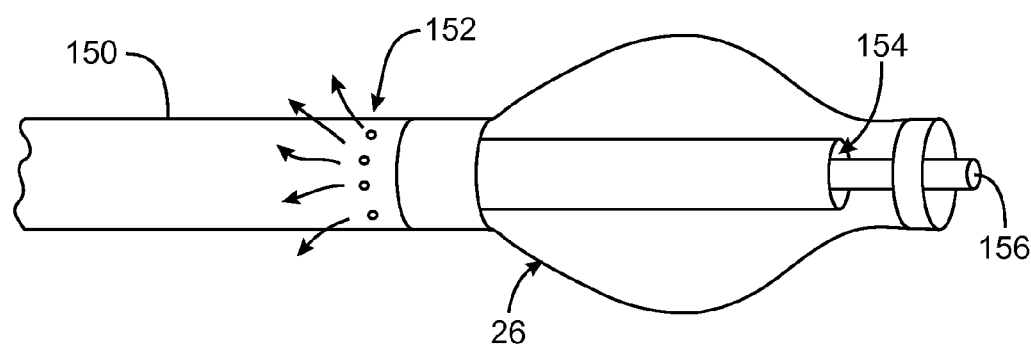
FIGS. 26 and 27 schematically illustrate alternative fluid flow paths for use in an atherosclerotic material remodeling catheter.
Figure 27:
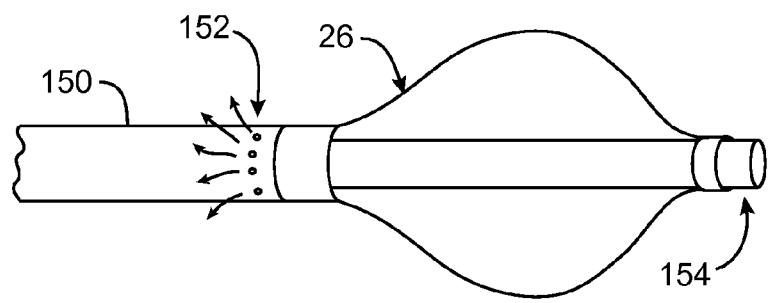

FIGS. 26 and 27 schematically illustrate alternative fluid flow arrangements for use in the catheters and methods described herein. In the embodiment of FIG. 26, a tubular body 150 extending proximally from expandable body 26 includes one or more irrigation ports 152, the irrigation ports here being disposed proximally of the expandable body. An aspiration port 154 contains a tubular body defining a guidewire and/or imaging catheter lumen 156. Irrigation fluid may flow distally, which may also be the direction of blood flow in the body lumen. Irrigation fluid may be aspirated through the aspiration port. In the embodiment of FIG. 27, lumen 154 is used for aspiration and for a guidewire and/or imaging catheter.

An alternative controller is illustrated in FIGS. 28A-D. This controller allows an operator to choose, for each electrode, whether to keep that electrode inactive, electrically couple that electrode to a first pole (sometimes referred to as pole A) of an energy source (such as an RF generator or the like), or to electrically couple that electrode to a second pole or pole B of the energy source. This controller allows a wide range of energized electrode configurations, including pseudo-monopolar modes where all electrodes except one are connected to one pole of the energy source (pole A) and one electrode is connected to the other pole (pole B). As can be understood with reference to FIG. 28A, controller 160 allows testing of many electrode configurations for RF remodeling and/or ablation, particularly those involving two or more electrodes. A switch panel 162 is shown in more detail in FIG. 28B. Each electrode (in this embodiment, up to eight electrodes) is electrically coupled to a 3-way switch numbered from 1 to 8, a switch disposed in the middle position indicates the electrode is not coupled to either pole, while a switch pushed toward the plus sign indicates the associated electrode is coupled to a red RF connector with the controller. Similarly, a switch pushed toward the minus sign indicates the associated electrode is electrically coupled to a black RF connector of the control box.

Figure 28A:
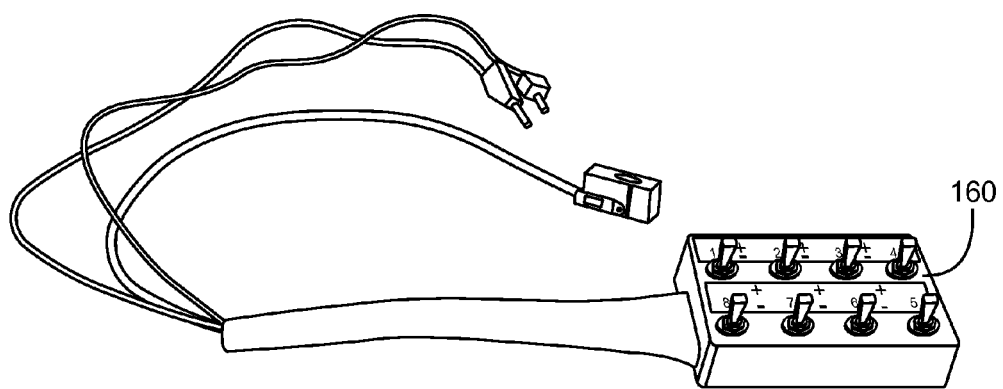
FIGS. 28A-28D illustrate an alternative controller for selectively energizing electrodes in the system of FIG. 2.
Figure 28B:
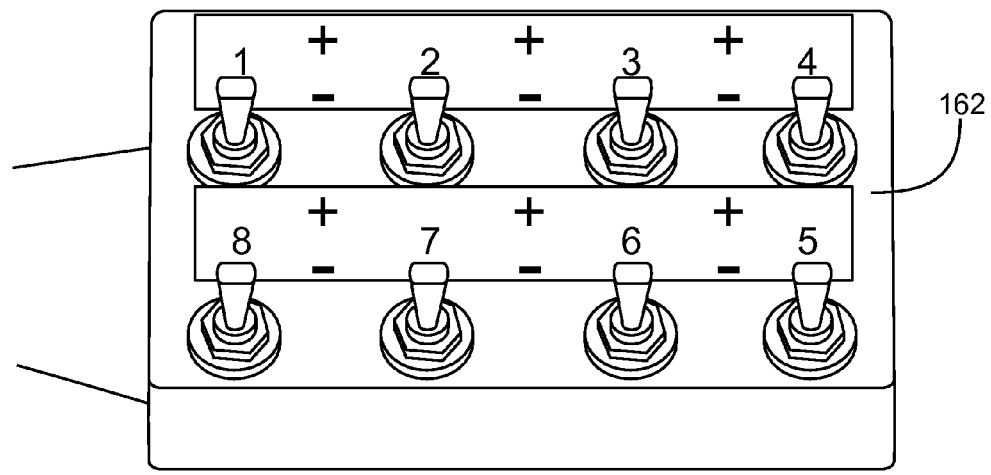
Figure 28C:
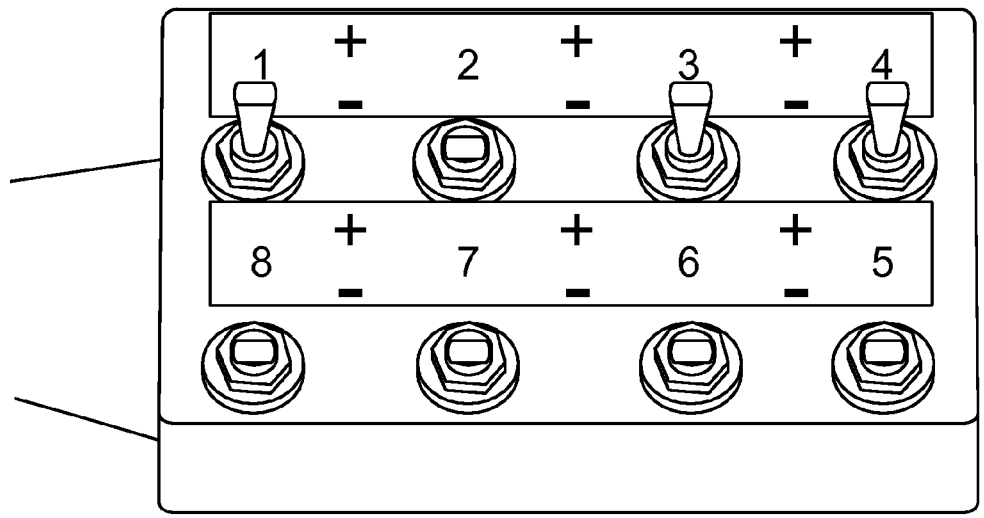
Figure 28D:
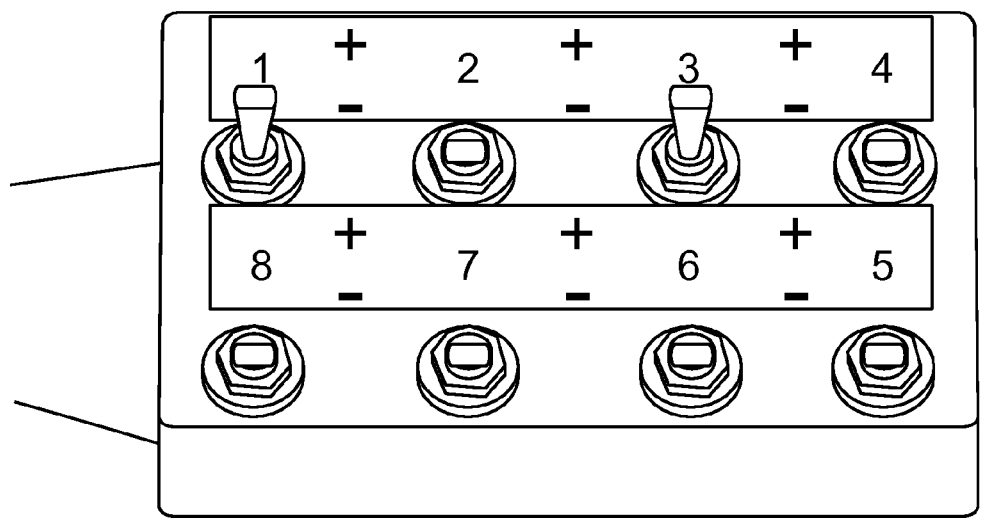

As can be understood with reference to 28C, electrodes associates with switches 3-8 are not coupled to either pole, electrode 1 is connected to the red RF connector, and electrode 2 is connected to the black RF connector. Activation of the RF generator will circulate bipolar RF energy between electrodes 1 and 2. In FIG. 28D, electrodes 5-8 are not energized, while electrodes 1 and 3 are coupled to the red RF connector. Electrodes 2 and 4 are connected to the black RF connector, so that activation of the RF generator will circulate bipolar RF energy between electrodes 1 and 3 and between electrodes 2 and 4.

Figure 29A:
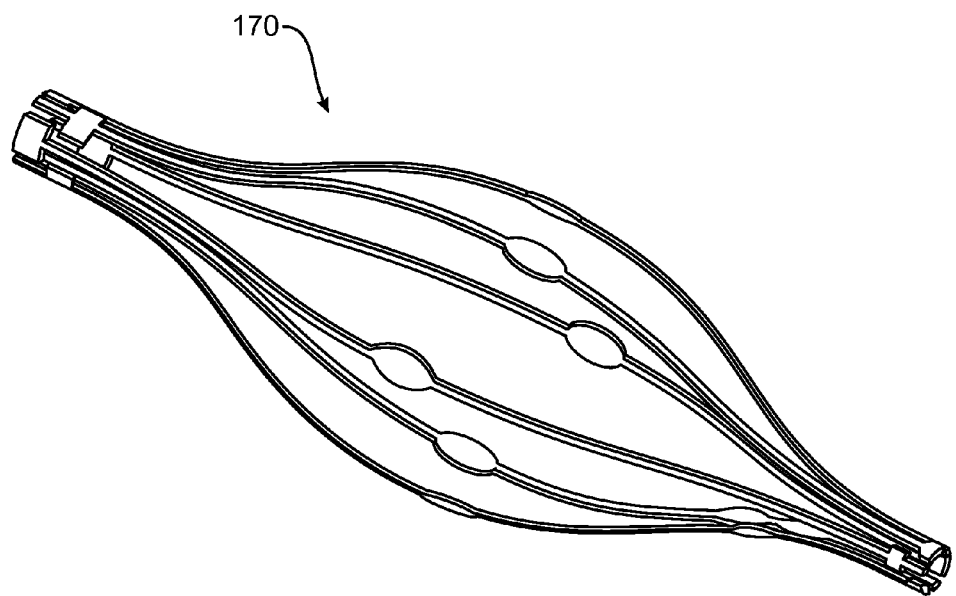
FIGS. 29A-29H illustrate an alternative basket structure formed with independent struts having a localized enhanced width for use as an electrode surface, along with components thereof.
Figure 29B:
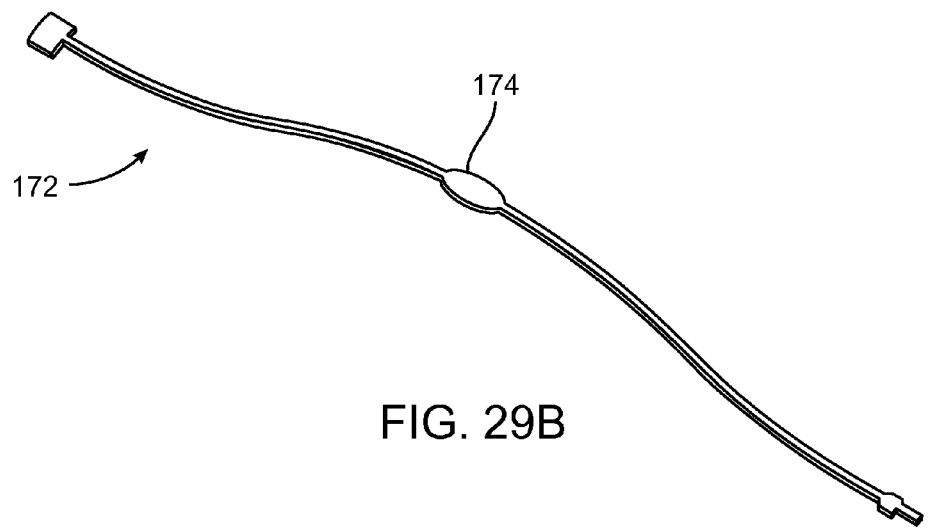
Figure 29C:
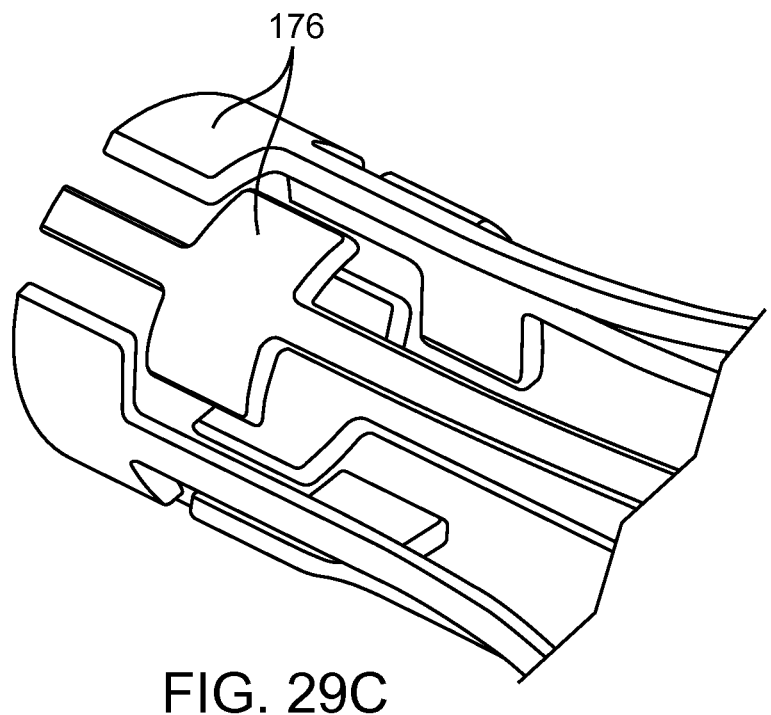
Figure 29D:
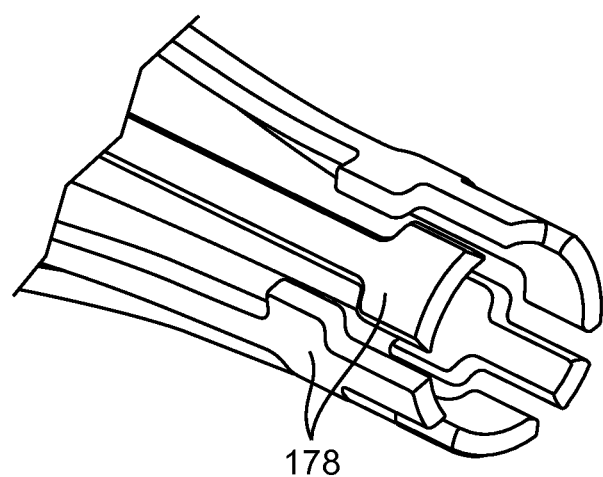
Figure 29E:
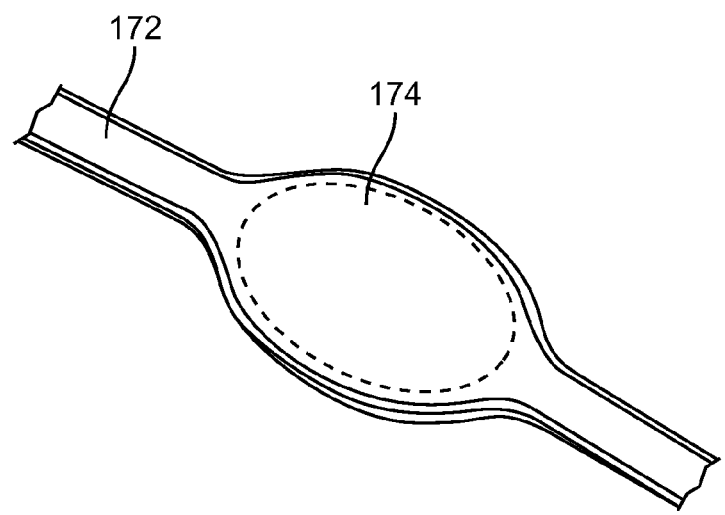

An exemplary self-expandable basket is illustrated in FIGS. 29A-29H. As can be understood from these drawings, electrodes may be fabricated as part of the struts 172 from which the basket is formed, for example, using a radially outwardly oriented surface of a localized widening 174 of each strut disposed in axially central portion of the strut, as can be seen in FIGS. 29B and 29E. Each arm may be formed from one piece of material, optionally comprising a Nitinol™ nickel-titanium shaped memory alloy, with the struts optionally being laser cut from a Nitinol™ tube. The electrode/basket may be, for example, coated with a high temperature polymer such as a polyimide. Electrodes 174 may be formed by inhibiting coating or removing coating from the desired portion of the associated strut 172 (as illustrated in FIG. 29E) so that the electrode surface is exposed for contact with atherosclerotic material. The struts may be separated from each other and structurally supported with an insulated material such as ultraviolet ("UV") cure or heat shrink sleeve, a polyethylene, Nylon™, or the like to form basket 170.

Figure 29F:
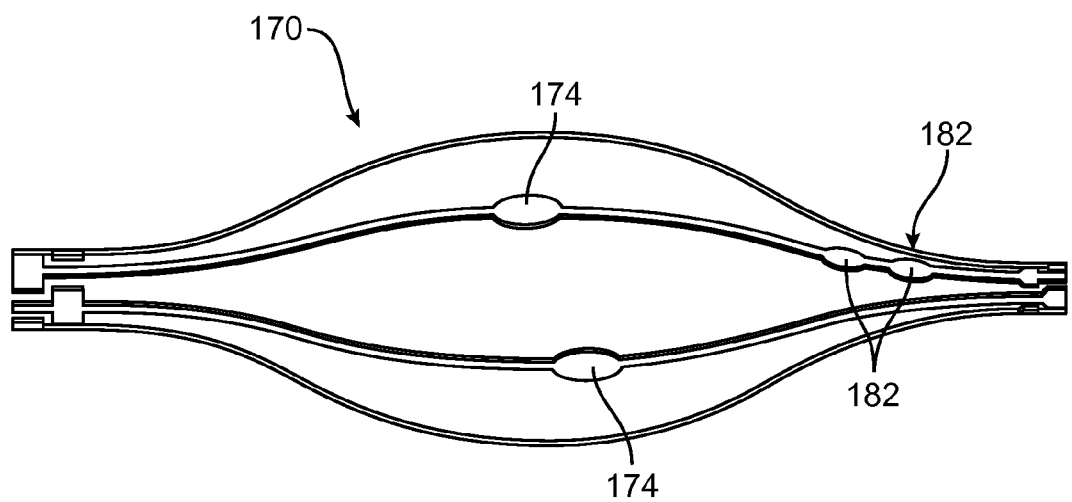

Each strut 172 may be used to conduct energy between electrode surface 174 and an electrical conductor extending proximally from the strut toward a controller. Proximal pads for connecting such conductors are illustrated in FIG. 29C, while distal structural pads 178 are illustrated in FIG. 29D. Adjacent electrodes 174 may be axially offset or staggered as can be seen in FIG. 29F. Insulating coating along each strut 172 may be inhibited or removed from an inner surface of proximal pads 176 so as to facilitate connecting of an associated conductive wire, such as by spot welding or the like. Alternative insulating materials may also be used, including parylene coatings, while alternative methods for attaching struts 172 to a catheter body may be employed, including adhesive bonding using insulating UV cure, embedding the pad structures in polyethylene, and the like.

Figure 29G:
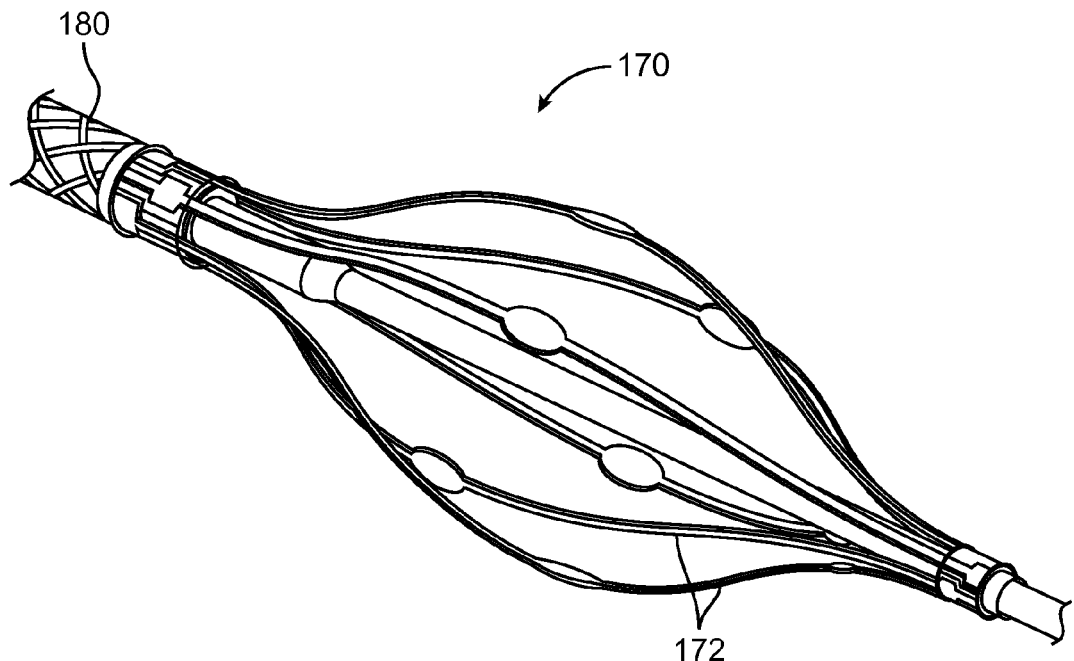

Exemplary structures for fixing struts 172 of basket 170 to a catheter body 180 are illustrated in FIG. 29G.

Figure 29H:
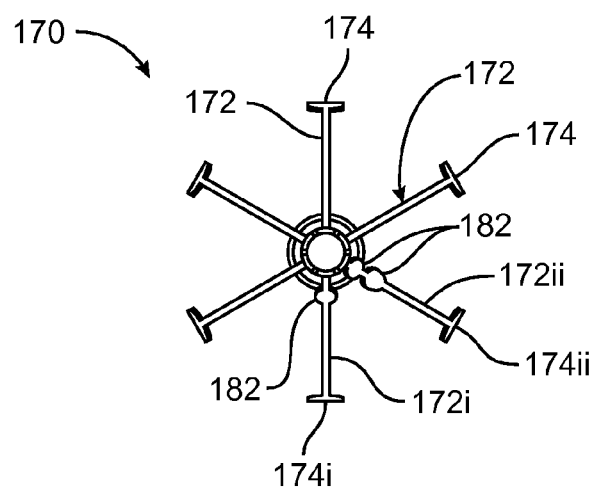

Referring now to FIGS. 29F and 29H, an alternative indicia providing a distinguishable image for rotationally registering selected electrodes 174 of basket 170 to images or other atherosclerotic material measurements can be understood. In this embodiment, an electrode 174i referenced as electrode 1 may have a radiopaque marker 182 disposed on the associated strut 172i. A strut 172ii supporting an associated second electrode 174ii may have two radiopaque markers 182 provide a circumferentially asymmetric count indicator allowing all electrodes to be referenced without ambiguity. The shape of electrodes 50 may vary, for example, electrodes 174 may be wider than other portions of struts 172 as illustrated in FIGS. 29A-G.

As described above, remodeling will often be performed using irrigation and/or aspiration flows. In many embodiments, an irrigation port directs fluid, such as a saline solution, from an irrigation lumen to an interior of the basket. An aspiration port may provide fluid communication between an aspiration lumen and an interior of the basket. One or both of these fluid flows may be driven continuously, or may alternatively pulsate before, during, and/or after treatment. In some embodiments, aspiration and/or irrigation flow may occur acutely or concurrently so as to circulate between the irrigation port and the aspiration port. Optionally, the flow may carry ablation debris to the aspiration port, where the debris may be evacuated through the aspiration lumen. There may be coordination between the irrigation system and the aspiration system such that the irrigation fluid may remain confined in an area closely adjacent the basket so as to inhibit embolization of ablation debris when the basket is expanded within the blood vessel. Such coordination, for example, may inhibit distal movement of ablation debris, and/or may obviate any need for a distal and/or proximal barrier or membrane. In some embodiments, the circulation of fluid between an irrigation port and an aspiration port may create an effectively bloodless environment adjacent the electrodes to facilitate remodeling and/or ablation, imaging of atherosclerotic tissue, and the like.

Figure 30A:
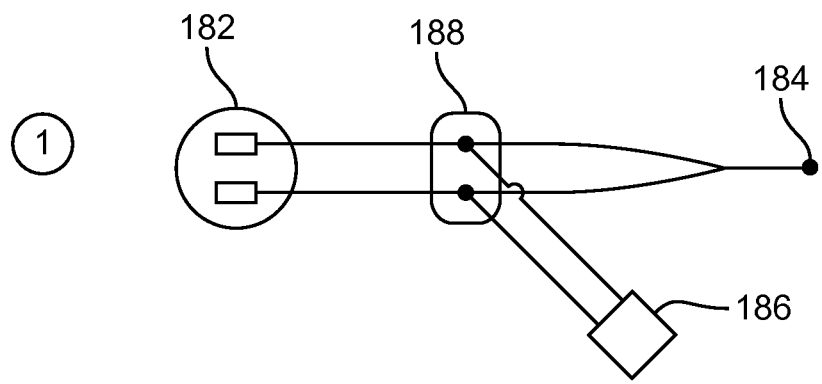
FIGS. 30A and 30B schematically illustrate electrical circuitry allowing thermocouples and other temperature sensors to be used both for measuring temperature and as electrodes.
Figure 30B:
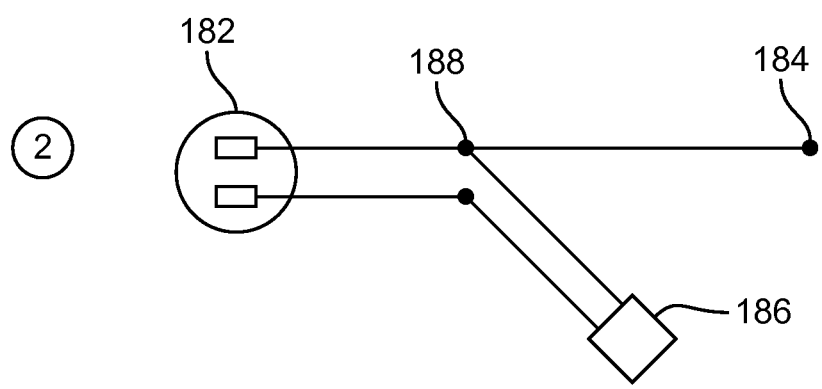

Referring now to FIGS. 30A and 30B, control of energy directed from the catheter systems and structures of the present invention may optionally make use of thermocouples and other temperature sensing structures. Thermocouples such as K-type thermocouples (+CH/−AL) may be attached to or near one or more struts of an expandable structure to provide temperature measurements. For example, such structures may provide tissue temperature measurements, blood temperature measurements, treatment temperature measurements, and/or the like.

Optionally, a temperature measurement structure may also be used as an RF electrode, for example, by employing one or more of the structures illustrated in FIGS. 30A and 30B. In the embodiment of FIG. 30A, a thermocouple 182 can be coupled to either an RF energy source 184 or a thermometer 186 by a switch 188. A similar embodiment is illustrated in FIG. 30B.

Figure 31:
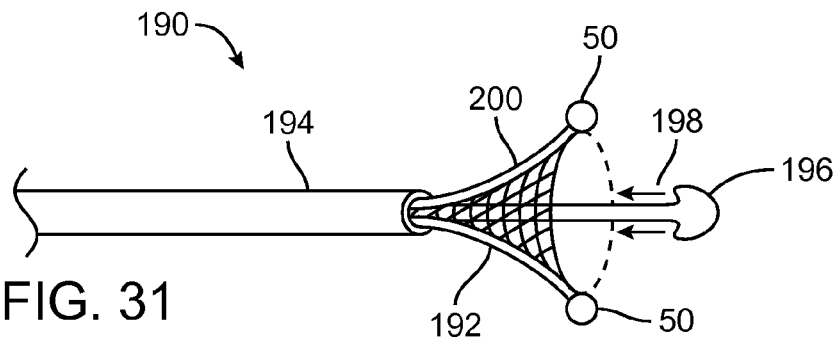
FIG. 31 schematically illustrates an alternative catheter structure for use in the methods described herein.

Referring now to FIG. 31, an alternative catheter system 190 includes a plurality of electrodes 50 supported by struts 192. Struts 192 expand radially when extended distally through a sheath 194 so that a circumferential array of the electrodes is collapsible. A ball-shaped tip 196 includes proximally oriented high pressure jets 198, and the ball-shaped tip may be used as one pole with selected electrodes 50 being used as the other pole. Alternatively, bipolar power may be driven between electrodes 50 or the like. Optionally, a proximal barrier 200 such as a screen may be used to inhibit movement and/or capture any debris.

When the RF electrodes are energized, the high pressure jets may also be activated so as to provide a saline flush. A venturi effect may entrain the debris for transport proximally through a catheter lumen for evacuation, typically using an aspiration source coupled to sheath 194. Debris may be trapped in barrier 200 which may comprise a screen, a solid sheet, a net, or the like. In some embodiments, low pressure jets may be used from adjacent ball tip 196 in place of high pressure jets.

Figure 32A:
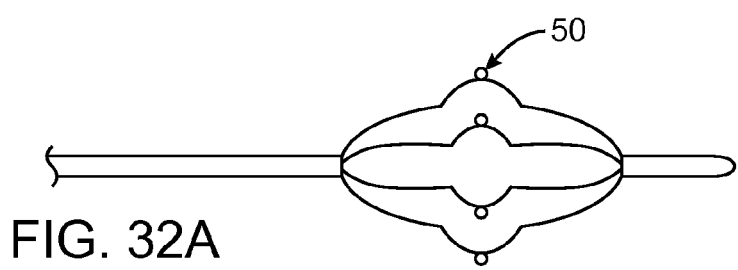
FIGS. 32A-32D schematically illustrate alternative basket and catheter structures for use in the methods described herein.
Figure 32B:
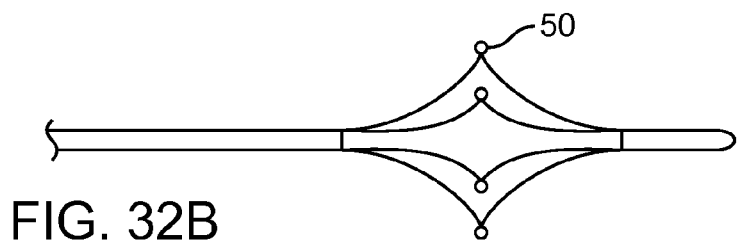
Figure 32C:
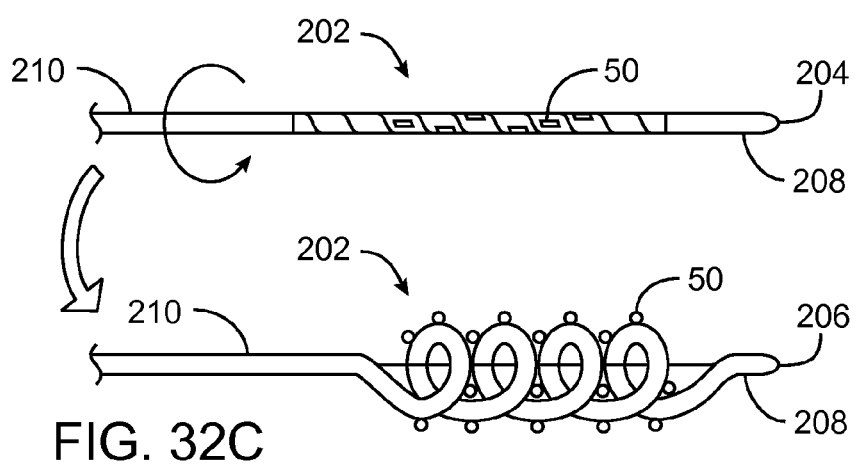
Figure 32D:
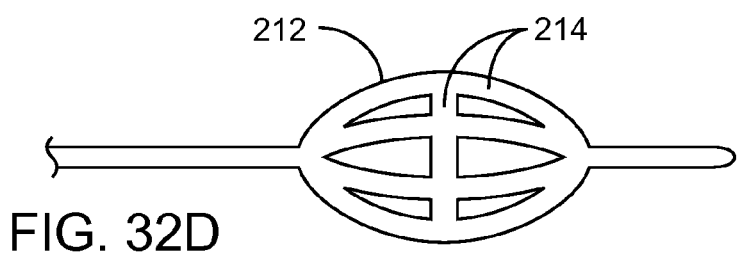

Referring now to FIGS. 32A-32D, alternative expandable structures may avoid kinking or flattening of the expandable structure when the expandable structure bends axially, such as when it is expanded along a bend in a body lumen. In the embodiment of FIG. 32C, a coil or helical expandable structure 202 has a small profile configuration 204 and a large profile configuration 206, and may be deployed and/or retracted by twisting a distal end 208 and/or a proximal tubular body 210 relative to each other, by a pull/release mechanism, or the like. Aspiration and/or irrigation may be provided through the proximal tubular member 210 as described above, and the coil structure may include a single loop or a plurality of loops so as to provide one or more circumferential rows of electrodes 50 when in the expanded configuration 206. In the embodiment of FIG. 32D, an inflatable expandable structure 212 includes axial struts and/or rings formed as tubular inflatable balloons so as to allow the expandable structure to expand from the small profile configuration to the shown large-profile configuration.

Figure 33:
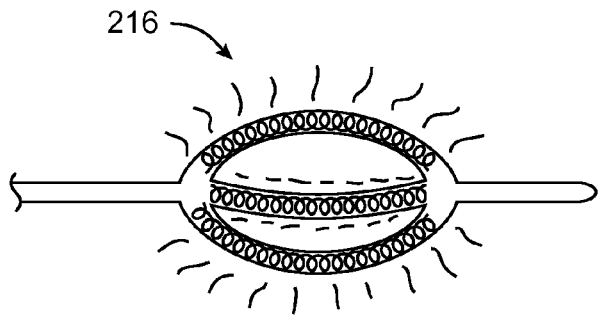
FIG. 33 schematically illustrates an alternative catheter structure using microwave energy to remodel atherosclerotic material.
Figure 34:
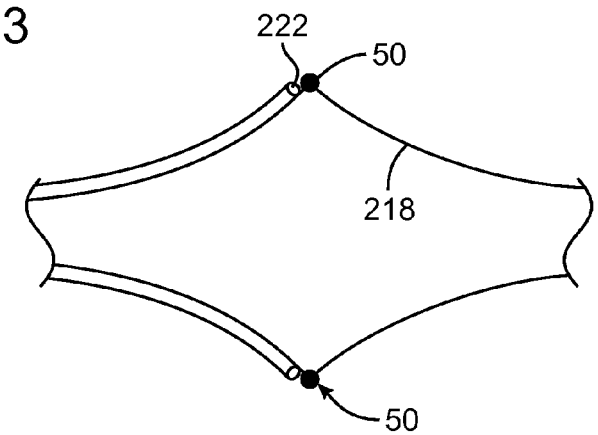
FIG. 34 schematically illustrates an alternative catheter structure having lumens extending toward the electrodes so as to provide directed irrigation flow in the methods described herein.
Figure 35:
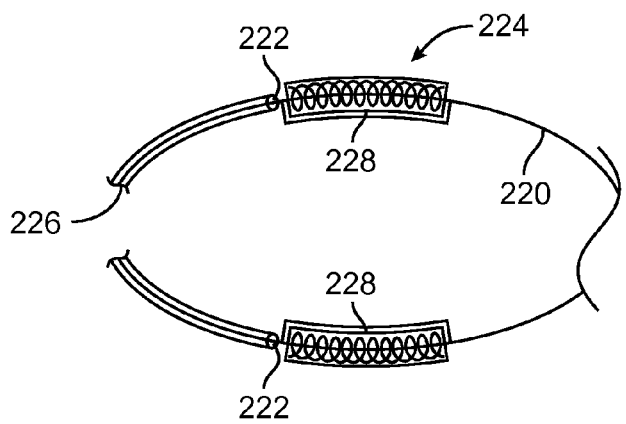
FIG. 35 schematically illustrates a further alternative catheter basket structure having lumens for directing irrigation flow toward the microwave antennas for use in the methods described herein.

Still further alternative expandable structures and energy delivery surfaces are schematically illustrate in FIGS. 33-35. In a microwave treatment device 216 illustrated in FIG. 33, each strut of a basket may include a helicoidal microwave antenna, with an inner side of the antenna shielded to avoid emitting energy toward the catheter axis. Alternative microwave antennas may also be employed, including unidirectional antennas which allow depth between an energy delivery surface and a target tissue to be varied by varying a focus of the antenna. Such focused microwave devices may include antennas that are rotatable about the catheter axis, axially moveable, and the like.

In the embodiments of FIGS. 34 and 35, catheter bodies again support a series of struts 218, 220 and also have a plurality of irrigation or flush lumens. The irrigation lumens within the catheter body are in fluid communication with tubular structures extending along the (and in some cases being integrated into the) struts, so that fluid flush ports 222 direct saline or other fluids towards electrodes 50 or microwave antennas 224. Electrosurgical power for the energy delivery surfaces may be transmitted using the strut structure, or wires 226 may extend along the strut to the energy delivery surfaces. In the embodiment of FIG. 35, shield 228 along an inner portion of a microwave antenna 224 can be seen, which may limit microwave energy directed toward an imaging catheter. For embodiments employing microwave antennas as energy delivery devices, only one antenna of the circumferential array may be energized at a time, so as to avoid interference between conductors along the catheter body.

Figure 36:
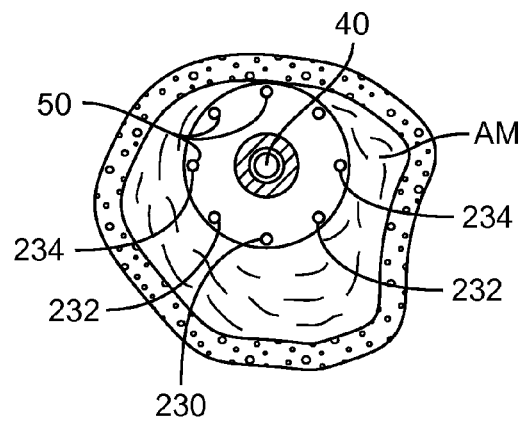
FIG. 36 is a schematic cross sectional view showing the application of different power levels through different electrodes so as to eccentrically remodel atherosclerotic materials.

Referring now to FIG. 36, controllers of the catheter systems described herein may allow distribution of differing power levels to differing pairs of electrodes. For example, in response to a circumferential distribution of atherosclerotic material AM such as that illustrated in FIG. 36, a controller may direct 50 watts of energy to a first electrode 230, 30 watts of energy to a pair of second electrodes 232 and only 10 watts of energy to a pair of third electrodes 234. Other electrodes may have no energy directed thereto, as described above. In some embodiments, a differing power directed to the differing electrodes may be provided by controlling the duty cycle, for example, with 50 watts being provided by energizing one or more electrode for 50% of the time, 30 watts being provided by energizing an electrode 30% of the time, and the like.

Figure 37A:
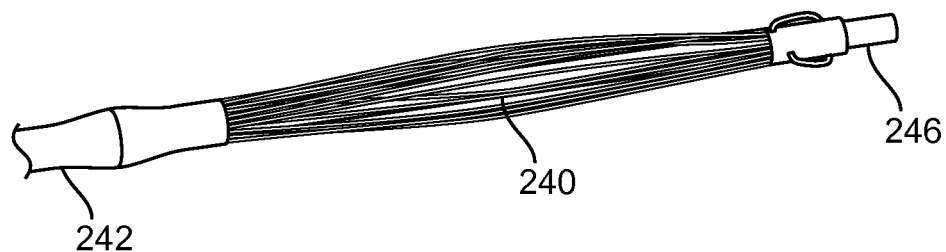
FIGS. 37A-37C illustrate a further alternative catheter basket structure, in which the basket comprises polyimide for supporting a circumferential array of electrodes and facilitating intravascular imaging.
Figure 37B:
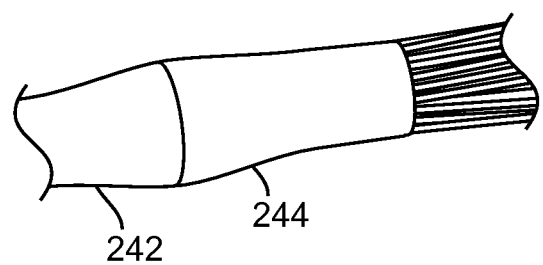
Figure 37C:
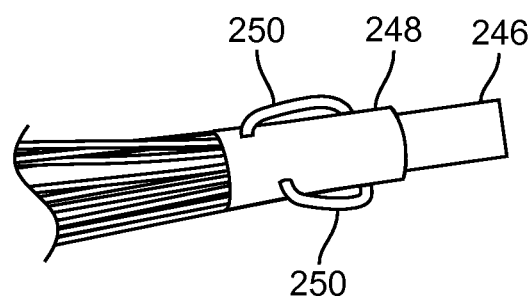

Referring now to FIGS. 37A-37C, many imaging modalities (including intravascular ultrasound, optical coherence tomography, intravascular MRI, and the like) may be at least in part blocked or degraded by positioning the image detecting structure within a metallic structure such as a basket formed of Nitinol™. Hence, there may be advantages in producing alternative expandable structures such as baskets comprising plastics or a polymer. In light of the heat generated by the electrodes of the systems described herein, it may be advantageous for such polymer basket structures 240 to comprise a high temperature polymer such as a polyimide.

Alternative basket structures may comprise HDPE, PET, Nylon™, PEBAX™, and the like. As illustrated in FIG. 37B, proximal ends of the basket struts may be glued to a shaft 242 at a bond 244. An imaging catheter guide 246 may extend through a distal end of the basket structure 248, with the distal end of the basket free to slide axially along the guide. Pullwires 250 may be affixed to the distal end 248, so that pulling of the pullwires radially expands basket 240, with the pullwires running inside the proximal shaft 242. The basket may be retracted back to its small profile configuration by pushing of the pullwires, or the basket may include biasing means urging the basket to the small profile configuration. So as to avoid degradation to imaging performance, polymer tension members similar to fishing line may be used as pullwires. In the exemplary embodiment, the pole wires comprise Nitinol™ which has sufficient compressional rigidity to push the basket to its small profile configuration.

Basket 240 may be formed by cutting struts from a tube of the polymer material, with the distal portion 248 preferably remaining uncut. The proximal ends of the struts may be separated prior to forming bond 244, and ring-shaped RF electrodes may be slid along each arm and glued to the desired configuration along the intermediate portion of the basket.

Figure 38A:
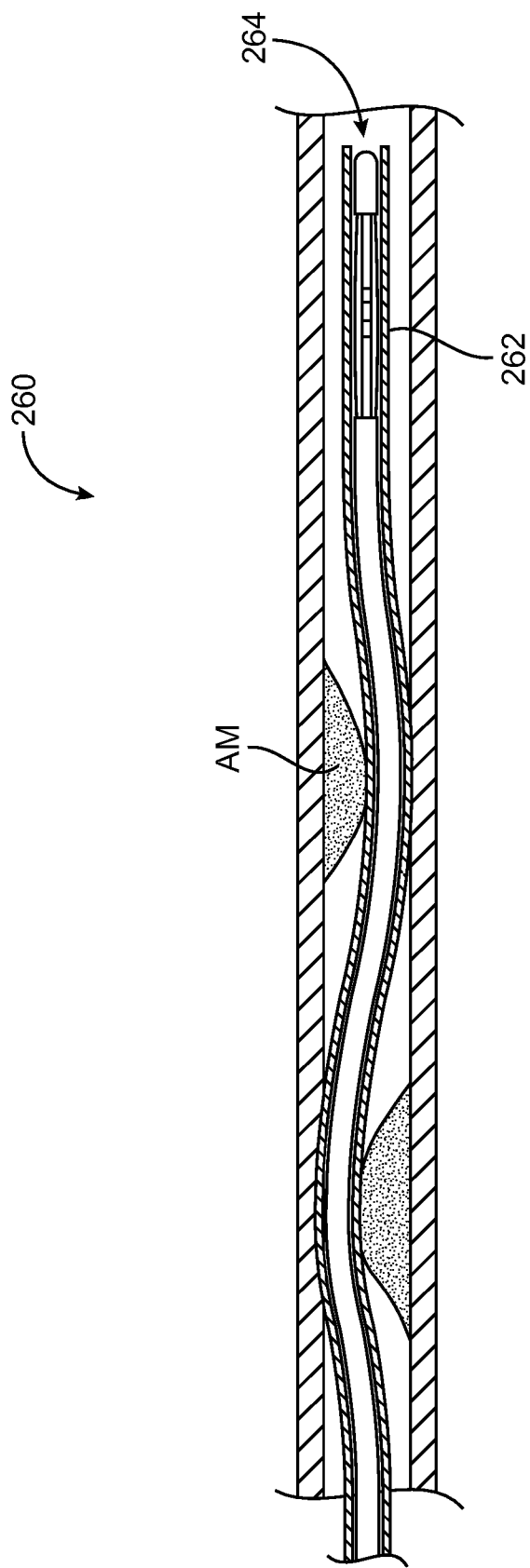
FIGS. 38A-38E are cross sectional side views through a body lumen showing additional aspects of treatment methods and devices described herein.
Figure 38B:
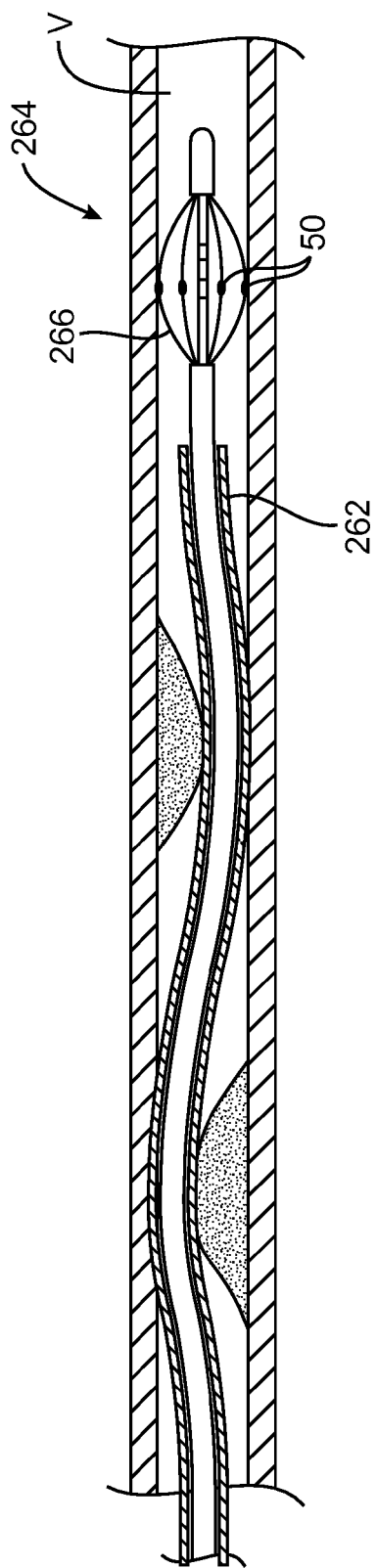

Exemplary treatment methods are illustrated in FIGS. 38A-38H. In FIG. 38A, the catheter system 260 includes a basket covering sheath 262 over an atherosclerotic material detecting and treating catheter 264 as described above. In this embodiment, outer basket sheath 262 radially restrains the basket 266, which is biased to expand radially when released from the outer sheath, as illustrated in FIG. 38B. In some embodiments, the basket may be expanded after the outer sleeve is retracted, such as by pulling pullwires, rotating one portion of the catheter relative to the other, or the like. Regardless, as the basket expands within the vessel V, electrodes 50 of the basket engage the surrounding vessel wall. An imaging transducer near basket 266 of an imaging catheter disposed in a lumen of the treatment catheter evaluates the vessel V, and the detection/treatment catheter system 264 is pulled proximally along the artery or vessel V.

Figure 38C:
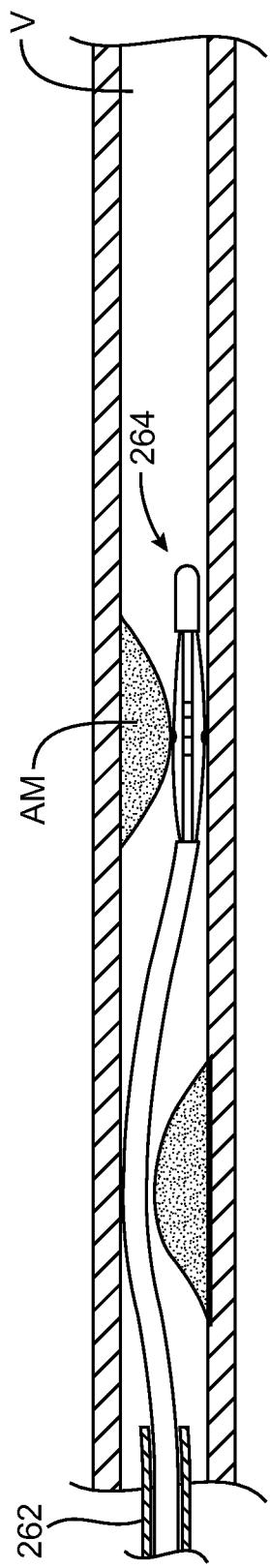
Figure 38D:
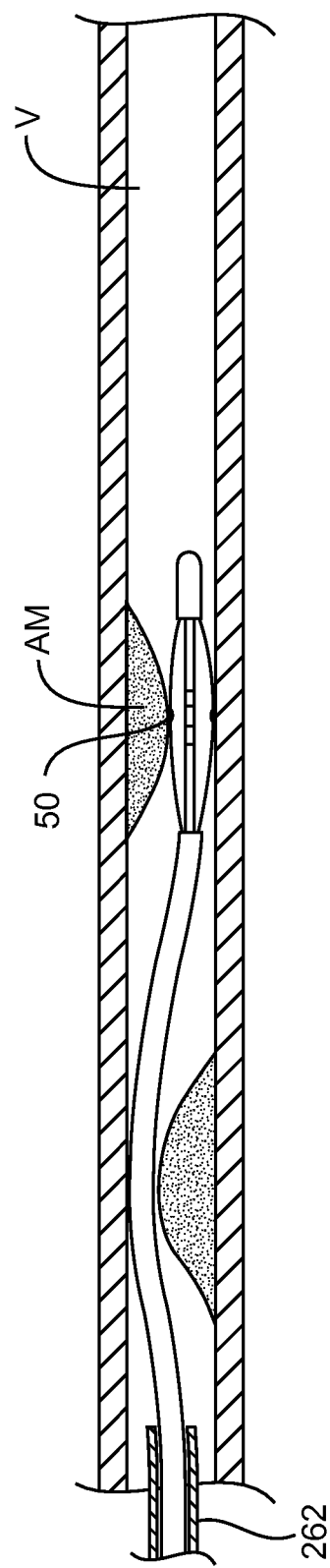
Figure 38E:
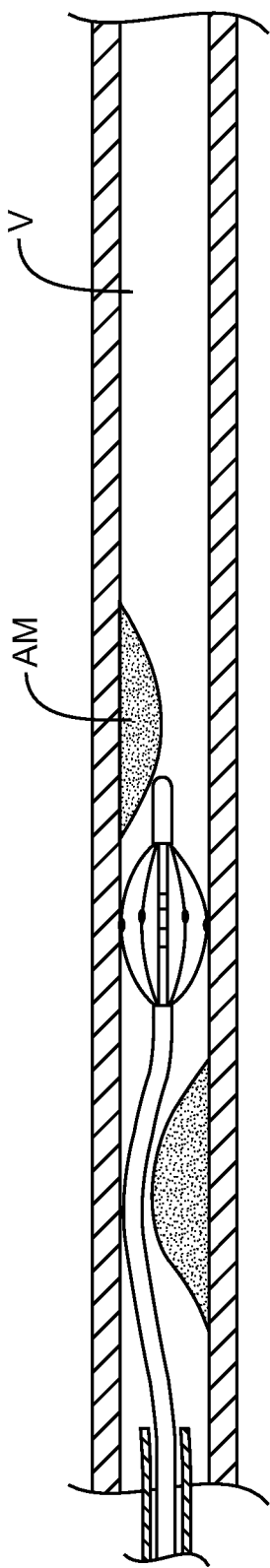
Figure 38F:
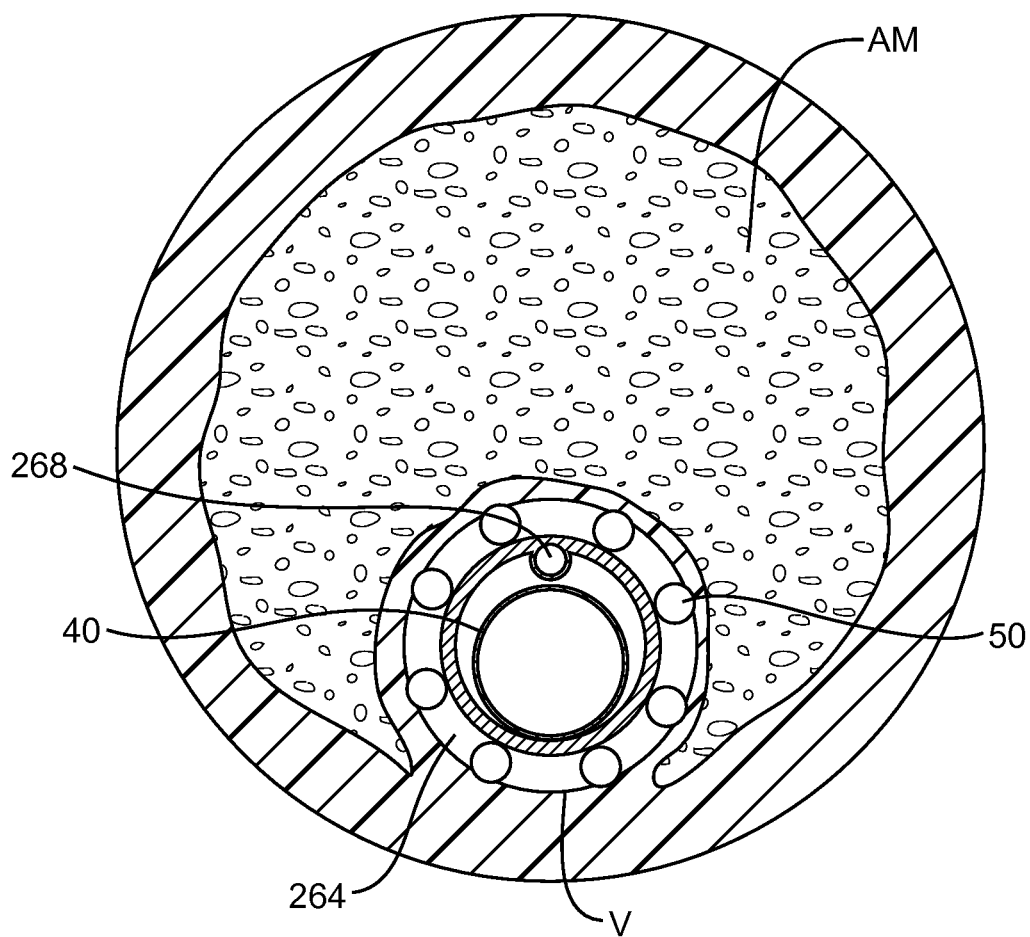
FIGS. 38F-38H are cross sectional views taken across a body lumen and treatment device to show additional aspects of the eccentric treatment methods and devices.
Figure 38G:
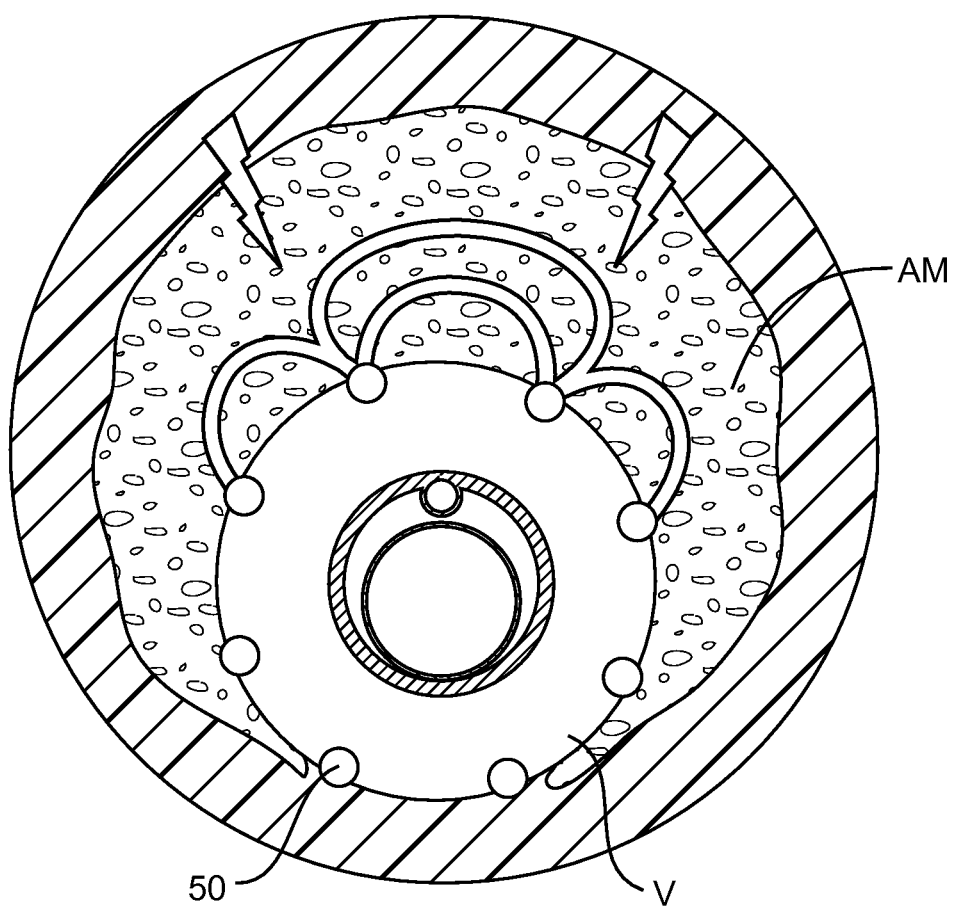
Figure 38H:
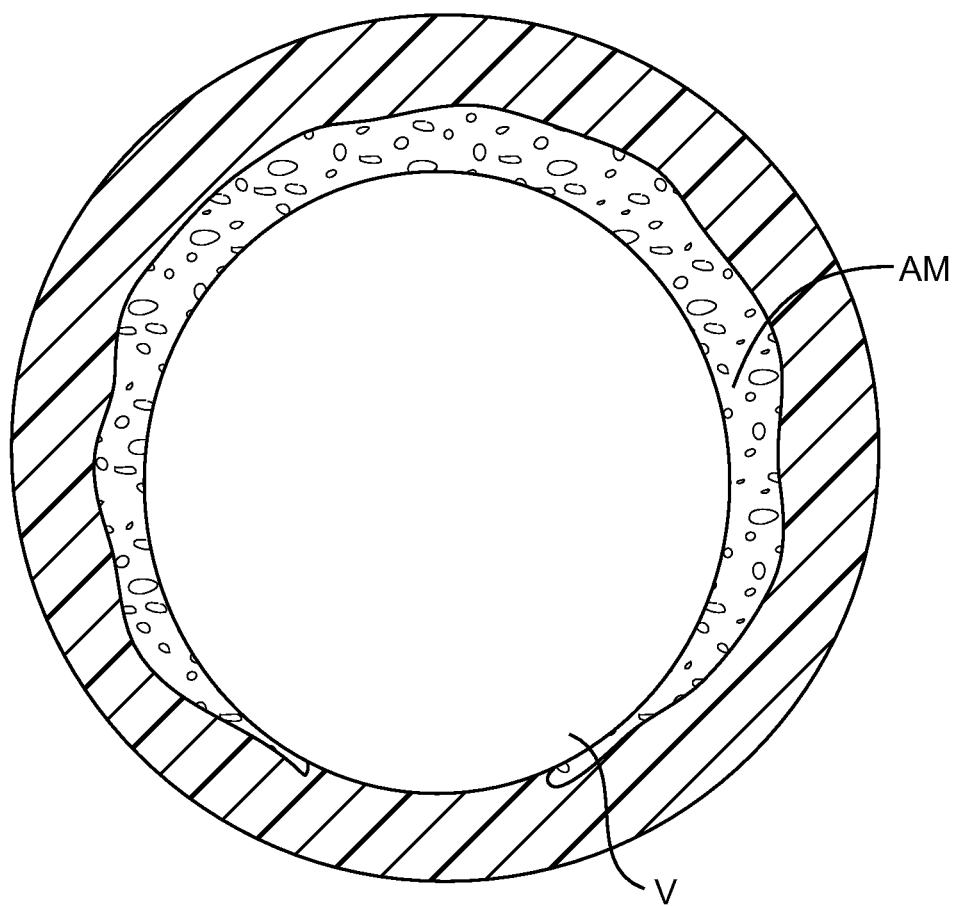
Figure 39A:
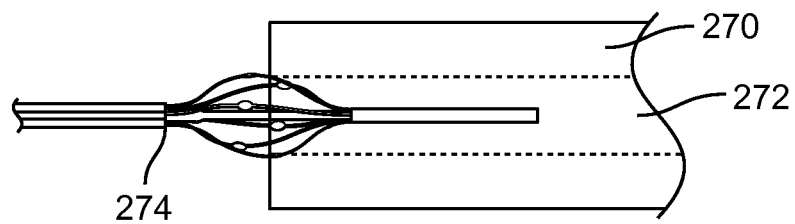
FIGS. 39A and 39B illustrate an eccentric treatment device and method in a gelatin artery model.
Figure 39B:
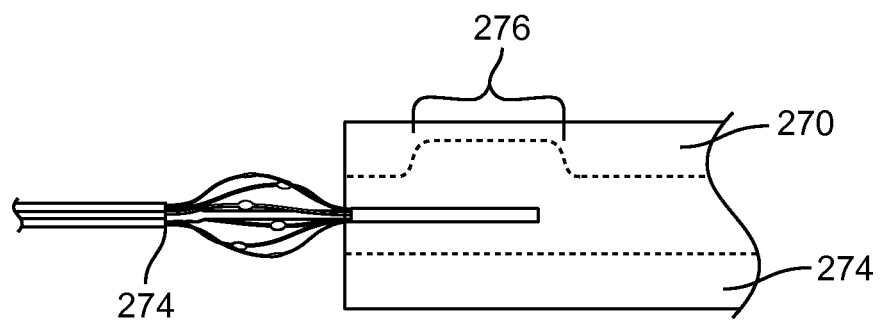

When the imaging catheter detects atherosclerotic material AM as illustrated in FIG. 38C, an appropriate subset (possibly including only a single electrode 50) is activated to remodel the atherosclerotic material AM, as illustrated in FIG. 38D, and the open vessel lumen size increases moderately during treatment. The catheter is pulled proximally to the next atheroma, which is again detected and treated. A cross section of the limited open lumen prior to treatment is schematically illustrated in FIG. 38F, which also illustrates a saline flush or irrigation lumen 268 of the catheter 264. Treatment energy and the moderate increase in the open lumen diameter of the vessel V are schematically illustrated in the cross section of FIG. 38G. After a healing response gradually increases the open lumen diameter, the longer term open lumen results schematically illustrated in FIG. 38H may then be provided.

Referring now to FIGS. 38A and B, eccentric material removal in a gelatin artery model 270 are presented. Prior to the test, the artery model includes a consistent lumen 272 as seen in FIG. 38A. A test eccentric treatment catheter 274 having an expandable basket supporting a circumferential array of electrodes is introduced into lumen 272, with the expandable basket supporting the electrodes in engagement with the luminal wall. Selected electrodes of test catheter 274 were energized so as to eccentrically treat the gelatin artery model 274, thereby effecting eccentric remodeling of the gelatin model, in this case by removing an eccentric volume 276 from along one side of lumen 272. The orientation and amount of the material removed was controlled by selectively energizing electrodes of test catheter 274.

Figure 40:
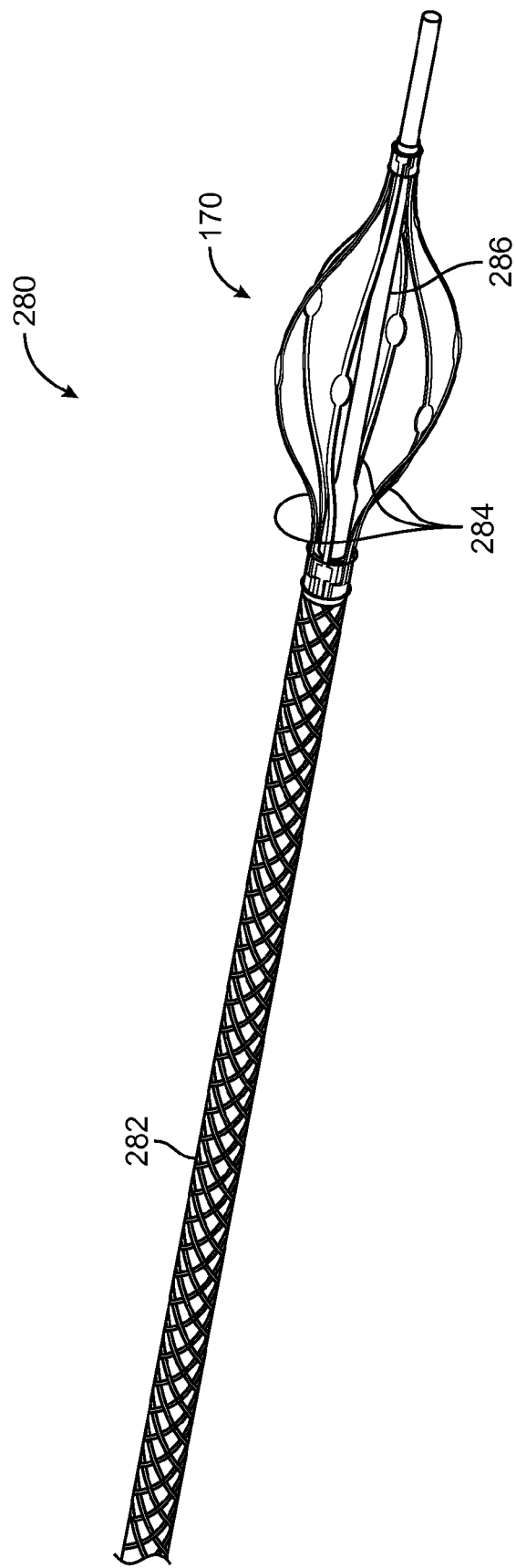
FIG. 40 is a perspective view of an exemplary catheter assembly.

Referring now to FIG. 40, an exemplary catheter system 280 is illustrated. In this embodiment, catheter body 282 includes only a single lumen, which is large enough to accommodate an imaging catheter therein and also to be used as an irrigation lumen to bring irrigation fluid to irrigation ports 284. The lumen may decrease in diameter distally of irrigation ports 284, with the decreased diameter portion 286 fittingly receiving the imaging catheter within the lumen thereof so as to direct the irrigation fluid radially outward through the plurality of irrigation ports. This embodiment may be particularly useful when remodeling atherosclerotic materials using the methods illustrated in FIGS. 38A-38H, in which mild heating improves vessel size without requiring aspiration.

Catheter body 282 may include a braided shaft in which conductive wires (for example copper wires or beryllium-copper wires) are coated with a high temperature and/or high strength insulation material such as a layer of polyimide or the like. The braided wires may be sandwiched between layers of materials forming the shaft of catheter body 282. The shaft may, for example, comprise a plurality of layers of polyethylene, an inner Teflon™ PTFE layer, an outer nylon layer, and the like.

The wires of shaft 282 may be braided so as to inhibit capacitive losses between wires when electrical currents run through them. Capacitive losses may be decreased when a wire that carries a current from an energy source to an electrode of the catheter system and a wire that carries a current from an electrode back to the energy source are not parallel, but at an angle, ideally being perpendicular. This may be achieved by braiding the wires with appropriate pitch or a number of peaks per inch. The basket structure 170 of catheter system 280 may be included, with the basket structure being described in more detail with reference to FIGS. 29A-29H. Guide 286 may extend through basket 170 and may comprise a material transparent to the imaging catheter, optionally comprising HDPE, PET, or the like.

Still further alternatives are available. For example, another way to employ RF energy to remodel atherosclerotic material may be to energize a plurality of the adjacent electrodes with differing RF signals so as to employ the adjacent electrodes as a phase-array. A phase array can direct or steer an electromagnetic signal in a desired direction using constructive and destructive interferences between signals of adjacent elements of the array. By controlling phases of the adjacent signals, a phase array of electrodes may provide a focused and/or steerable RF signal.

Along with controlling steering and directionality, adjusting phases of adjacent RF electrodes may allow focusing of some or most of the RF energy at a desired depth D inside the atherosclerotic material while inhibiting RF energy delivery between the electrode surfaces and depth D using constructive and destructive interference between the signals. For example, such a system may be employed to preserve the cap of a plaque so as to reduce restenosis. Inhibiting heating of the cap while focusing energy toward an internal portion of the plaque may lower an immune response to heat that could otherwise lead to restenosis. Hence, inhibiting heating of the cap may reduce restenosis.

In general, the present invention may use of highly elastic, expandable structures, particularly of expandable structures formed from structural members separated by perforations so as to define a "basket." Such structures can conform to an artery diameter before, during, and/or after atherosclerotic material removal. This expandability allows for direct contact of the electrodes against atheroma, although the systems of the present invention may also make use of conductive fluid environments to complete an RF energy path, or conversely, use non-conductive fluid to enhance energy directed through tissue. Multiple electrodes can be distributed circumferentially around an intermediate portion of the expandable structure, and a subset of these electrodes can be activated to allow for eccentric tissue remodeling and/or ablation.

Atheroma may be identified and targeted by intravascular imaging, and these capabilities may be integrated into the remodeling and/or ablation catheter. Preferably, the intravascular imaging capabilities will be deployed in a separate catheter which can be advanced within, and removed from the ablation catheter. In general, this intravascular imaging capability allows the progress of the therapy to be monitored so that wall perforation can be avoided, while ideally reducing occlusion to no more than 15% of the overall native vessel diameter (either upon completion of the treatment or after subsequent tissue healing). The ablation catheter may further allow the use of localized radiation or drug delivery for anti-restenosis treatments. The ablation catheter may include a relatively large lumen allowing selective use of an intravascular imaging system, a radiation delivery or other treatment catheter, an aspiration of debris and vaporization gases, with these uses often being employed sequentially. A guidewire may make use of this or a separate lumen, and the guidewire may be removed to allow access for the restenosis and/or imaging catheters.

While the exemplary embodiments have been described in some detail, by way of example and for clarity of understanding, those of skill in the art will recognize that a variety of modification, adaptations, and changes may be employed. Hence, the scope of the present invention should be limited solely by the appending claims.

What is claimed is:

1. A catheter system for eccentric removal of atherosclerotic material from a blood vessel of a patient, the system comprising:
    an elongate flexible catheter body having a proximal end and a distal end with an axis therebetween, and a lumen extending between the proximal end and the distal end;
    an aspiration source coupled with the lumen, wherein the lumen is configured for aspiration of debris from within the blood vessel when coupled to the aspiration source;
    a restenosis inhibitor advanceable distally within the lumen so as to inhibit restenosis of the blood vessel, wherein the restenosis inhibitor comprises a brachytherapy catheter having a radiation source;
    a radially expandable structure near the distal end of the catheter body, the radially expandable body including a plurality of flexible non-overlapping struts;
    a plurality of electrodes supported by the radially expandable structure and oriented to be urged radially against atherosclerotic material when the expandable structure expands, the plurality of electrodes comprising a circumferentially distributed array of electrodes of which each electrode is selectively energizable, wherein adjacent electrodes are axially offset from one another;
    an atherosclerotic material detector disposed near the distal end of the catheter body configured for circumferential measurement and detection of atherosclerotic material; and
    a power source electrically coupled to the electrodes with a controller, the controller configured to selectively energize an eccentric subset of the electrode array in response to the measured atherosclerotic material so as to eccentrically ablate the measured atherosclerotic material.

2. The catheter system of claim 1, further comprising an aspiration connector in fluid communication with the lumen at the proximal end of the catheter body connecting the lumen to the aspiration source so as to allow aspiration of debris from within the blood vessel through the lumen.

3. The catheter system of claim 2, further comprising proximal and distal ablation debris barriers disposed proximally and distally of the electrodes, respectively, and an aspiration port disposed between the proximal and distal barriers for removal of ablation debris during atherosclerotic material ablation.

4. The catheter system of claim 1, wherein the atherosclerotic material detector comprises an ultrasound transducer of an intravascular ultrasound catheter, the intravascular ultrasound catheter disposed in the lumen.

5. The catheter system of claim 1, further comprising an irrigation lumen extending between the proximal end of the catheter body and the distal end of the catheter body that is coupled with an irrigation source, the irrigation lumen being separate from the aspiration lumen.

6. The catheter system of claim 1, wherein the electrodes define a circumferentially oriented electrode array.

7. The catheter system of claim 6, wherein struts of the radially expandable structure have perforations disposed therebetween so as to define an expandable basket, wherein the basket has a proximal portion and a distal portion with an intermediate portion disposed therebetween, the array of electrodes being supported along the intermediate portion so as to engage the adjacent atherosclerotic material when the basket is expanded within the blood vessel, and further comprising an aspiration port in fluid communication with an interior of the basket.

8. The catheter system of claim 1, wherein the array of electrodes comprises at least 6 alternatively selectable electrodes distributed circumferentially about the axis.

9. The catheter system of claim 8, wherein the controller selectively energizes electrodes by directing RF energy thereto.

10. The catheter system of claim 1, wherein the atherosclerotic material detector comprises an ultrasound transducer or optical coherence reflectometry.

11. The catheter system of claim 1, further comprising a display showing an image of circumferential atherosclerotic material thickness distributed about the catheter axis.

12. A catheter for remodeling of atherosclerotic material of a blood vessel of a patient, the catheter comprising:
   an elongate flexible catheter body having a proximal end and a distal end with lumen therebetween;
   a radially expandable basket near the distal end of the catheter body, the basket formed from a plurality of struts and the basket having a proximal portion and a distal portion with an intermediate portion disposed therebetween, wherein each strut includes a region of localized widening in a central portion of the strut; and
   a circumferential electrode array supported by the radially expandable basket and distributed circumferentially about the intermediate portion of the radially expandable basket, wherein each electrode of the electrode array is selectively energizable, wherein each electrode is supported by one of the regions of localized widening, wherein each region of localized widening does not extend substantially beyond its associated electrode;
   an aspiration port providing fluid communication between the aspiration lumen and an interior of the basket; and
   a power source electrically coupled to the electrodes with a controller, the controller configured to selectively energize an eccentric subset of the electrode array in response to a circumferential measurement of the atherosclerotic material so as to selectably remodel adjacent eccentric atherosclerotic material while the basket is expanded within the blood vessel.

13. A system for eccentric removal of material from a body lumen of a patient, the system comprising:
   an elongate body having a proximal end and a distal end with an axis therebetween;
   a radially expandable structure near the distal end of the catheter body, the radially expandable structure comprising a plurality of struts, each strut including a region of localized widening in a central portion of the strut;
   a plurality of electrodes supported on the radially expandable structure and oriented to be urged radially against the material when the expandable structure expands within the body lumen, the plurality of electrodes comprising a circumferentially distributed array of electrodes of which each electrode is selectively energizable, wherein each electrode is supported by one of the regions of localized widening, wherein each region of localized widening does not extend substantially beyond its associated electrode;
   a material detector disposed near the distal end of the catheter body configured for circumferential measurement and detection of the material; and
   a power source electrically coupled to the electrodes with a controller, the controller configured to selectively energize an eccentric subset of the electrodes in response to the circumferential measurement and detection of the material so as to eccentrically ablate the measured material.

* * * * *